United States Patent
Lane et al.

(10) Patent No.: US 8,731,686 B2
(45) Date of Patent: May 20, 2014

(54) BURR HOLE PLUG HAVING DUAL SLIDABLE CLAMPING MECHANISMS

(75) Inventors: Courtney Lane, Ventura, CA (US);
Jesse Geroy, North St. Paul, MN (US);
James C. Makous, Santa Clarita, CA (US); Todd Whitehurst, Santa Clarita, CA (US); Matthew Flowers, Irvine, CA (US); John Michael Barker, Ventura, CA (US); Terry Ferrell, Lino Lakes, MN (US); John Swoyer, Andover, MN (US); Brett Schleicher, Valencia, CA (US); Jeff Gagnon, Champlain, MN (US); Andrew DiGiore, Santa Monica, CA (US); Ellis Garai, Sherman Oaks, CA (US); Kristen Jaax, Santa Clarita, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1202 days.

(21) Appl. No.: 12/630,761

(22) Filed: Dec. 3, 2009

(65) Prior Publication Data
US 2010/0145357 A1    Jun. 10, 2010

Related U.S. Application Data

(62) Division of application No. 12/258,382, filed on Oct. 24, 2008, now abandoned.

(60) Provisional application No. 60/983,099, filed on Oct. 26, 2007.

(51) Int. Cl.
*A61N 1/00* (2006.01)

(52) U.S. Cl.
USPC ......................................... 607/116

(58) Field of Classification Search
USPC ............... 607/116; 606/129–130; 248/56–57; 600/378
See application file for complete search history.

(56) References Cited

U.S. PATENT DOCUMENTS 979,652 A * 12/1910 Church ................... 285/137.11
2,186,277 A    1/1940 Tetens
(Continued)

FOREIGN PATENT DOCUMENTS

EP    0911061    4/1999
JP    S55-112538    7/1980
(Continued)

OTHER PUBLICATIONS

EPO Communication regarding the extended European Search Report for Application No. 12181240.8-2305 dated Dec. 4, 2012, Applicant: Boston Scientific Neuromodulation Corporation (6pages).
(Continued)

*Primary Examiner* — Mark W Bockelman
(74) *Attorney, Agent, or Firm* — Vista IP Law Group LLP

(57) ABSTRACT

A burr hole plug comprises a plug base configured for being mounted around a burr hole. The plug base includes an aperture through which an elongated medical device exiting the burr hole may pass. The burr hole plug further comprises a retainer configured for being mounted within the aperture of the plug base. The retainer further includes first and second slidable clamping mechanisms configured for securing the medical devices therebetween within the aperture of the plug base. A method comprises introducing the medical device through the burr hole, mounting a plug base around the burr hole, such that the medical device extends through the plug base aperture, mounting the retainer within the aperture of the plug base, and sliding the first and second clamping mechanisms secure the medical device therebetween.

22 Claims, 52 Drawing Sheets

(56) References Cited

U.S. PATENT DOCUMENTS

| | | | |
|---|---|---|---|
| 2,912,712 A | 11/1959 | Shamban et al. |
| 4,328,813 A | 5/1982 | Ray |
| 4,805,634 A | 2/1989 | Ullrich et al. |
| 5,116,345 A | 5/1992 | Jewell et al. |
| 5,464,446 A | 11/1995 | Dreesen et al. |
| 5,776,144 A | 7/1998 | Leysieffer et al. |
| 5,843,150 A | 12/1998 | Dreesen et al. |
| 5,865,842 A | 2/1999 | Knuth et al. |
| 5,916,154 A | 6/1999 | Hobbs et al. |
| 5,927,277 A | 7/1999 | Baudino et al. |
| 5,984,930 A | 11/1999 | Maciunas et al. |
| 5,993,463 A | 11/1999 | Truwit |
| 6,006,124 A | 12/1999 | Fischell et al. |
| 6,016,449 A | 1/2000 | Fischell et al. |
| 6,044,304 A | 3/2000 | Baudino |
| 6,073,048 A | 6/2000 | Kieval et al. |
| 6,094,598 A | 7/2000 | Elsberry et al. |
| 6,117,143 A | 9/2000 | Hynes et al. |
| 6,128,537 A | 10/2000 | Rise |
| 6,134,477 A | 10/2000 | Knuteson |
| 6,171,239 B1 | 1/2001 | Humphrey |
| 6,210,417 B1 | 4/2001 | Baudino et al. |
| 6,269,270 B1 | 7/2001 | Boveja |
| 6,284,729 B1 | 9/2001 | Bernfield et al. |
| 6,321,104 B1 | 11/2001 | Gielen et al. |
| 6,353,762 B1 | 3/2002 | Baudino et al. |
| 6,356,729 B1 | 3/2002 | Sasaki et al. |
| 6,356,777 B1 | 3/2002 | Garfield et al. |
| 6,374,140 B1 | 4/2002 | Rise |
| 6,447,443 B1 | 9/2002 | Keogh et al. |
| 6,464,687 B1 | 10/2002 | Ishikawa et al. |
| 6,482,182 B1 | 11/2002 | Carroll et al. |
| 6,560,486 B1 | 5/2003 | Osorio et al. |
| 6,571,127 B1 | 5/2003 | Ben-Haim et al. |
| 6,609,020 B2 | 8/2003 | Gill |
| 6,795,737 B2 | 9/2004 | Gielen et al. |
| 6,845,267 B2 | 1/2005 | Harrison et al. |
| 6,920,359 B2 | 7/2005 | Meadows et al. |
| 6,950,707 B2 | 9/2005 | Whitehurst |
| 7,146,222 B2 | 12/2006 | Boling |
| 7,204,840 B2 | 4/2007 | Skakoon et al. |
| 7,235,084 B2 | 6/2007 | Skakoon et al. |
| 7,833,253 B2 | 11/2010 | Ralph et al. |
| 2002/0052610 A1 | 5/2002 | Skakoon et al. |
| 2002/0156372 A1 | 10/2002 | Skakoon et al. |
| 2004/0034367 A1 | 2/2004 | Malinowski |
| 2005/0010261 A1 | 1/2005 | Luders et al. |
| 2005/0049649 A1 | 3/2005 | Luders et al. |
| 2005/0092707 A1 | 5/2005 | Chantalat |
| 2005/0182425 A1 | 8/2005 | Schulte et al. |
| 2005/0182464 A1 | 8/2005 | Schulte et al. |

FOREIGN PATENT DOCUMENTS

| | | |
|---|---|---|
| WO | WO 9808554 | 3/1998 |
| WO | WO 9955408 | 11/1999 |
| WO | WO 0013743 | 3/2000 |
| WO | WO 2005079903 | 9/2005 |
| WO | WO 2005079903 A2 | 9/2005 |

OTHER PUBLICATIONS

Non-Final Office Action dated Oct. 7, 2009 in U.S. Appl. No. 12/258,382, Applicant: Courtney Lane, et al., (24 pages).

Final Office Action dated May 14, 2010 in U.S. Appl. No. 12/258,382, Applicant: Courtney Lane, et al., (16 pages).

Advisory Action dated Jul. 12, 2010 in U.S. Appl. No. 12/258,382, Applicant: Courtney Lane, et al., (3 pages).

Appeal Brief dated Oct. 12, 2010 in U.S. Appl. No. 12/258,382, Applicant: Courtney Lane, et al., (16 pages).

Final Office Action dated Jan. 4, 2011 in U.S. Appl. No. 12/258,382, Applicant: Courtney Lane, et al., (15 pages).

Non-Final Office Action dated Jun. 22, 2011 in U.S. Appl. No. 12/258,382, Applicant: Courtney Lane, et al., (14 pages).

PCT International Search Report for PCT/US2008/081226, Applicant: Boston Scientific Neuromodulation Corporation, Form PCT/ISA/210 and 220, dated Jul. 10, 2009 (11 pages).

PCT Written Opinion of the International Search Authority for PCT/US2008/081226, Applicant: Boston Scientific Neuromodulation Corporation, Form PCT/ISA/237, dated Jul. 10, 2009 (10 pages).

Office Action dated Oct. 28, 2011 for U.S. Appl. No. 12/258,382, Inventor: Courtney Lane et al., filing date: Oct. 24, 2008 (18pages).

Communication pursuant to Rules 161(1) and 162 EPC dated Jun. 8, 2010 issued by the European Patent Office for European Patent Application No. 08841477.6-2305 (PCT/US2008081226), (2pages).

Communication under Rule 71(3) EPC dated Mar. 12, 2012 issued by the European Patent Office for European Patent Application No. 08841477.6-2305 (PCT/US2008081226), (4pages).

Partial PCT International Search Report for related application PCT/US2008/081226, Applicant: Boston Scientific Neuromodulation Corporation, Form PCT/ISA/206, dated Feb. 2, 2009. (7 pages).

PCT International Preliminary Report on Patentability (Chapter I of the Patent Cooperation Treaty) for PCT/US2008/081226, Applicant: Boston Scientific Neuromodulation Corporation, Form PCT/IB/326 and 373, dated May 6, 2010 (12 pages).

JPO Communication dated Mar. 7, 2013 for Japanese Patent Application No. 2010-531300, Applicant: Boston Scientific Neuromodulation Corporation, (4pages) including a partial translation prepared by Nakamura & Partners (3pages).

Australian Office Action dated Jan. 30, 2013 in Australian Patent Application 2008316640, Applicant: Boston Scientific Neuromodulation Corporation, (6pages).

European Office Action dated Aug. 2, 2013 in European Patent Application 12181240.8-1652, Applicant: Boston Scientific Neuromodulation Corporation, (3pages).

Japanese Office Action dated Aug. 14, 2013 in Japanese Patent Application 2010-531300, Applicant: Boston Scientific Neuromodulation Corporation, (7pages) including Partial Translations prepared by Nakamura & Partners (3pages).

* cited by examiner

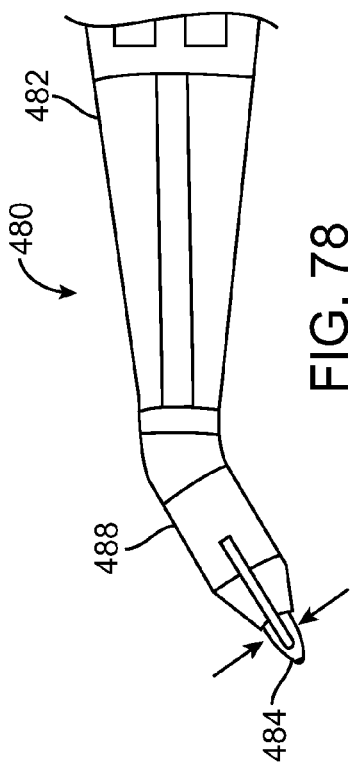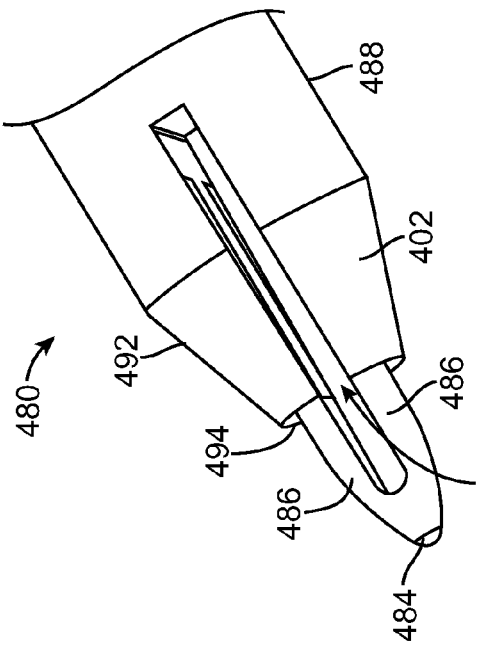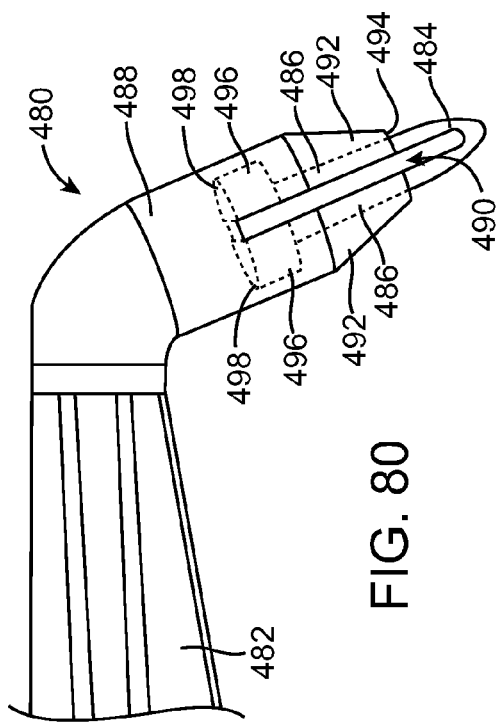

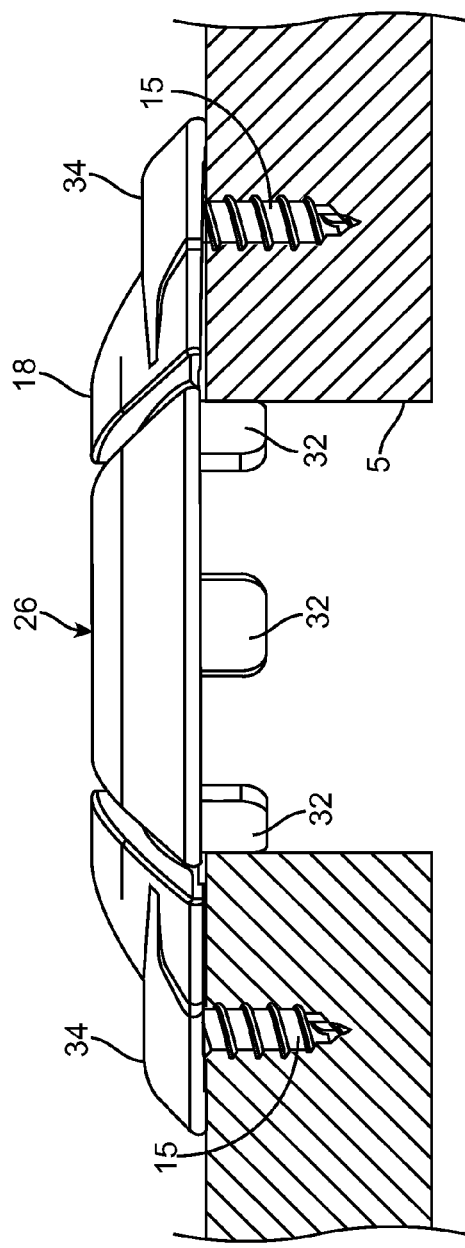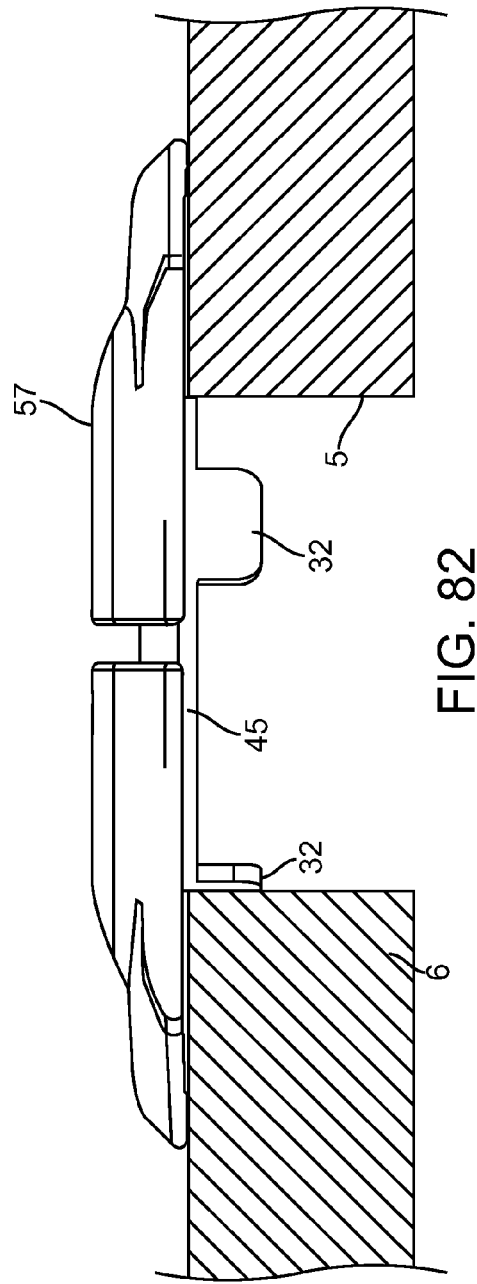

BURR HOLE PLUG HAVING DUAL SLIDABLE CLAMPING MECHANISMS

RELATED APPLICATION DATA

The present application is a divisional of U.S. patent application Ser. No. 12/258,382, filed Oct. 24, 2008, which claims the benefit under 35 U.S.C. §119 to U.S. Provisional Patent Application Ser. No. 60/983,099, filed Oct. 26, 2007. The foregoing applications are each hereby incorporated by reference into the present application in their entirety.

FIELD OF THE INVENTION

The present inventions relate to apparatus for securing elongated medical devices, such as catheters or leads, within a cranial burr hole.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation via stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical procedure for the treatment of advanced Parkinson's Disease. There have been approximately 30,000 patients world-wide that have undergone DBS surgery. Consequently, there is a large population of patients who will benefit from advances in DBS treatment options.

During DBS procedures, at least one burr hole is meticulously cut through the patient's cranium so as not to damage the brain tissue below, a large stereotactic targeting apparatus is mounted to the patient's cranium, and a cannula is scrupulously positioned towards the target site in the brain. A stimulation lead is then introduced through the cannula, through the burr hole, and into the parenchyma of the brain, such that one or more electrodes located on the lead are strategically placed at a target site in the brain of the patient. Once the lead is properly positioned, the portion of the lead exiting the burr hole is subcutaneously routed underneath the patient's scalp to an implantable pulse generator (IPG) implanted in the patient at a site remote from the burr hole (e.g., the patient's shoulder or chest region). Further details discussing the treatment of diseases using DBS are disclosed in U.S. Pat. Nos. 6,845,267, 6,845,267, and 6,950,707, which are expressly incorporated herein by reference.

Significantly, it is crucial that proper location and maintenance of the lead position be accomplished in order to continuously achieve efficacious therapy. This is especially so with DBS applications, in which cases, the target site (or sites) that is intended for electrical stimulation is about the size of a pea and is located deep within the patient's brain. Thus, lead displacements of less than a millimeter may have a deleterious effect on the patient's therapy. Therefore, it is important that that the electrode(s) of the lead be accurately located at the target site and that such electrode(s) be securely maintained at the target site during and after implantation of the lead. In addition, it is important that the burr hole be sealed around the stimulation lead to prevent infection or leakage of cerebrospinal fluid.

To address these issues, a cranial burr hole plug is installed within the burr hole during the implantation procedure to hold the stimulation lead in place, as well as to seal the burr hole. Typically, the burr hole plug is composed of a multitude of components, including a ring-shaped base, a retainer, and a cap, that are integrated together to form the burr hole plug.

In particular, before the stimulation lead is introduced through the burr hole, the ring-shaped plug base is placed about the burr hole, and is then permanently mounted to the patient's cranium using conventional means, such as screws. The stimulation lead is then introduced through the plug base and into the parenchyma of the brain. Notably, any displacement of the portion of the lead exiting the burr hole will result in the translation of the electrodes positioned in the brain relative to the target site, thereby requiring the lead to be repositioned—a time-consuming process.

Thus, once the lead is properly located at the tissue site, the retainer is installed within the plug base (typically in an interference arrangement, such as a snap-fit arrangement) to temporarily secure the lead, thereby preventing migration of the lead relative to the target site during subsequent manipulation of the proximal end of the lead and installation of the cap. In one exemplary embodiment, the retainer comprises a disk having a slot for receiving the lead and a clamping mechanism that can be rotated within the slot towards a mating surface on the disk to frictionally clamp the received lead therebetween. The clamping mechanism may have one or more locking mechanisms that can engage or disengage complementary locking mechanisms on the disk to prevent rotation of the clamping mechanism. The portion of the stimulation lead exiting the retainer can then be bent downward towards the plane of the disk into a recess formed in the plug base, and the cap can be installed onto the plug base over the retainer to permanently secure the lead within the recess, as well as to seal the burr hole. Further details regarding these types of burr hole plugs are disclosed in U.S. Patent Publication No. 2002/0156372.

It can thus be appreciated from the foregoing that the burr hole plug serves as the platform for the entire DBS system, and therefore, it is important for this component to be robust, well-designed, and easy to use. Importantly, the burr hole plug should be designed such that lead migration is minimized during installation of the burr hole plug. While prior art burr hole plugs have proven to be useful in the DBS context, there are still improvements that can be made.

As one example, prior art burr hole plugs are typically composed of biocompatible and non-corrosive material, such as a plastic (e.g., polypropylene or polycarbonate), which although less durable than other materials, is compatible with MRI, and unlike titanium, will not distort the MRI. To ensure that the burr hole plug is durable enough during its installation within the burr hole, the plug base typically has a closed architecture (closed ring). Because of this, as well as the location of the lead guidance equipment at the proximal end of the lead, the plug base must be mounted within or around the burr hole prior to delivery of the stimulation lead through the burr hole. While this, in itself, does not create a problem, if the lead is inadvertently delivered into the patient's brain before the plug base is located at the burr hole, the lead will need to be backed out of the burr hole and the lead delivery process initiated again. Also, because prior art plug bases are composed of a single piece, there is a risk that the plug base may fracture if the plug base is anchored to tightly to the cranium of the patient, especially if the bottom surface of the plug base does not match the curvature of the cranium.

Because the retainer installed within the plug base is also composed of plastic material, the retainer will typically deform somewhat during its installation within the plug base and during manipulation of the clamping mechanism to stabilize the lead. In addition, because the clamping mechanism will deform somewhat along its length when clamped against the stimulation lead, an unequal force may be applied along the clamping mechanism, thereby weakening the retention force applied to the lead. Also, because of the relatively weak composition of the retainer, the clamping force between it and the mating surface of the disk is limited, thereby limiting the lead retention force of the clamping mechanism. Furthermore, because the application of a downward force is typically necessary to unlock and allow the clamping mechanism to rotate relative to the disk, such downward force may cause the clamping mechanism to be bent too far down, thereby permanently deforming or breaking it. In addition, since burr hole plugs are typically composed of biocompatible polymers that are extremely lubricious, particularly when wetted, the coefficient of friction of the retention surface of the clamping mechanism, as well as the mating surface of the disk, may be relatively low. As a result, the lead may migrate when only a moderate amount of tensile force is applied to it.

As another example of a problem suffered from prior art burr hole plugs, the retainer may rotate within the plug base, potentially resulting in the inadvertent movement of the stimulation lead from the target site. Such rotation of the retainer mechanism may typically occur in response to the manipulation of the clamping mechanism, and in particular, a downward force applied to the clamping mechanism that causes partial disengagement between the retaining disk to which the clamping mechanism is mounted and the plug base, and a lateral force applied to the clamping mechanism that causes the disengaged disk to rotate within the plug base.

As still another example, many DBS systems have evolved from a single lead (unilateral) system to double lead (bilateral) systems; for example, one lead is used to perform STN stimulation, while another lead is used to perform thalamus stimulation. Other DBS systems may use a recording lead to record brain signals that are then fed back to the IPG to control the stimulation applied to the target site by the stimulation lead(s). However, prior art burr hole plugs are not designed to stabilize more than one stimulation lead at time. This is because the slot within the disk can only secure leads that exit the burr hole along the diameter of the disk, although the leads may be offset from the diameter. Thus, despite the fact that the target sites stimulated and/or recorded by the leads may be adjacent to each other, multiple burr holes, each accommodating a stimulation lead and burr hole plug, are typically formed in the cranium of the patient when multiple stimulation leads are used. By creating multiple burr holes, the risk to the patient, time in the operating room (which also increases patient risk), the materials and staff needed in the operating room, and cost of the procedure are all increased, so a burr hole plug that can accommodate multiple leads through one burr hole is preferred.

As yet another example, it is preferable that the portion of the stimulation lead exiting the burr hole be disposed at an angle perpendicular to the length of the slot of the retaining disk when bent down towards the plane of the disk, so that the lead does not move along the slot when tensed. However, because the recess of the plug base in which the lead is seated may be located obliquely (as opposed to perpendicular) to the slot, it may be difficult to bend the lead perpendicular to the slot towards the base recess if the lead support mechanism is not perfectly oriented relative to the plug base. In addition, rotation of the lead support mechanism relative to the base while the lead is seated within the base recess may cause the lead to be displaced from the target site.

In yet another example, the plug base must be securely held in place while anchoring it to the cranium via screws. The retainer must also be mounted within the plug base, such that the retaining disk is properly seated within the plug base without disturbing the position of the lead, which is precariously held by the stereotactic targeting apparatus. However, due to the diminutive size of the burr hole plug components, they are difficult to position, manipulate, and handle. This, in combination with the limited working space between the targeting apparatus and the burr hole, makes it quite difficult to visualize and correctly install the plug within the burr hole and stabilize the lead. While the surgeon is installing the components of the burr hole plug, there is a risk of foreign objects (screws, tools, debris, etc.) falling into the exposed burr hole, as well as slippage of tools within the burr hole. Prior art tools, which stabilize plug bases while covering the burr hole and holding/aligning the screws used to anchor the plug bases, can be utilized. However, the screws often pop-out of these tools unintentionally and do not always screw into the cranium at the correct angle.

Thus, installation of the burr hole plug without disturbing the lead position is nearly an impossible task without specialization of the tools and/or burr hole plug that can center the plug base while it is anchored to the patient's skull and securely hold and mount the retainer to the plug base. Typically, the surgeon may use a special tool that engages the retainer, such that it can be navigated and positioned within the plug base, and then pressed downward to snap-fit it into the plug base. However, this installation tool only engages the retaining disk at one location. Thus, it is possible that the disk may become skewed or tilted while attempting to install it within the plug base, or worse yet, given the spring force stored in the disk, it may be launched from the surgical site.

In yet another example, prior art burr hole plugs are designed to be used with stimulation leads having one size. That is, the dimension between the retaining surface of the clamping device and the mating surface of the disk when the clamping device is in the locked position is designed to be slightly less than the diameter of the lead. If the diameter of the actual lead used with the burr hole plug is smaller than this intended, the retention force applied to the lead by the clamping mechanism will not be sufficient. If the diameter of the actual lead used with the burr hole plug is greater than this intended diameter, too much force will need to be applied to the lead in order to place the clamping mechanism within the locking position, thereby potentially damaging the retainer and/or the lead.

As yet another example, once the plug base is mounted to the patient's cranium via screws, it is difficult to adjust the position of the plug base if it is desired. Also, due to the relatively large size of the stereotactic targeting apparatus, there is often little working space available between the targeting apparatus and the burr hole to anchor the plug base to the cranium of the patient.

There, thus, remains a need for improved burr hole plug designs.

SUMMARY OF THE INVENTION

In accordance with one aspect of the present inventions, a cranial burr hole plug is provided. The burr hole plug comprises a plug base configured for being mounted around a cranial burr hole. The plug base includes an aperture through which an elongated medical device exiting the burr hole may pass. The plug base aperture has a suitable shape (e.g., circular) and a suitable dimension (e.g., equal to or less than 25 mm). In one embodiment, the plug base includes an open slot configured for laterally receiving the medical device.

The burr hole plug further comprises a retainer configured for being mounted within the aperture of the plug base. In one embodiment, the retainer is configured for being removably mounted within the aperture of the plug base. In another embodiment, the plug base includes at least one inner annular ledge configured for supporting the retainer when mounted within the aperture of the plug base. The retainer further includes first and second slidable clamping mechanisms configured for securing the medical devices therebetween within the aperture of the plug base. While the present inventions should not be so limited in their broadest aspects, the use of two slidable clamping mechanisms conveniently facilitates the securing of more than one medical device within a single cranial burr hole. For example, the first and second slidable clamping mechanisms can be configured for securing the medical devices along any one of a plurality of chords of the aperture of the plug base.

In one embodiment, the retainer further includes a retainer support (e.g., a disk) and a slot formed in the retainer support for receiving the medical devices. In one embodiment, the slot may be open slot configured for laterally receiving the medical device. In another embodiment, the retainer support includes first and second portions, and the retainer further includes a hinge coupled to the first and second flange portions, whereby the first and second flange portions can be alternately hinged open to laterally receive the medical lead within the slot and hinged closed to encompass the medical lead within the slot.

The first and second clamping mechanisms may be slidably engaged with the retainer support to secure the medical devices received within the slot. In this case, each of the first and second clamping mechanisms may have a clamping bar and a slidable flange slidably engaged with the retainer support to laterally slide the clamping bar to secure the medical devices received within the slot. At least one of the clamping bars has a clamping surface with relief features, e.g., to increase the retention force applied to the medical device. The retainer may further include first and second recesses formed in the retainer support on opposite sides of the slot, and the slidable flanges of the first and second clamping mechanisms may be slidably engaged within the respective recesses. In this case, the retainer may include first and second pairs of C-channels, each pair disposed on opposite sides of the respective recess, such that a pair of opposing edges of each slidable flange are respectively received within the respective C-channels.

The burr hole plug may comprise other components in addition to the plug base and retainer. For example, the burr hole plug may comprise fasteners configured for anchoring the plug base to a cranium of a patient, and a cap configured for being mounted to the plug base over the retainer. The plug base may have an exit groove configured for seating the medical device, in which case, the cap may be configured for firmly securing the medical device within the exit groove when the cap is mounted to the plug base.

In accordance with another aspect of the present inventions, a method of performing a medical procedure on a patient is provided. The method comprises introducing at least one elongated medical device (e.g., an electrical lead) through a cranial burr hole of the patient and into the brain tissue of the patient. The method further comprises mounting a plug base around a cranial burr hole, such that the medical device extends through an aperture of the plug base, and mounting a retainer within the aperture of the plug base. The retainer includes first and second clamping mechanisms. The method further comprises sliding the first and second clamping mechanisms secure the medical device(s) therebetween, thereby providing the same advantages described above. In one method, the first and second clamping mechanisms secure the medical devices along an off-center chord of the aperture of the plug base. In another method, the retainer further includes a retainer support and a slot formed in the retainer support for receiving the medical devices, in which case, the method may further comprise receiving the medical device(s) into the slot, wherein the first and second clamping mechanisms are slid relative to the retainer support to secure the at least one medical device received within the slot. The method may further comprise mounting a cap to the plug base over the retainer.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 78 is a perspective view of still another embodiment of a retainer holding tool;

FIG. 79 is a close-up view of the retainer holding tool of FIG. 78;

FIG. 80 is a close-up view of showing a portion of the retainer holding tool of FIG. 78 in phantom;

FIG. 81 is a side view of the plug base of FIG. 8 mounted within a burr hole;

FIG. 82 is a side view of the plug base of FIG. 12 mounted within a burr hole;

DETAILED DESCRIPTION OF THE EMBODIMENTS

Figure 1:
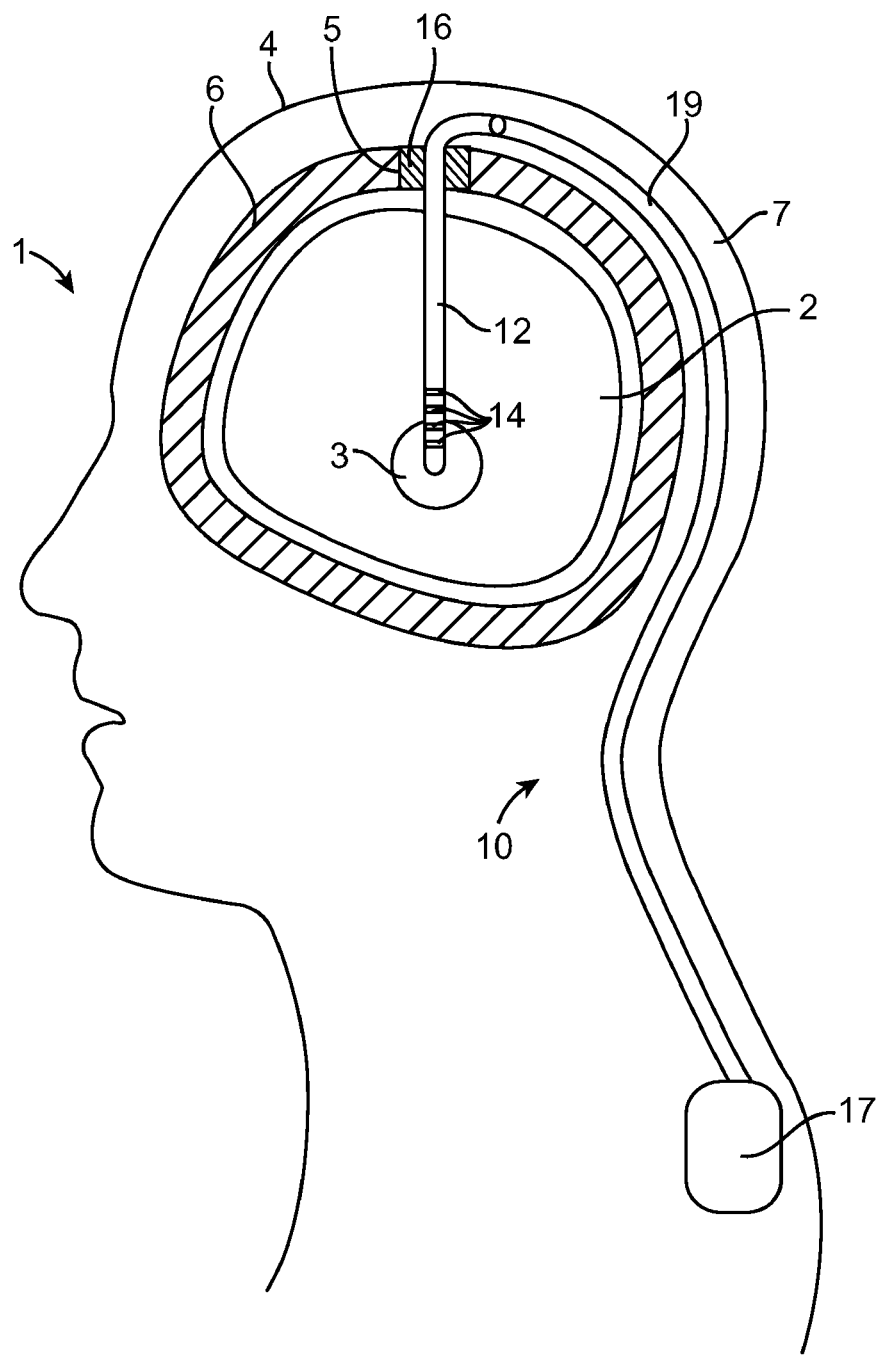
FIG. 1 is a plan view of a Deep Brain Stimulation (DBS) system constructed in accordance with one embodiment of the present inventions, wherein the DBS system is particularly shown implanted within a patient.
Figure 2:
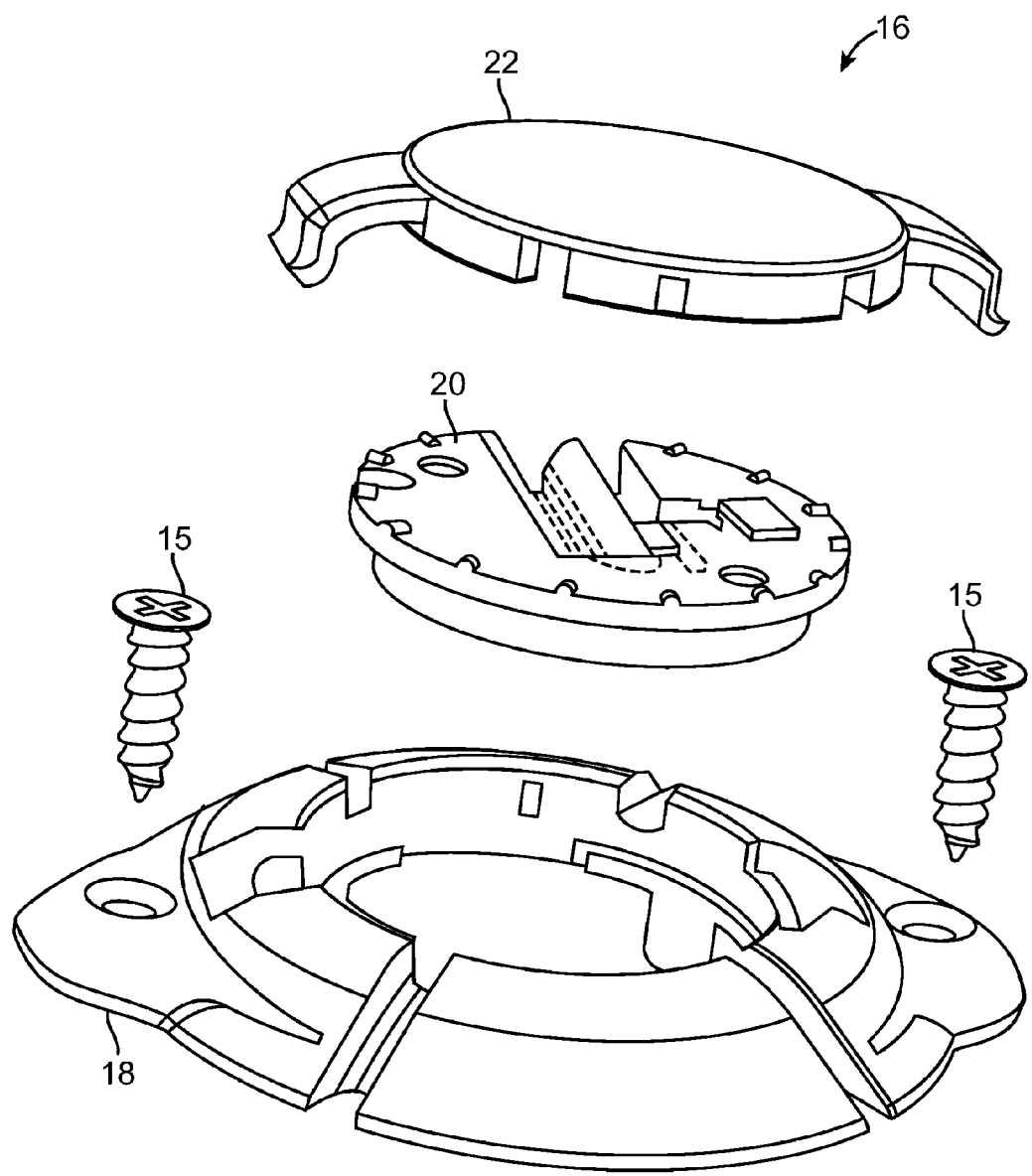
FIG. 2 is an exploded perspective view of a first embodiment of a burr hole plug that can be used in the DBS system of FIG. 1.
Figure 3:
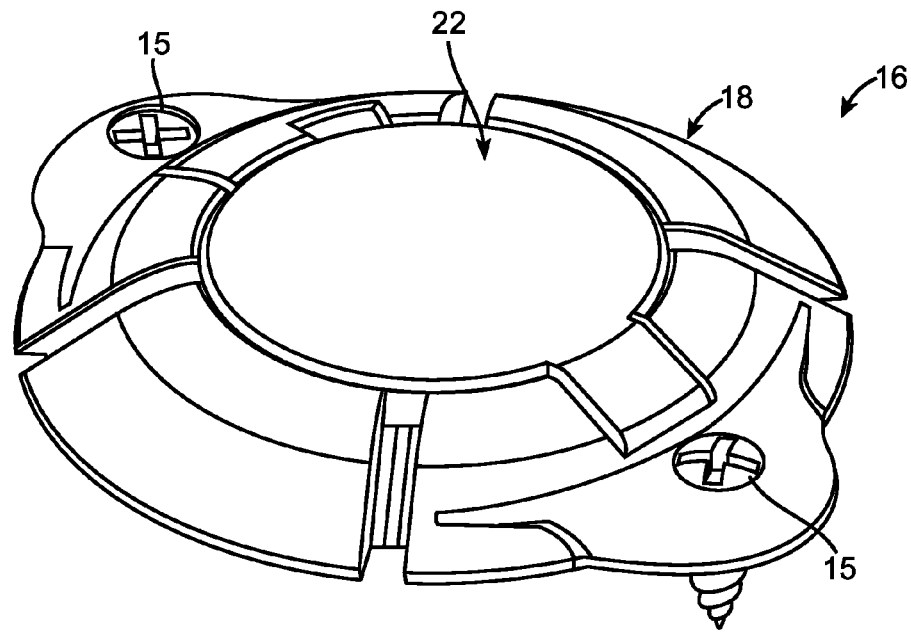
FIG. 3 is top perspective view of the burr hole plug of FIG. 2.
Figure 4:
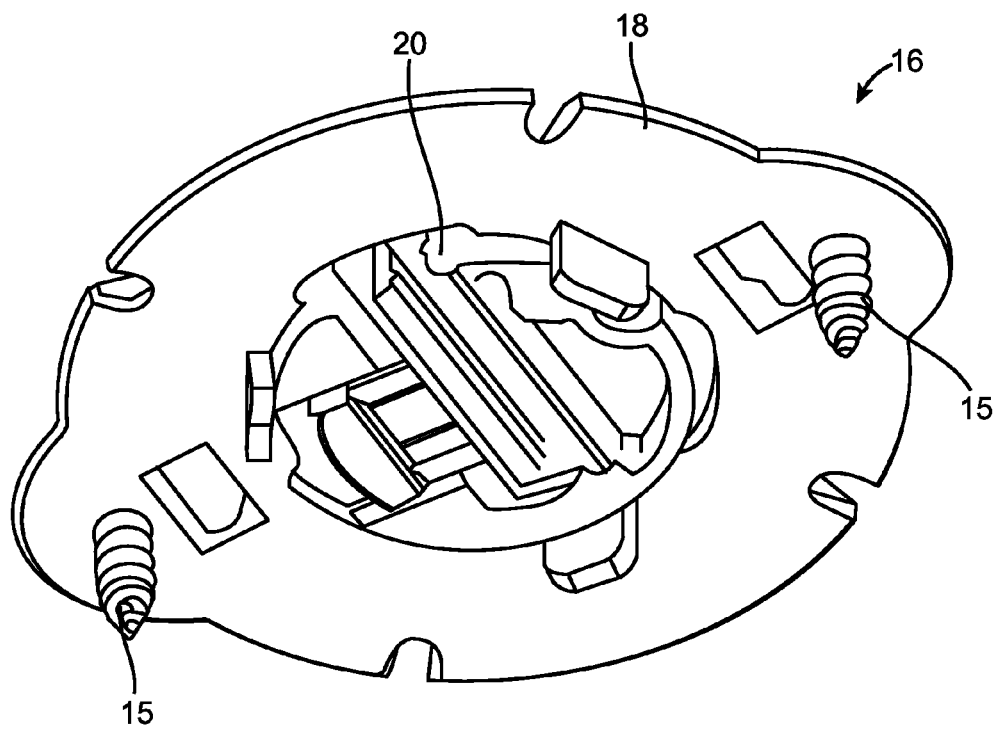
FIG. 4 is a bottom perspective view of the burr hole plug of FIG. 2.
Figure 5:
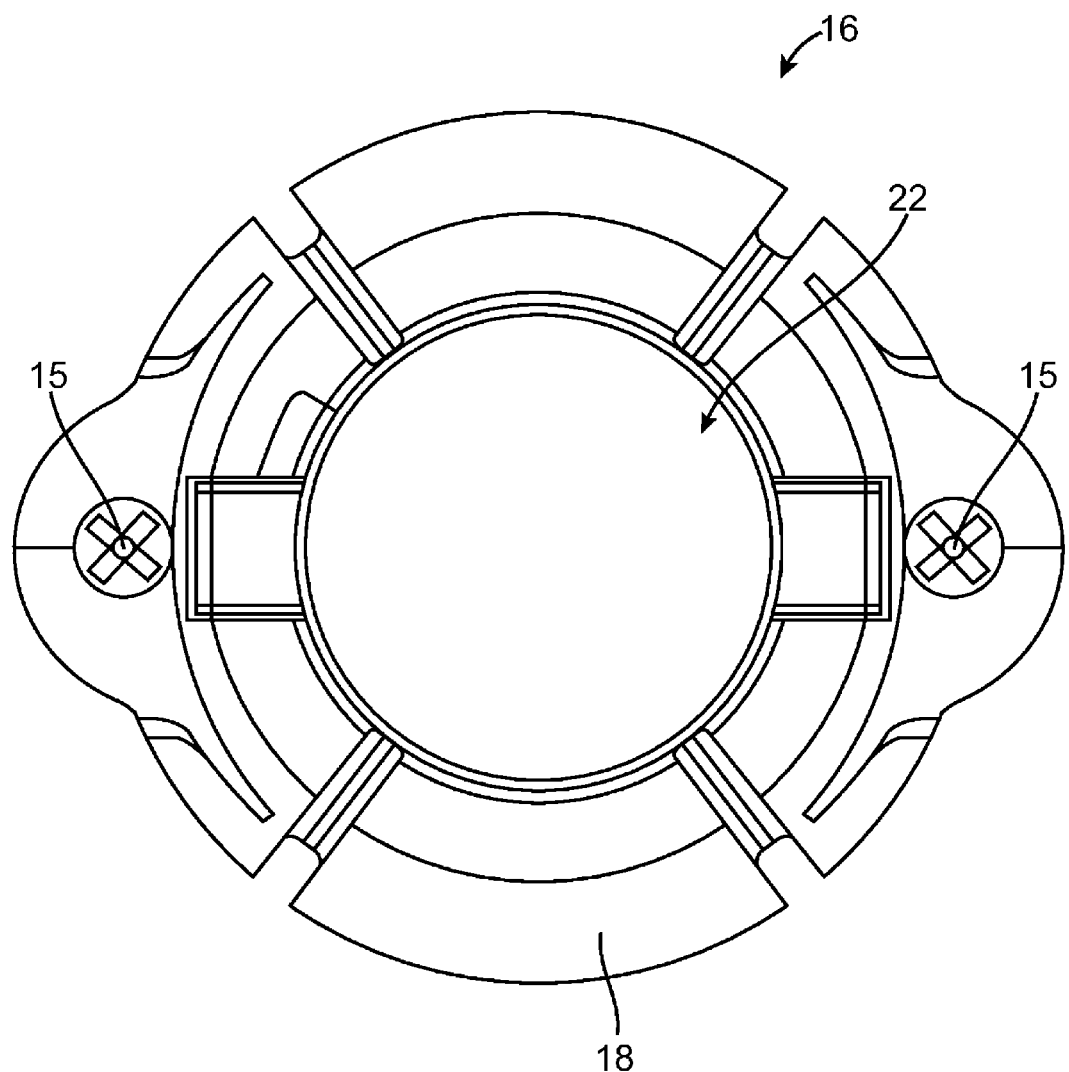
FIG. 5 is a top view of the burr hole plug of FIG. 2.

Turning first to FIG. 1, an exemplary DBS system 10 constructed in accordance with one embodiment of the present inventions is shown implanted within a patient for the treatment of a debilitating disease such as, Parkinson's disease, dystonia, essential tremor, seizure disorders, obesity, depression, etc. The system 10 comprises a stimulation lead 12 implanted within the parenchyma of the brain 2 of a patient 1 in order to position electrodes 14 carried by the distal end of the stimulation lead 12 adjacent a target tissue region 3, such as a deep brain structure of the patient (e.g., the ventrolateral thalamus, internal segment of globus pallidus, substantia nigra pars reticulate, subthalamic nucleus, or external segment of globus pallidus). Thus, electrical stimulation energy can be conveyed from the electrodes 14 to the target tissue region 3 to treat the disease. As can be seen, the stimulation lead 12 is introduced into the head 4 of the patient 1 via a burr hole 5 formed in the cranium 6 of the patient 1. In alternative embodiments, multiple stimulation leads (not shown) may be used, all of which may be located within the head 4 of the patient 1 via the same burr hole 5, as will be described in further detail below.

To secure the stimulation lead 12 (or leads) and to prevent infection and leakage of cerebral spinal fluid, the system 10 further comprises a burr hole plug 16 mounted to the cranium 6 around the burr hole 5 of the patient 1. The stimulation lead 12 extends from the burr hole 5, through the burr hole plug 16, to a location external to the cranium 6. Details discussing the structure and function of various embodiments of the burr hole plug 16 will be discussed in further detail below.

The DBS system 10 further comprises a neurostimulator 17, such as an implantable pulse generator (IPG), radio frequency (RF) receiver-stimulator, or any other device coupled to and capable of delivering electrical stimulation energy to the stimulation lead 12 in a controlled and therapeutic manner. The neurostimulator 17 may be generally implanted in a surgically made pocket in the torso of the patient (e.g., the chest or shoulder region). The neurostimulator 17 may, of course, also be implanted in other locations of the patient's body. The DBS system 10 further comprises a lead extension 19, which may be suitably connected to the proximal end of the stimulation lead 12 and subcutaneously advanced underneath the scalp 7 of the patient 1 to the neurostimulator implantation site, thereby facilitating the location of the neurostimulator 17 away from the exit point of the stimulation lead 12 (i.e., the burr hole 5). In alternative embodiments, the neurostimulator 17 may be directly implanted on or within the cranium 6 of the patient 1, as described in U.S. Pat. No. 6,920,359, which is expressly incorporated herein by reference. In this case, the lead extension 19 may not be needed. After implantation, the neurostimulator 17 is used to provide the therapeutic stimulation under control of the patient 1. The system 10 may include external components, such as a patient handheld programmer, a clinician programming station, and an external charger (all not shown), the details of which will not be described herein for purposes of brevity.

In should be understood that, while the invention lends itself well to applications in DBS, the invention, in its broadest aspects, may not be so limited. For example, the stimulation lead 12 (or leads) can be delivered within regions of the brain other than a deep brain structure, e.g., within or on the surface of the cerebral cortex. In addition, electrical leads, other than stimulation leads, may be delivered within the head 4 of the patient 1. For example, an electrical recording lead can be delivered into the head 4 of the patient 1 via the burr hole 5 to sense brain signals, either alone or in conjunction with a stimulation lead. Further, elongated medical devices other than electrical leads; for example, drug delivery catheters or needles, may be delivered into the head 4 of the patient 1 via the burr hole 5. Thus, it can be appreciated that the burr hole plugs described herein can be used with any elongated medical device intended to be delivered through a burr hole 5 within the cranium 6 of a patient 1 for any therapeutic and/or diagnostic purpose.

Referring now to FIGS. 2-7, one embodiment of a burr hole plug 16 will be described. The burr hole plug 16 generally comprises a plug base (or shell) 18 configured for being fixably mounted about a burr hole, a retainer 20 configured for being mounted within the plug base 18 and for temporarily securing a stimulation lead extending through the burr hole, and a cap 22 configured for being mounted to the plug base 18 over the retainer 20 in order to permanently secure the stimulation lead while sealing the burr hole. The burr hole plug 16 further comprises a plurality of fasteners, and in this case, a pair of screws 14, for mounting the plug base 18 to the cranium 6 of the patient 1.

Figure 6:
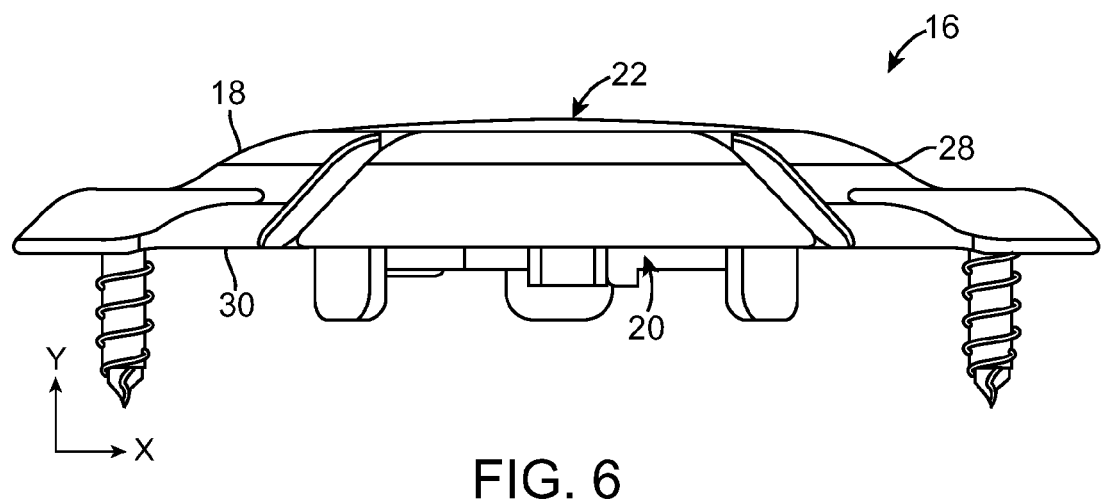
FIG. 6 is a side view of the burr hole plug of FIG. 2.
Figure 8:
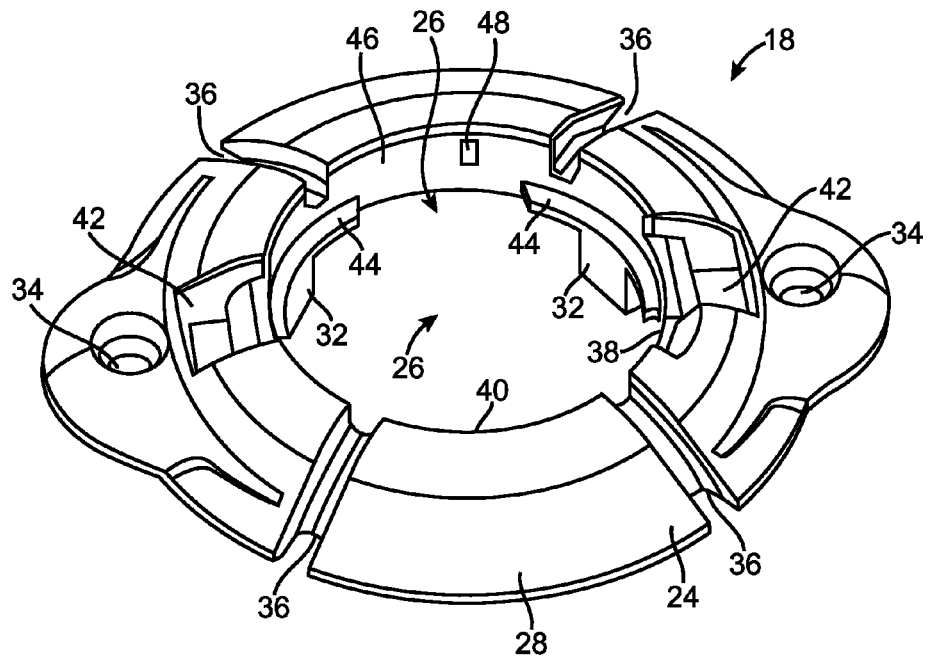
FIG. 8 is a top perspective view of a plug base used in the burr hole plug of FIG. 2.
Figure 9:
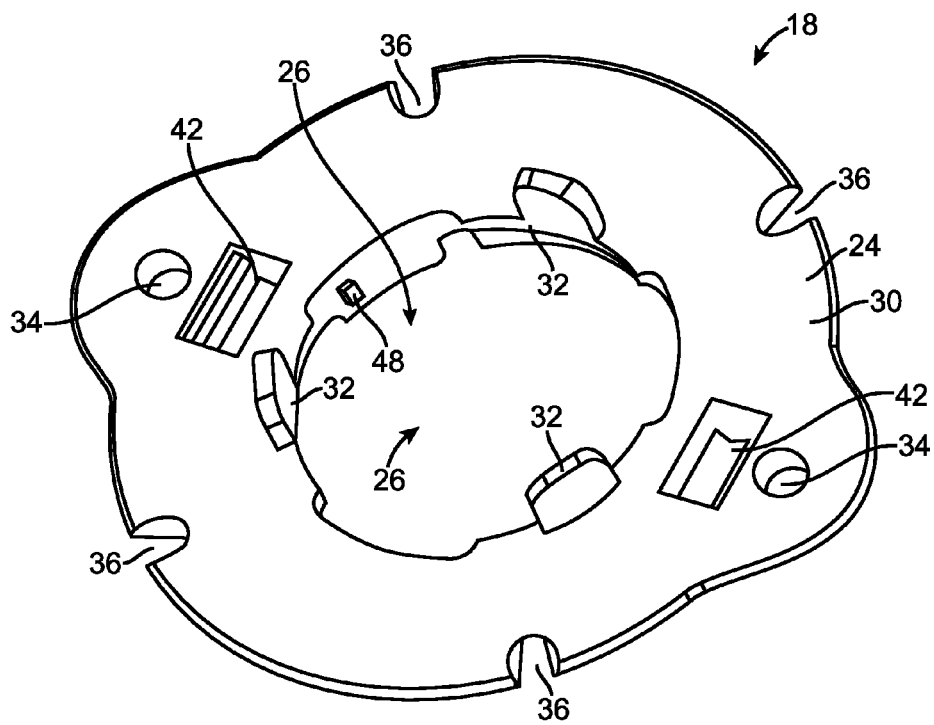
FIG. 9 is a bottom perspective view of the plug base of FIG. 8.
Figure 10:
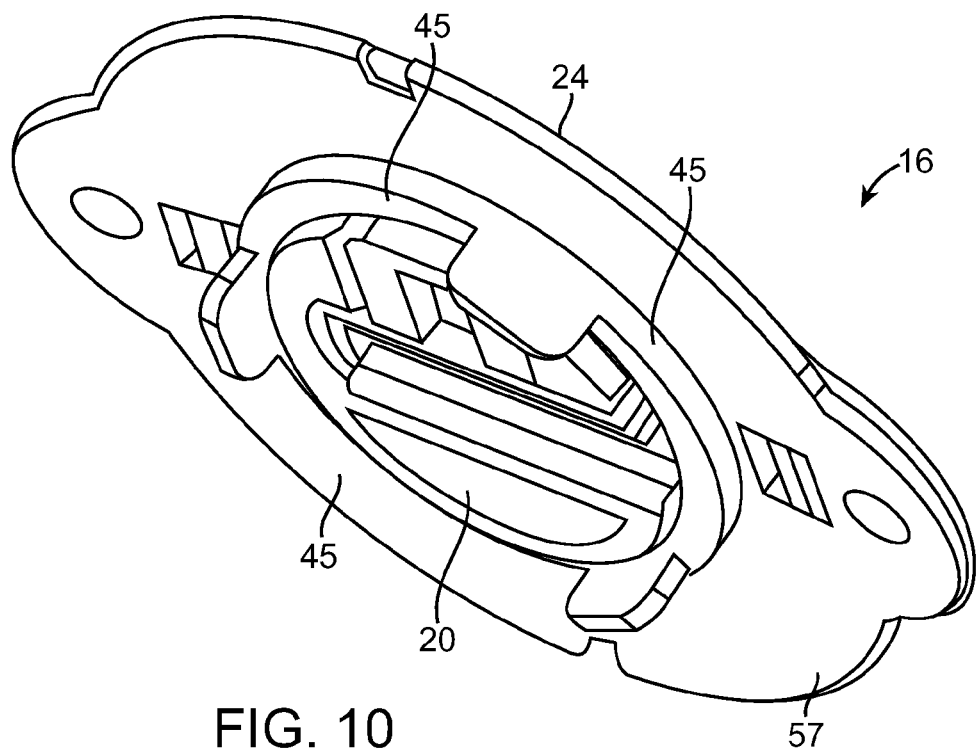
FIG. 10 is a bottom perspective view of a second embodiment of a burr hole plug that can be used in the DBS system of FIG. 1.

Referring further to FIGS. 8 and 9, the plug base 18 includes a closed ring-shaped body 24 and an aperture 26 through which the stimulation lead exiting from the burr hole may pass. The ring-shaped body 24 is composed of a suitable hard biocompatible material, such as titanium, stainless steel, alloys, or hard polymers. The profile of the ring-shaped body 24 is preferably minimized as much as possible, such that the plug base 18 does not noticeably protrude from the cranium underneath the scalp of the patient. As best shown in FIG. 6, the top surface 28 of the ring-shaped body 24 may also be tapered to further reduce the visibility of the burr hole plug 16 below the patient's scalp. The bottom surface 30 of the ring-shaped body 24 may optionally be concave (not shown) in order to match the curvature of a typical cranium. The plug base aperture 26 preferably matches the shape and size of the burr hole. For example, the aperture 26 may have a circular shape and its greatest dimension may be equal to or less than 25 mm. Thus, it can be appreciated that the ring-shaped body 24 can be disposed about the burr hole, such that the aperture 26 is coincident with, and lies directly above, the burr hole.

To ensure that the ring-shaped body 24 is centered relative to the burr hole, the plug base 18 further comprises a plurality of self-centering tabs 32 configured for extending within the burr hole. In the illustrated embodiment, the tabs 32 are disposed on the bottom surface 30 of the ring-shaped body 24, so that the tabs 32 do not obstruct the passage of the stimulation lead through the plug base aperture 26. Notably, because the tabs 32, as opposed to a continuous cylindrical flange, are independently flexible, the plug base 18 can be centered within burr holes that are slightly smaller than the circumference defined by the tabs 32. Thus, the plug base 18 can be used with differently sized burr holes.

The plug base 18 preferably includes at least three tabs 32 equidistantly spaced around the aperture 26 in order to maximize the centering function. The tabs 32 are preferably arranged in a manner such that they fit tightly against the inner surface of the circumference of the burr hole so as to avoid any movement of the plug base 18 relative to the burr hole. In this case, the tabs 32 will be coincident with the plug base aperture 26 (assuming that the aperture 26 is of the same size and shape as the burr hole). The tabs 32 are designed to be permanently disposed on the ring-shaped body 24, such that the tabs 32 will remain located within the burr hole after implantation. The tabs 32 may be suitably disposed onto the ring-shaped body 24, for example, by molding the tabs 32 and body 24 as a unibody design. Significantly, the self-centering tabs 32 conveniently and quickly allow the plug base 18 to be centered relative to the burr hole without the aid of a special centering tool.

In the illustrated embodiment, the plug base 18 is permanently anchored to the cranium of the patient. To this end, the plug base 18 includes two fastening holes 34 formed within the ring-shaped body 24 for respectively receiving anchoring fasteners, such as, e.g., screws, pins, spikes, tabs, or buttons. Alternatively, other means of anchoring the plug base 18 to the cranium of the patient, such as, e.g., adhesion, can be used. Relief structures (not shown) may be added to the bottom surface 30 of the ring-shaped body 24 and the outer surfaces of the tabs 32 to prevent rotational movement between the plug base 18 and the burr hole prior to permanent anchoring to the cranium. Such relief structures may include, e.g., a rough sandpaper-like surface, notches, bumps, horizontal or vertical ribs or threads, etc.

The plug base 18 further comprises a plurality of lead exit grooves 36 (in this case, four equally spaced grooves) configured for seating the stimulation lead. In particular, the portion of the stimulation lead exiting the burr hole through the aperture 26 of the plug base 18 (i.e., the proximal end of the stimulation lead) can be bent down at a perpendicular angle and seated within one of the lead exit grooves 36 of the plug base 18, such that the proximal end of the stimulation lead lies generally parallel to the exterior surface of the cranium. As will be described in further detail below, the stimulation lead will be firmly secured within the selected exit groove 36 when the cap 22 is mounted to the plug base 18.

Figure 11:
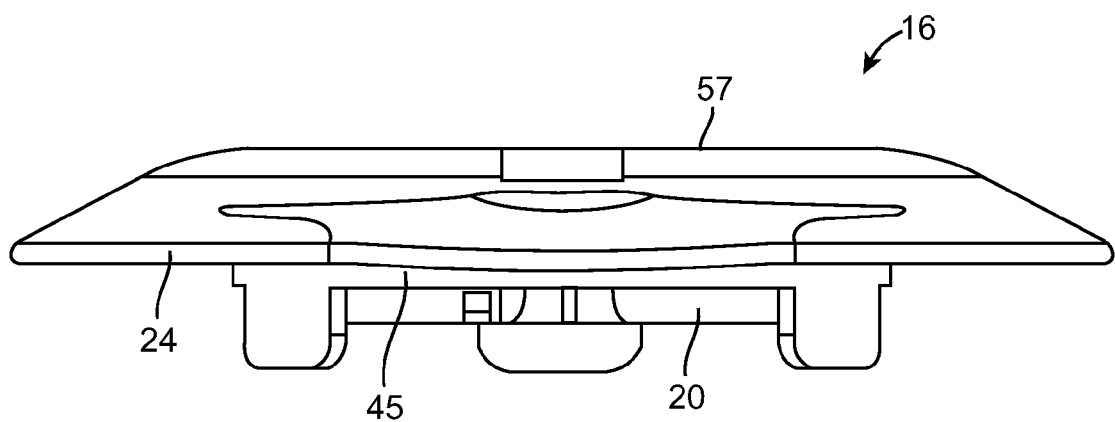
FIG. 11 is a side view of the burr hole plug of FIG. 10.
Figure 12:
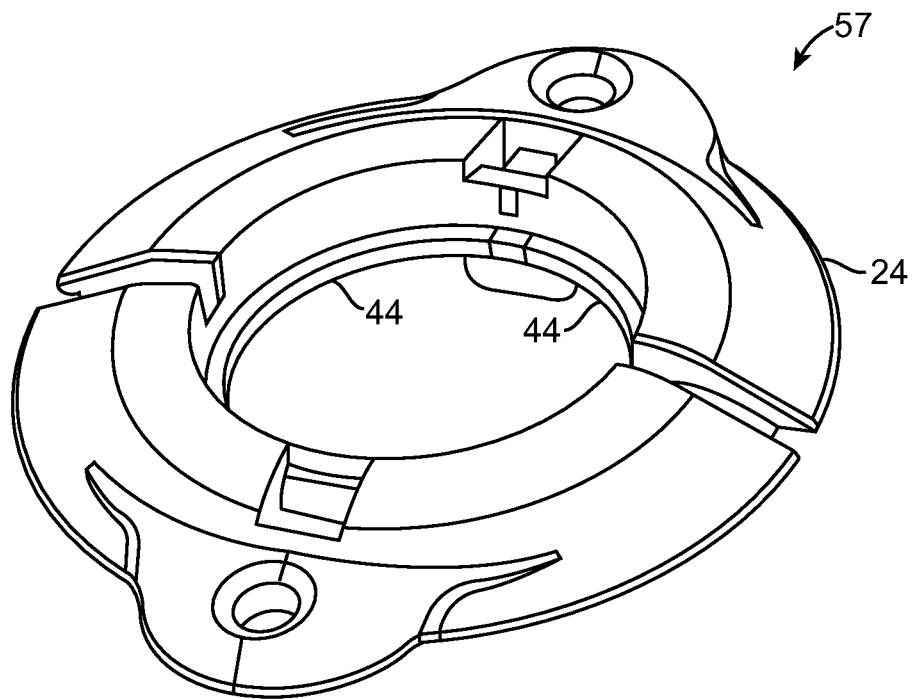
FIG. 12 is a top perspective view of an alternative plug base that can be used in the burr hole plug of FIG. 10.
Figure 13:
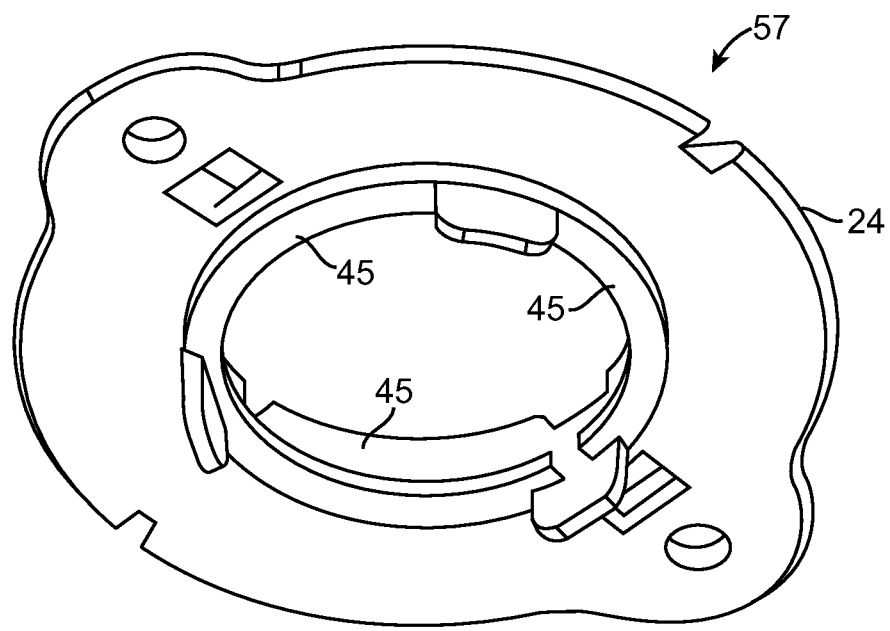
FIG. 13 is a bottom perspective view of the plug base of FIG. 12.

The plug base 18 further comprises a cap pop-out recess 38 located at an inner edge 40 of the ring-shaped body 24 adjacent the aperture 26, and a plurality of cap locking recesses 42 (in this case, a pair of oppositely disposed locking recesses). As will be described in further detail below, a tool can be inserted into the cap pop-out recess 38 to remove the previously mounted cap 22 from the plug base 18, and the cap locking recesses 42 can receive corresponding cap locking tabs (described below) for facilitating mounting of the cap 22 to the plug base 18. The plug base 18 also comprises at least one inner annular ledge 44 (in this case, three equally spaced annular ledges) configured for supporting the retainer 20 when mounted within the plug base aperture 26. To this end, the annular ledges 44 are disposed on an inner surface 46 (best shown in FIG. 14) of the ring-shaped body 24 surrounding the aperture 26, thereby preventing the retainer 20 from descending too far into the burr hole when mounted within the aperture 26. In an alternative embodiment illustrated in FIGS. 10-13, a plug base 57 is similar to the plug base 18, with the exception that it comprises at least one annular flange 45 (in this case, one) extending from the respective annular ledges 44 below the bottom surface 30 of the ring-shaped body 24. Thus, it can be appreciated that the annular flanges 45 allow the top surface of the annular ledges 44 to be flush with the bottom surface 30 of the plug base body 24, so that the retainer 20 can be recessed further down into the burr hole (compare retainer placement in FIG. 11 with FIG. 6).

Figure 14:
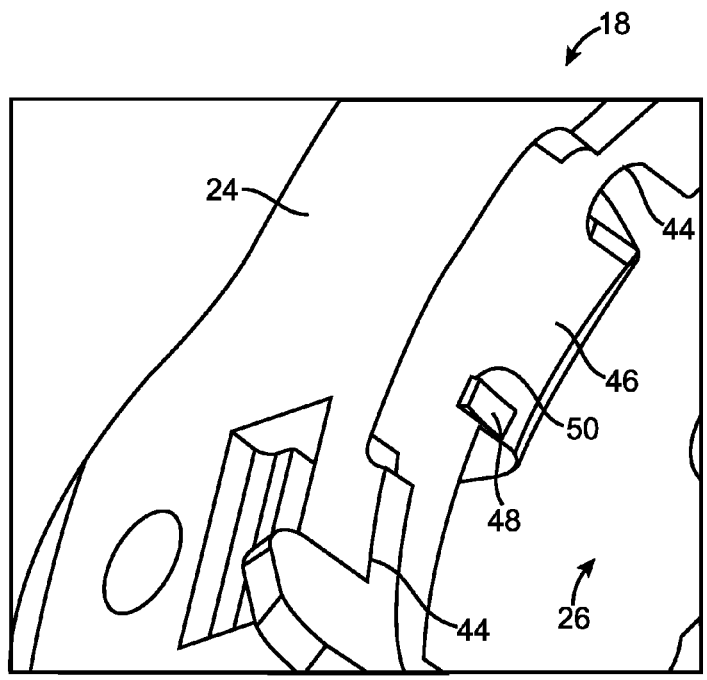
FIG. 14 is a bottom close-up view of the plug base of FIG. 8.
Figure 15:
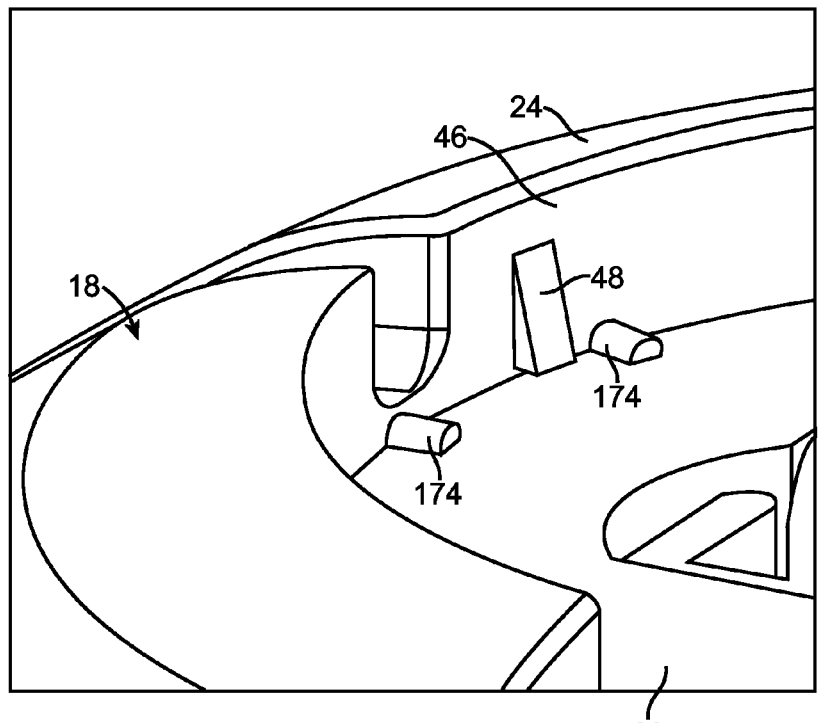
FIG. 15 is a top close-up view of the burr hole plug of FIG. 2.

Referring back to FIGS. 8 and 9, and further to FIGS. 14 and 15, the plug base 18 further comprises a plurality of mechanisms that lock the retainer 20 in place while preventing, or at least hindering, the rotation of the retainer 20 within the plug base aperture 26. In particular, the plug base 18 includes a plurality of ramps 48 (only one shown in FIG. 15) disposed around the inner surface 46 of the ring-shaped body 24 just above the annular ledges 44. The ramps 48 taper inward from top to bottom, such that as the retainer 20 is forced downward into aperture 26, the edges of the retainer 20 slidably engage the ramps 48 and then move past the ramps 48 until the retainer 20 is seated between the annular ledges 44 and bearing surfaces 50 (the bottom surfaces) (best shown in FIG. 14) of the ramps 48, thereby providing an interference fit that locks the retainer 20 within the plug base aperture 26. Preferably, the vertical distance between the bearing surfaces 50 of the ramps 48 and the annular ledges 44 are approximately equal to the thickness of the retainer 20, such that the retainer 20 cannot move up or down within the aperture 26 once it is locked in place. Once the retainer 20 is located between the bearing surfaces 50 of the ramps 48 and the annular ledges 44, the ramps 48 also engage corresponding sun-dial ticks (described below) located on the upper surface of the retainer 20 when the retainer 20 is rotated within the aperture 26, thereby limiting the rotation of the retainer 20, and thus, any inadvertent movement of the stimulation lead, as will be described in further detail below.

Figure 16:
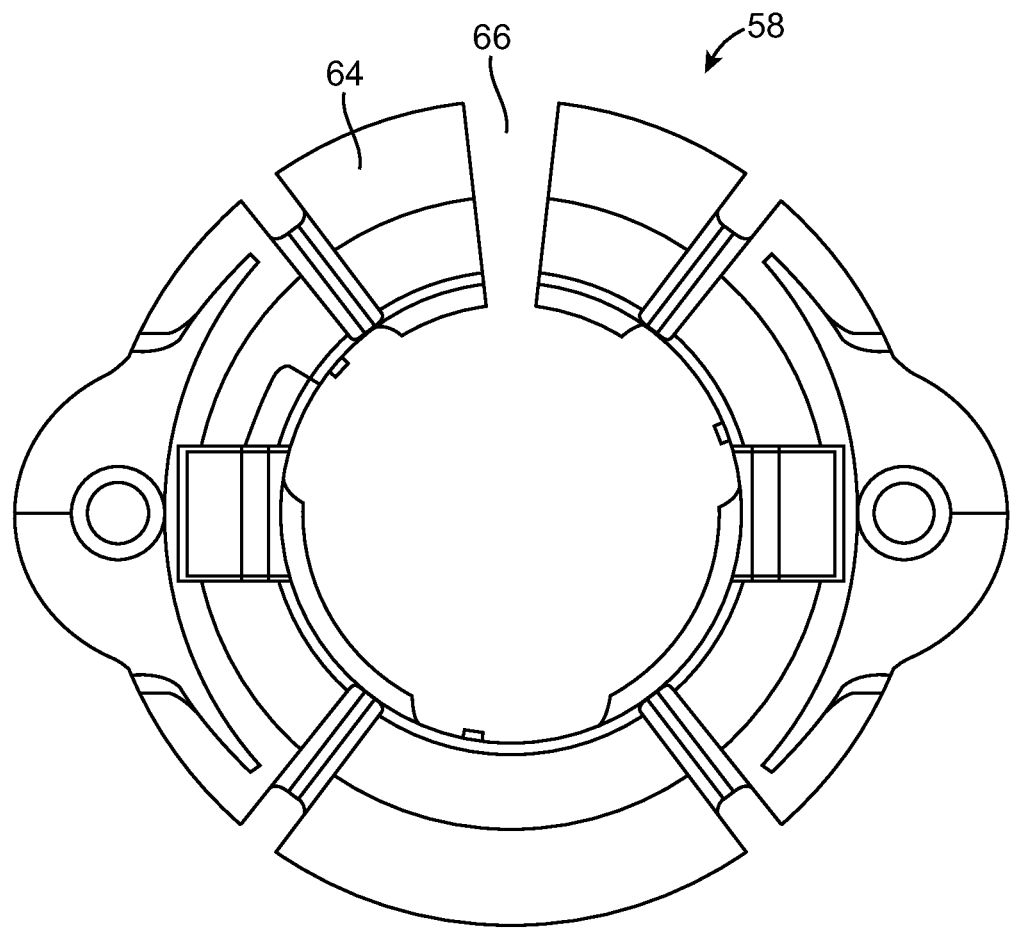
FIG. 16 is a top view of another alternative plug base that can be used in the burr hole plug of FIG. 2.

In the embodiment illustrated in FIGS. 8 and 9, the ring-shaped body 24 is closed, which maximizes the durability of the plug base 18. Alternatively, a slotted plug base 58 may include an open ring-shaped body 64, as illustrated in FIG. 16. In particular, the open ring-shaped body 64 is similar to the closed ring-shaped body 24, with the exception that it comprises an open slot 66 configured for laterally receiving the stimulation lead. This permits the plug base 58 to be mounted to the cranium around the burr hole after the stimulation lead has been inserted through the burr hole and into the brain tissue by simply sliding the stimulation lead through the slot 66 as the plug base 58 is moved into place. Notably, because the open architecture of the ring-shaped body 64 inherently weakens its structure, the ring-shaped body 64 is preferably composed of an extremely durable material, such as, e.g., titanium, thereby overcoming any issues inherently within the open ring-shaped body, such as excessive bending. In one particularly advantageous embodiment, the ring-shaped body 64 is composed of polyethertheterketone (PEEK), which is not only extremely durable and biocompatible, but is also MRI-compatible, and, importantly, will not distort the MRI. Alternatively, the ring-shaped body 64 may be composed of nylon, silicone, Utlem®, Elasthane™ Tecothane®, and/or Bionate®.

Figure 17:
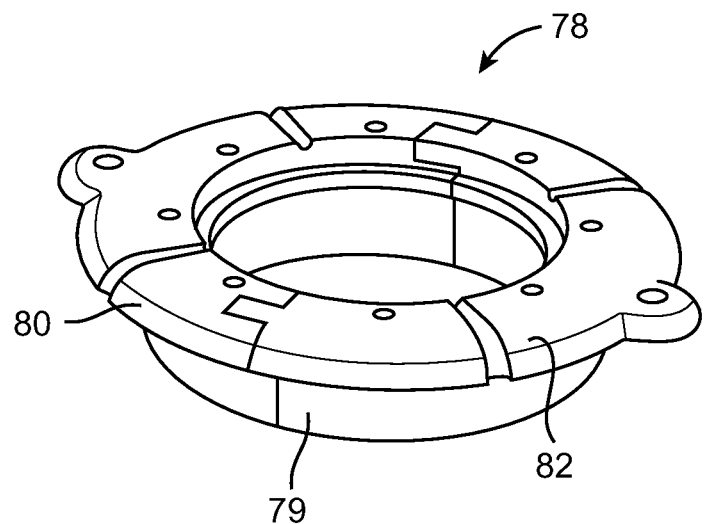
FIG. 17 is top integrated perspective view of still another alternative plug base that can be used in the burr hole plug of FIG. 2.
Figure 18:
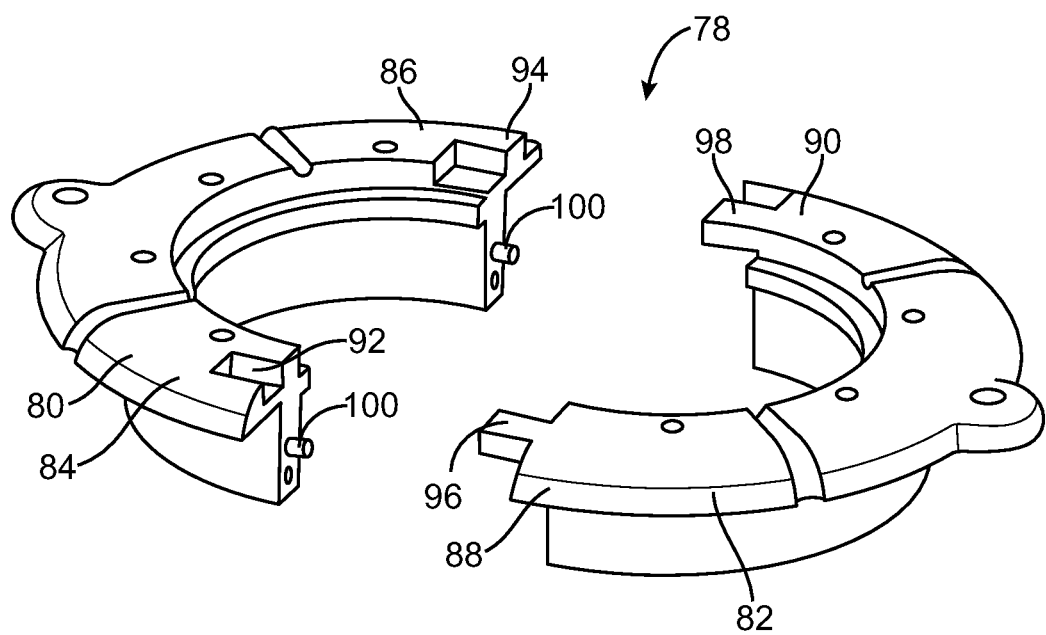
FIG. 18 is a top exploded perspective view of the plug base of FIG. 17

In an alternative embodiment, a split plug base 78 illustrated in FIGS. 17 and 18 may be used. The plug base 78 is similar to the plug base 18 illustrated in FIGS. 8 and 9, with the exception that the plug base 78 comprises a plurality of annular body portions, and in particular, a first annular body portion 80 and a second annular body portion 82, that are configured for being demated from each other to separate the plug base 78 (FIG. 18) and for being mated to each other to integrate the plug base 78 (FIG. 17). The plug base 78 also differs from the plug base 18 in that it comprises a continuous annular flange 79 (instead of self-centering tabs 32) that fits within the cranial burr hole. The plug base 78 is also not shown with a cap pop-out recess 38, cap locking recesses 42, or ramps 48.

In the illustrated embodiment, opposing ends 84, 86 of the first annular body portion 80 respectively include a female coupling element 92 and a male coupling element 94, and opposing ends 88, 90 of the second annular body portion 82 respectively include a male coupling element 96 and a female coupling element 98. The male and female elements 92-98 match each other, such that the ends 84, 88 of the annular body portions 80, 82 can be mated together by receiving the male coupling element 96 of the second annular body portion 82 into the female coupling element 92 of the first annular body portion 80, and the ends 86, 90 of the annular body portions 80, 82 can be mated together by receiving the male coupling element 94 of the first annular body portion 80 into the female coupling element 98 of the second annular body portion 82. Alternatively, both male coupling elements 94, 96 may be located on the opposing ends 84, 86 of the first annular body portion 80, and both female coupling elements 92, 98 may be located on the opposing ends 88, 90 of the second annular body portion 82, or vice versa, with similar results.

In the embodiment illustrated in FIGS. 17 and 18, the male and female coupling elements 92-98 are configured in a manner, such that the annular body portions 80, 82 can be mated together by lowering the second annular body portion 82 down on top of the first annular body portion 80. In particular, the female and male coupling elements 92, 94 of the first annular body portion 80 respectively take the form of a rectangular recess and a rectangular boss located on the upper surface of the first annular body portion 80, and the male and female coupling elements 96, 98 of the second annular body portion 82 respectively take the form of a rectangular protuberance and a C-channel that laterally extend from the upper region of the second annular body portion 82. Thus, when the second annular body portion 82 is lowered onto the first annular body portion 80, the laterally extending protuberance 96 of the second annular body portion 82 will be received by the recess 92 of the first annular body portion 80, and the boss of the first annular body portion 94 will be received by the C-channel 98 of the second annular body portion 82.

Thus, it can be appreciated that the annular body portions 80, 82 can be demated from each other to accommodate a stimulation lead that has already been introduced through a burr hole, and then mated together to integrate the plug base 18, which can then be anchored to the cranium of the patient. It should also be appreciated that, since the plug base 18 is composed of several independent components that can move relative to each other, there is less of a chance of fracturing the plug base 78 when it is anchored to the cranium of the patient.

Even though the plug base 78 is designed to be separated into two pieces, it may still be desirable to alternatively maintain the plug base 78 as a single piece (i.e., as a prior art plug base), for example, when the plug base 18 is to be mounted to the cranium of the patient prior to introducing the stimulation lead through the burr hole. To this end, the plug base 78 comprises additional coupling elements that firmly couple the annular body portions 80, 82 together. In the illustrated embodiment, these coupling elements take the form of complementary pins 100 and recesses (not shown) that firmly engage each other, such that the mated first and second annular body portions 80, 82 act as a unibody design until they are intentionally separated. Once the annular body portions 80, 82 are demated from each other, the pins 100 can be broken off or otherwise removed, so that the second annular body portion 82 can be lowered down on to the first annular body portions 80 when they are mated together without any hindrance from the pins 100. Alternatively, the coupling elements can simply take the form of bonding material or other connection that can be easily fractured to demate the annular body portions 80, 82 from each other.

Figure 18A:
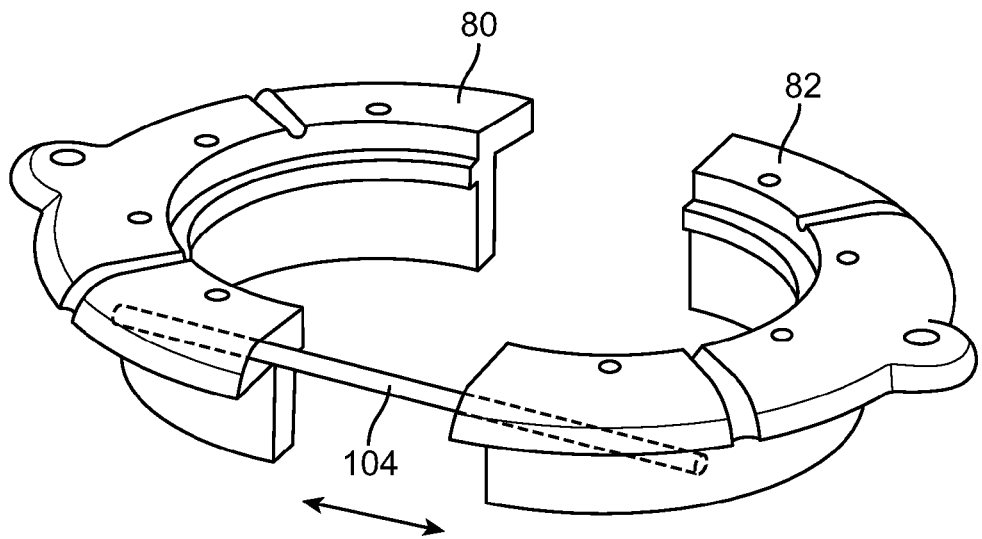
FIGS. 18a and 18b are top perspective views of still other alternative plug bases that can be used in the burr hole plug of FIG. 2.
Figure 18B:
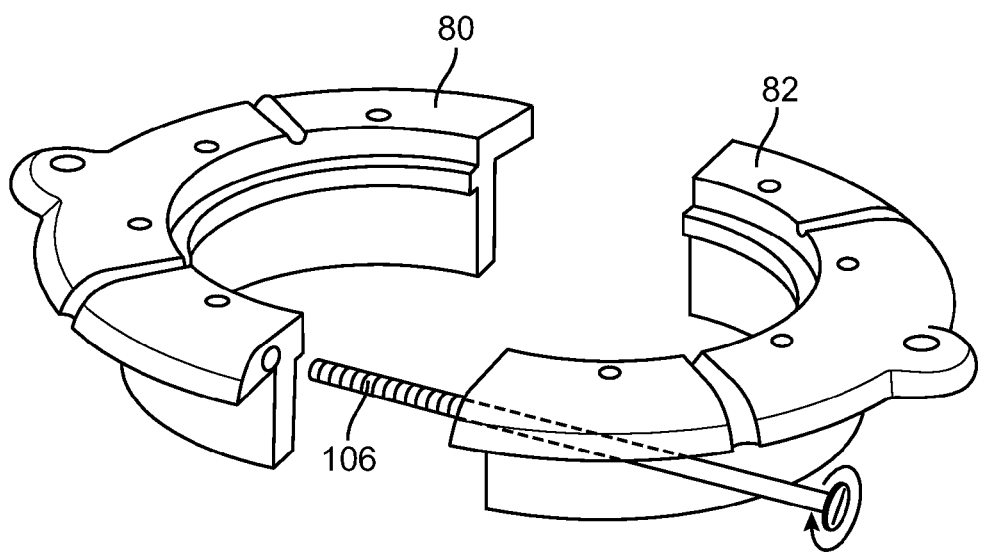

In alternative embodiments, the complementary body portions 80, 82 may be jointed together using a tool. For example, referred to FIG. 18a, the complementary body portions 80, 82 can be integrated together using a rod 104, which allows the body portions 80, 82 to linearly slide together (shown by the double headed arrow). Both body portions 80, 82 may be temporarily jointed to the rod 104, so that the rod 104 can be removed from the body portions 80, 82 after they are mated together. Referring to FIG. 18*b*, the complementary body portions 80, 82 can be integrated together using a threaded member 106, such as a screw, that is rotated in order to gradually force the body portions 80, 82 to linearly slide together.

Figure 19:
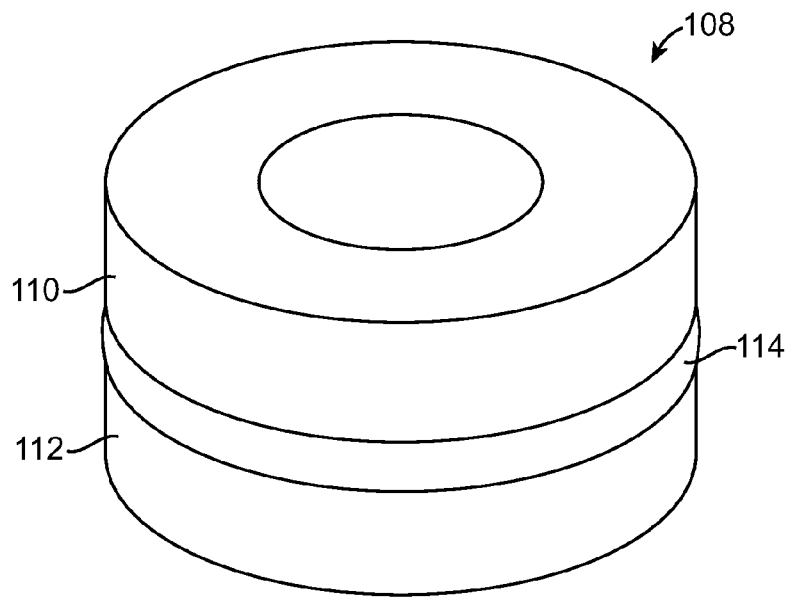
FIG. 19 is a top perspective view of still another alternative embodiment of a plug base that can be used in the burr hole plug of FIG. 2.
Figure 20:
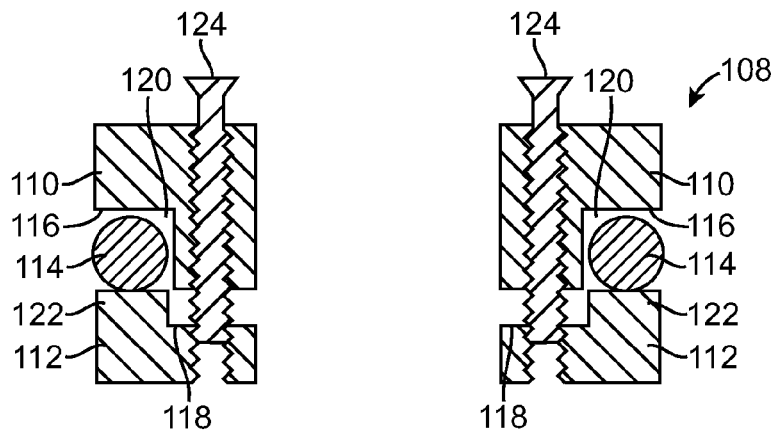
FIGS. 20 and 21 is a cross-sectional view of the plug base of FIG. 19, particularly showing one embodiment of a mechanism for mounting the plug base within a burr hole.
Figure 21:
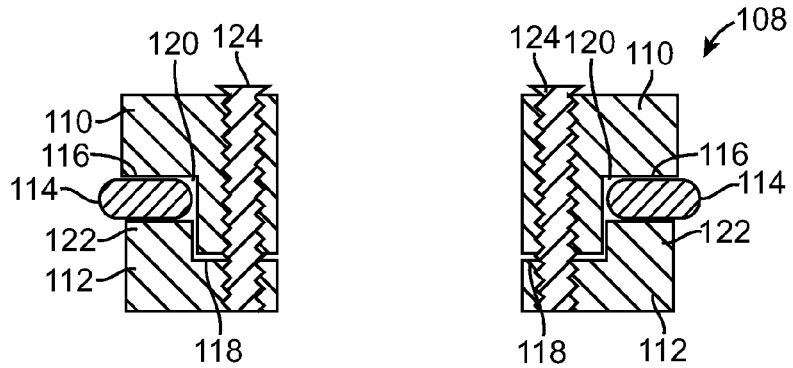

Referring to FIGS. 19-21, another alternative embodiment of a plug base 108 will now be described. Instead of being permanently anchored to the cranium of the patient, the plug base 108 may be reversibly anchored to a burr hole (i.e., it can be anchored without leaving holes other than the burr hole in the cranium), while still providing the benefits of a permanently anchored plug base 18. In particular, the plug base 108 generally comprises an upper ring-shaped plug body 110, a lower ring-shaped plug body 112, and a ring-shaped seal 114 (and in this case, an O-ring) disposed between the plug bodies 110, 112. The seal 114 may be composed of a biocompatible and flexible material, such as, e.g., silicone. The upper ring-shaped plug body 110 has a lower surface 116 with an outer annular recess 120 in which the seal 114 is disposed, and the lower ring-shaped plug body 112 has an upper surface 118 with an outer annular boss 122 on which the seal 114 is disposed. The plug base 108 may have features (not shown) on the upper ring-shaped plug body 110; for example, an annular ledge to support the retainer 20, locking mechanisms to prevent rotation of the retainer 20, or lead exit grooves for seating the stimulation lead.

The outer diameters of the plug bodies 110, 112 are substantially equal to the diameter of the burr hole, such that the plug base 108 can be disposed entirely within the burr hole. The outer diameter of the seal 114, when uncompressed (FIG. 20), is substantially equal to the diameter of the burr hole. When the seal 114 is compressed (FIG. 21) in a vertical direction, which can be accomplished by displacing the plug bodies 110, 112 toward each other, the outer diameter of the seal 114 increases, thereby firmly engaging the surface of the burr hole, such that the burr hole is sealed. To this end, the plug base 108 comprises fasteners, and in particular screws 124, which are disposed within threaded holes 126 formed through the plug bodies 110, 112.

Thus, it can be appreciated that rotation of the screws 124 in one direction using a tool, such as a screwdriver, will cause the plug bodies 110, 112 to be displaced toward each other, which will cause the annular boss 122 of the lower plug body 112 to move into the annular recess 120 of the upper plug body 110 to compress the seal 114 in the vertical direction, thereby expanding the seal 114 in the horizontal direction to sealingly mount the plug base 108 within the burr hole. Rotation of the screws 124 in the opposite direction will cause the plug bodies 110, 112 to be displaced away from each other, which will cause the annular boss 122 of the lower plug body 112 to move out of the annular recess 120 of the upper plug body 110 to allow the seal 114 to expand in the vertical direction, thereby allowing the seal 114 to compress in the horizontal direction to release the plug base 18 from within the burr hole. Although only two screws 124 are shown, more than two screws (e.g., four), can be used to ensure substantially uniform compression of the seal 114 around its circumference.

Figure 22:
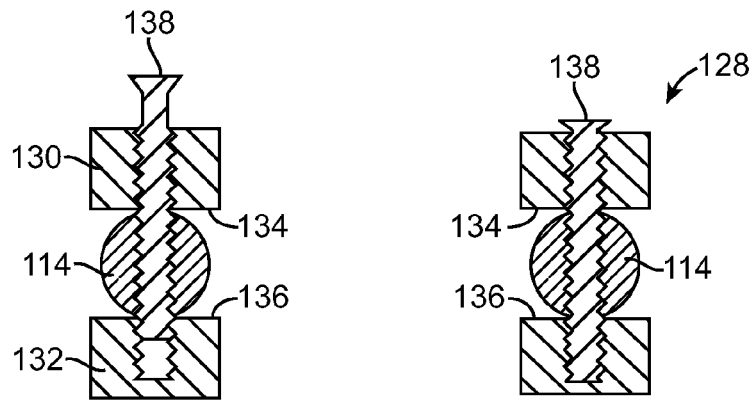
FIGS. 22 and 23 is a cross-sectional view of the plug base of FIG. 19, particularly showing another embodiment of a mechanism for mounting the plug base within a burr hole.
Figure 23:
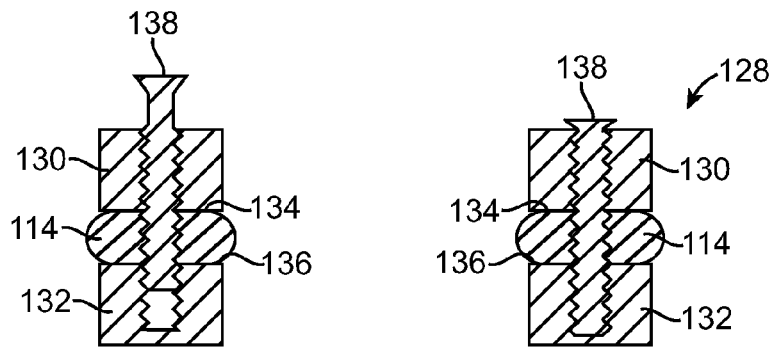

In an alternative embodiment, a plug base 128 illustrated in FIGS. 22 and 23 is similar to the previous plug base 108, with the exception that it comprises upper and lower ring-shaped plug bodies 130, 132 that do not have annular recesses and bosses. Instead, the plug bodies 130, 132 respectively have flat lower and upper surfaces 134, 136 between which the seal 114 disposed. Screws 138 are disposed within threaded holes 140 formed through the plug bodies 130, 132, as well as through the seal 114. Thus, it can be appreciated that rotation of the screws 138 in one direction using a tool, such as a screwdriver, will cause the plug bodies 130, 132 to be displaced toward each other, which will cause the lower and upper surfaces 134, 136 to compress the seal 114 in the vertical direction, thereby expanding the seal 114 in the horizontal direction to sealingly mount the plug base 128 within the burr hole. Rotation of the screws 138 in the opposite direction will cause the plug bodies 130, 132 to be displaced away from each other, to allow the seal 114 to expand in the vertical direction, thereby allowing the seal 114 to compress in the horizontal direction to demount the plug base 128 from within the burr hole.

Figure 24:
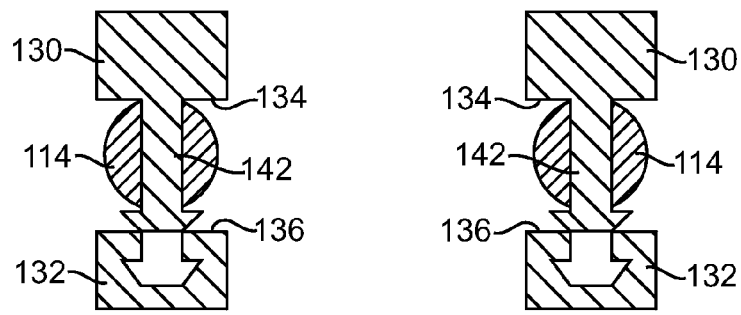
FIGS. 24 and 25 is a cross-sectional view of the plug base of FIG. 19, particularly showing still another embodiment of a mechanism for mounting the plug base within a burr hole.
Figure 25:
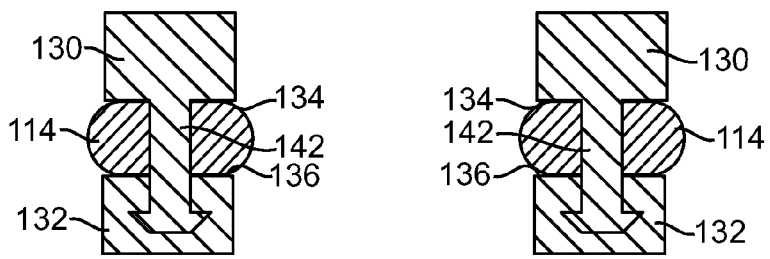

While the fasteners that displace the upper and lower plug bodies to compress the seal have been described as screws, other types of fasteners can be used, such as complementary coupling elements that are fit together in an interference arrangement. For example, as illustrated in FIGS. 24 and 25, flared pins 142 can be disposed on the lower surface 134 of the upper plug body 130, and matching flared recesses 144 can be disposed on the upper surface 136 of the lower plug body 132. Thus, the flared pins 142 can be respectively introduced through holes 146 in the seal 114 and snap-fit into the flared recesses 144, thereby causing the lower and upper surfaces 134, 136 to compress the seal 114 (FIG. 25) in the vertical direction, thereby expanding the seal 114 in the horizontal direction to sealingly mount the plug base 128 within the burr hole. A tool (not shown) can be used to hold the lower plug body 132 in place while the flared pins 142 are snap-fit into the flared recesses 144. The upper plug body 130 can be displaced from the lower plug body 132 to remove the flared pins 142 from the flared recesses 144 to allow the seal 114 to expand (FIG. 24) in the vertical direction, thereby allowing the seal 114 to compress in the horizontal direction to release the plug base 128 from the burr hole.

Figure 26:
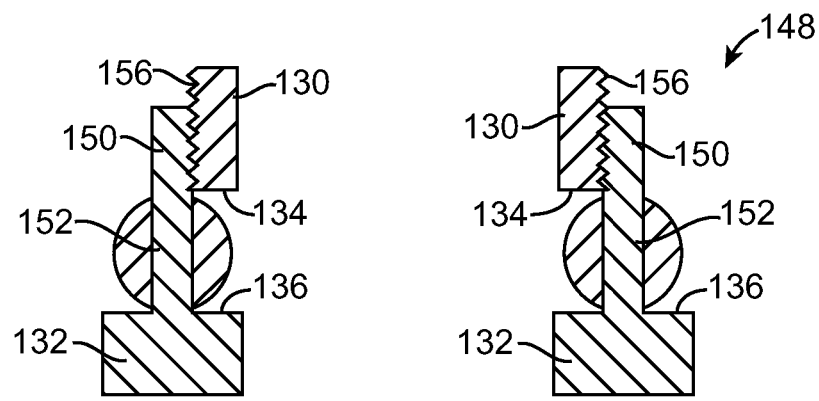
FIGS. 26 and 27 is a cross-sectional view of the plug base of FIG. 19, particularly showing yet another embodiment of a mechanism for mounting the plug base within a burr hole.
Figure 27:
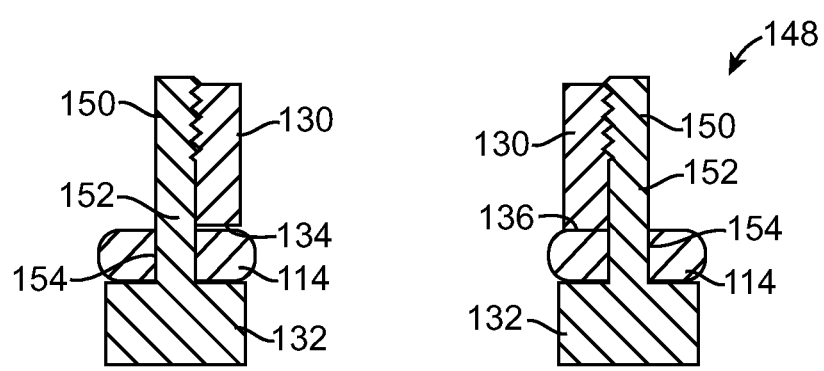
Figure 28:
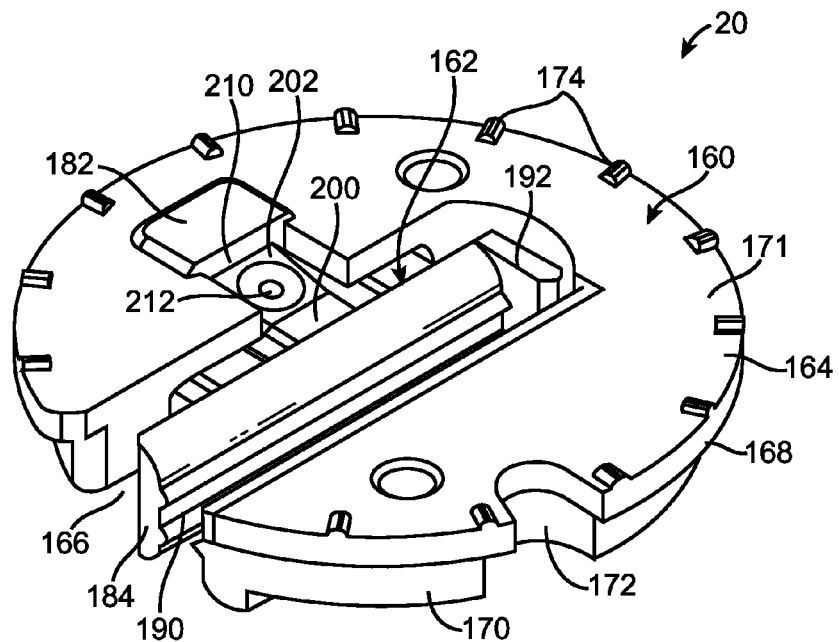
FIG. 28 is a top perspective view of a retainer used in the burr hole plug of FIG. 2.
Figure 29:
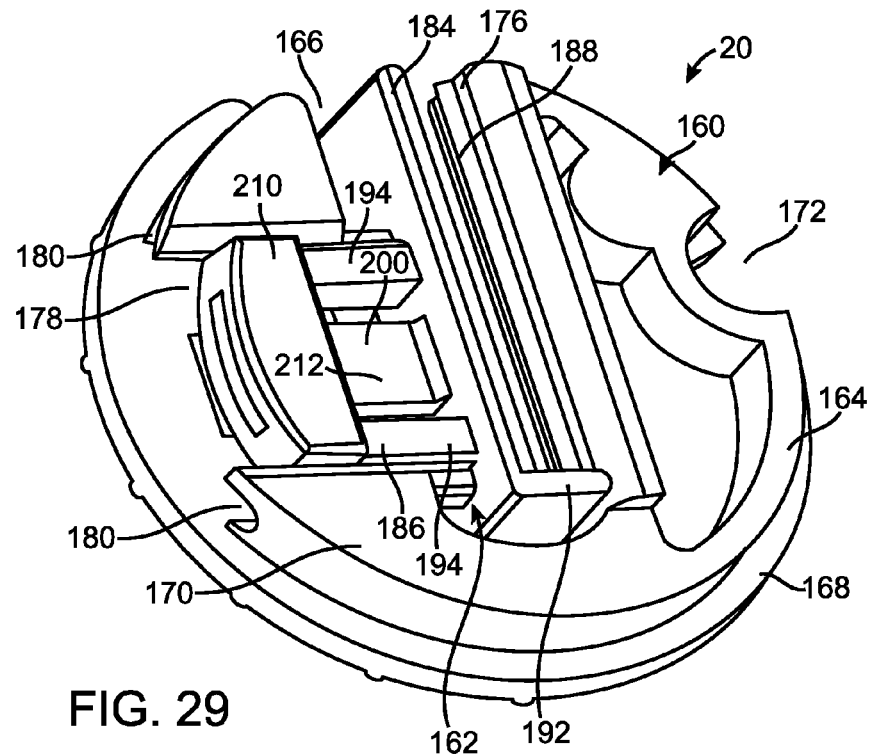
FIG. 29 is a bottom perspective view of the retainer of FIG. 28.
Figure 30:
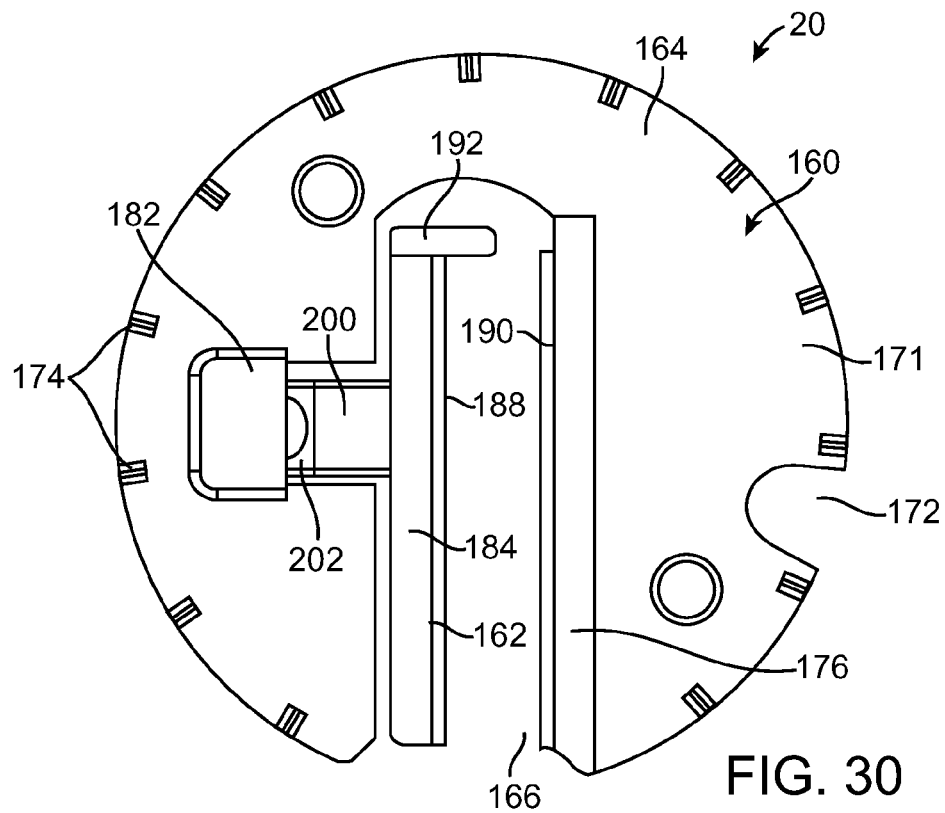
FIG. 30 is a top view of the retainer of FIG. 28, particularly showing the clamping mechanism is an open position.
Figure 31:
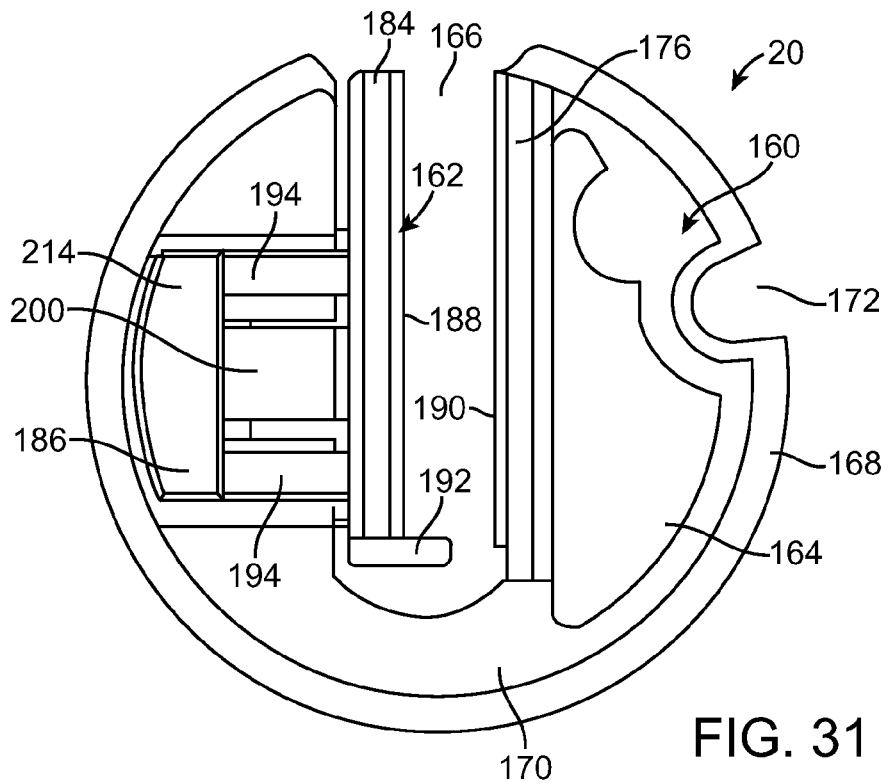
FIG. 31 is a bottom view of the retainer of FIG. 28, particularly showing the clamping mechanism in an open position.
Figure 32:
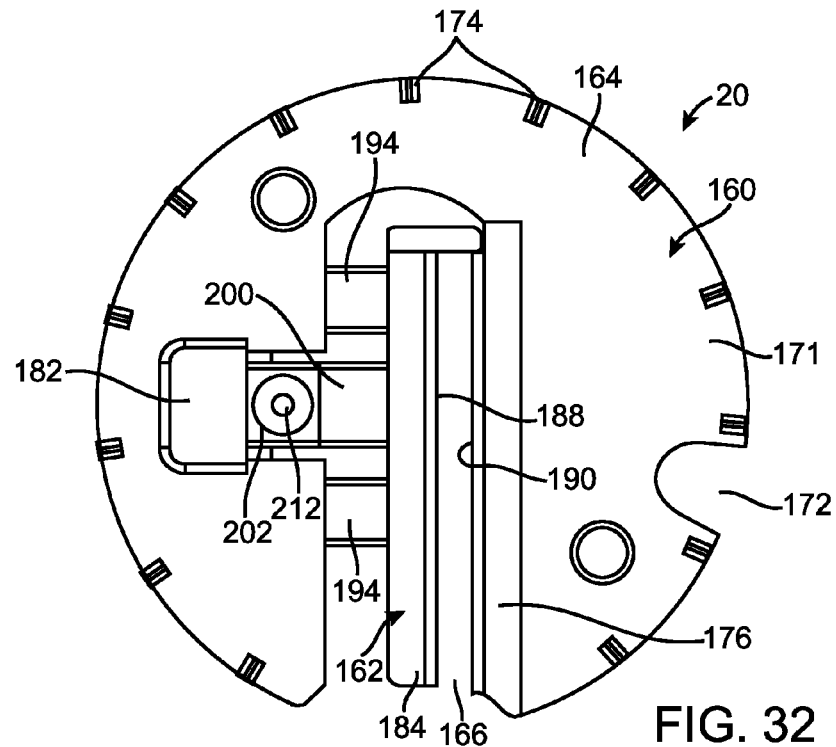
FIG. 32 is a top view of the retainer of FIG. 28, particularly showing the clamping mechanism is a closed position.
Figure 33:
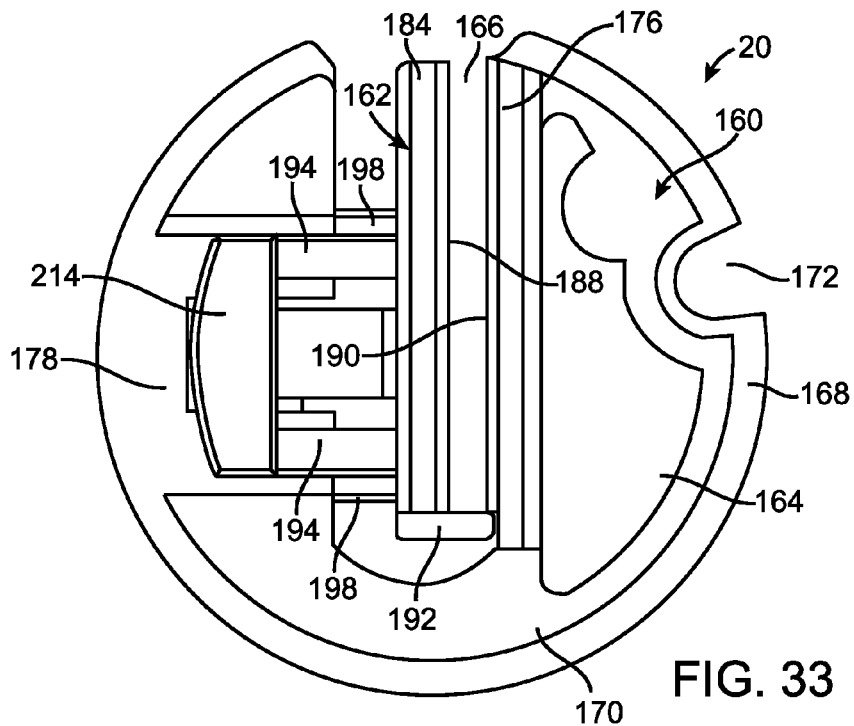
FIG. 33 is a bottom view of the retainer of FIG. 28, particularly showing the clamping mechanism in a closed position.

In another alternative embodiment illustrated in FIGS. 26 and 27, another plug base 148 that can be non-invasively mounted within a burr hole will be described. The plug base 148 is similar to the plug base 108, with the exception that it includes a threaded collar 150 mounted to an upper surface 160 of the lower plug body 132 via standoffs 152 that extend through holes 154 in the seal 114. In this case, the upper plug body 130 includes a threaded outer surface 156 that engages the threaded collar 150 to displace the upper plug body 130 relative to the lower plug body 132. Thus, it can be appreciated that rotation of the upper plug body 130 in one direction will cause the plug bodies 130, 132 to be displaced toward each other, which will cause the lower and upper surfaces 134, 136 to compress the seal 114 (FIG. 27) in the vertical direction, thereby expanding the seal 114 in the horizontal direction to sealingly mount the plug base 148 within the burr hole. Rotation of the upper plug body 130 in the opposite direction will cause the plug bodies 130, 132 to be displaced away from each other, to allow the seal 114 to expand (FIG. 26) in the vertical direction, thereby allowing the seal 114 to compress in the horizontal direction to release the plug base 148 from within the burr hole.

Referring to FIGS. 28-37, the details of the retainer 20 will now be described. The retainer 20 generally comprises a retaining support 160 configured for being mounted within the plug base aperture 26, and a clamping mechanism 162 mounted to the retaining support 160 and configured for applying a clamping force to the stimulation lead. The clamping force applied to the stimulation lead secures the stimulation lead before and while the cap 22 is being mounted to the plug base 18 to more firmly secure the stimulation lead. The components of the retainer 20 may be composed of the same material as the plug base 18 described above; namely, a suitable hard biocompatible material, such as titanium, stainless steel, alloys, or hard polymers. Alternatively, the components of the retainer 20 may be composed of PEEK to provide certain structural advantages, as will be described in further detail below.

Figure 7:
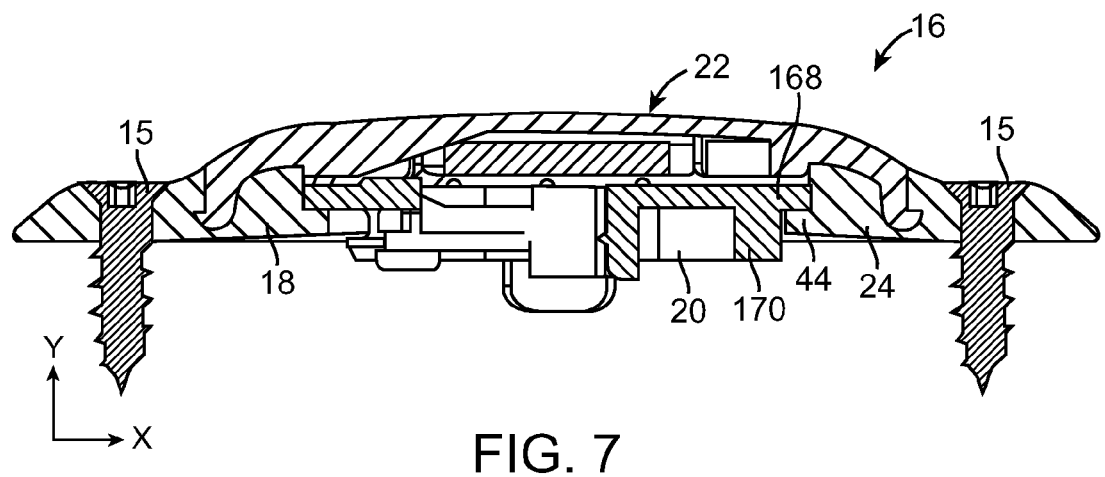
FIG. 7 is a cross-sectional view of the burr hole plug of FIG. 2.

In the illustrated embodiment, the retaining support 160 comprises a disk 164 and an open lead slot 166 formed in the disk 164 for laterally receiving the stimulation lead, thereby allowing the retainer 20 to be mounted within the plug base aperture 26 after the stimulation lead has been introduced through the burr hole. As best shown in FIGS. 7 and 15, the retainer 20, and in particular, the disk 164, can be interference fit between the ramps 48 and the annular ledges 44 located on the inner surface 46 of the ring-shaped body 24. In the illustrated embodiment, the disk 164 has an annular lip 168 disposed around its circumference that is interference fit between the ramps 48 and the annular ledges 44 of the ring-shaped body 24, and a thicker center portion 170 that extends below the annular ledges 44 in order to accommodate the clamping mechanism 162 in a robust manner.

The annular ledges 44 are displaced from the top surface of the plug base 18 a dimension that causes at least a portion of the retainer 20, and in particular the disk 164, below the bottom surface 30 of the ring-shaped plug body 24. As a result, at least a portion of the disk 164 will be recessed within the burr hole when mounted within the plug base 18, thereby lowering the profile of the portion of the burr plug 16 above the burr hole. In the case where annular flanges 45 are provided, as illustrated in FIGS. 10-13, the disk 164 will be further recessed within the burr hole. The retainer 20 is configured for being removably mounted within the plug base aperture 26. To this end, the retainer support 160 further comprises a retainer pop-out notch 172 located on the circumference of the disk 164. The pop-out notch 172 can receive a tool that can be manipulated to pop the retainer 20 out of the plug base 18 (i.e., by overcoming the interference fit between the ramps 48 and annular ledges 44 of the plug base 18). Alternatively, there can simply be a hole a, hook, or an eyelet in or on the disk for receiving a tool to pop the retainer 20 out of the plug base 18.

As discussed above, the retainer 20, and in particular the retainer support 160 comprises a plurality of sun-dial ticks 174 that engage the ramps 48, thereby limiting rotation of the retainer 20 within the plug base aperture 26. In this case, the sun-dial ticks 174 take the form of radially extending ribs that are distributed about the circumference on the top surface 171 of the disk 164. Notably, as the circumferential distance between the sun-dial ticks 174 decreases, the rotational movement of the retainer 20 within the aperture 26 of the plug body 24 will be incrementally decreased to the same extent. In this illustrated embodiment, the circumferential spacing between the sun-dial ticks 174 is approximately 24 degrees, and therefore, the rotation of the retainer 20 will be limited to 24 degrees.

Figure 34:
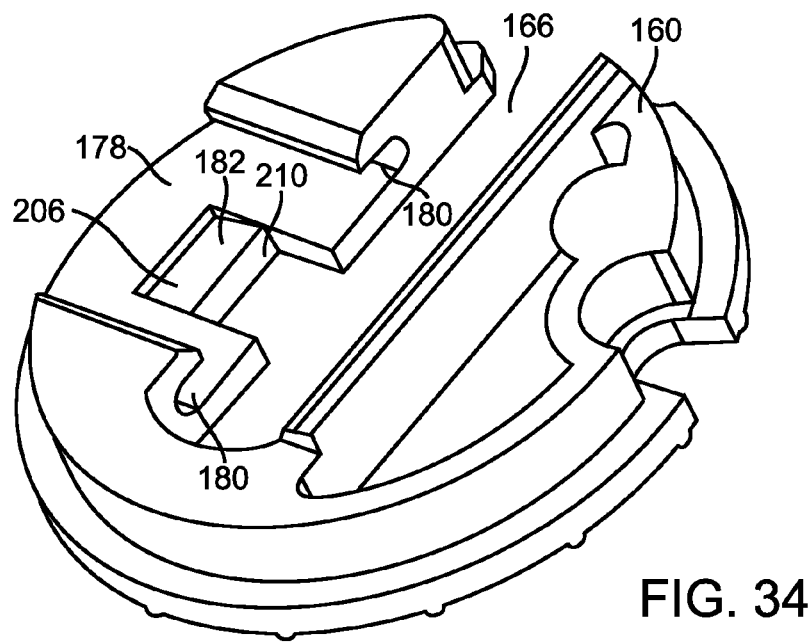
FIG. 34 is a bottom perspective view of a retainer support used in the retainer of FIG. 28.

The retainer support 160 comprises a fixed clamping bar 176 disposed on an inner edge of the disk 164 adjacent one side of the lead slot 166. The clamping mechanism 162 operates in conjunction with the fixed clamping bar 176 to secure the stimulation lead therebetween, as will be described in further detail below. As best shown in FIG. 34, retainer support 160 further comprises a recess 178 formed in the disk 164 and a pair of C-channels 180 on opposite sides of the recess 178 to accommodate the clamping mechanism 162, and a recessed stop 182 within the recess 178 for accommodating a locking element of the clamping mechanism 162, as will be described below. The disk 164 may optionally have a "living hinge" that allows it to be bent along the lead slot 166, thereby facilitating insertion of the clamping mechanism 162 into the disk 164 during assembly.

The clamping mechanism 162 comprises a movable clamping bar 184 and a flange 186 slidably engaged with the disk 164 to laterally slide the movable clamping bar 184 relative to the disk 164 and selectively secure the stimulation lead received within the lead slot 166 or release the stimulation lead received within the lead slot 166. The movable clamping bar 184 extends parallel to the lead slot 166 opposite to the fixed clamping bar 176 on the disk 164, such that a clamping surface 188 of the movable clamping bar 184 is configured for clamping the stimulation lead against a clamping surface 190 of the clamping bar 176. In the illustrated embodiment, the clamping surfaces 188, 190 of the respective clamping bar 184 and clamping bar 176 are ribbed in order to provide localized gripping of the stimulation lead, thereby increasing the lead retention force. The clamping mechanism 162 further comprises an angled flange 192 located at the end of the movable clamping bar 184, thereby preventing the stimulation lead from being located past the movable clamping bar 184 at the end of the slot 166 where it could potentially be wedged between the clamping mechanism 162 and the end of the slot 166.

In the illustrated embodiment, the flange 186 is U-shaped and includes a pair of legs 194 extending perpendicularly from the movable clamping bar 184 away from the lead slot 166 and a cross bar 196 that extends between the legs 194 in a direction generally parallel to the lead slot 166. The U-shaped flange 186 further comprises rails 198 that extend along the outer surface of the legs 194. The sliding arrangement between the flange 186 of the clamping mechanism 162 and the disk 164 of the retainer support 160 is provided between the legs 194 of the U-shaped flange 186 and the C-channels 180 of the retainer support 160. In particular, the U-shaped flange 186 is received within the recess 178, with the rails 198 of the flange 186 slidably received within the C-channels 180 in a closely toleranced relationship, so that the flange 186, and thus the movable clamping bar 184, can be smoothly moved back and forth in a lateral direction (i.e., perpendicular to the lead slot 166).

The clamping mechanism 162 is configured for being placed between an unlocked (or open) position (FIGS. 30-31 and 38) wherein the clamping mechanism 162 can be freely slid relative to the disk 164, and a locked (or closed) position (FIGS. 32-33 and 37) wherein the clamping mechanism 162 cannot be freely slid relative to the retainer support 160 without additional manipulation of the clamping mechanism 162. To this end, the clamping mechanism 162 further comprises a resilient arm 200 extending perpendicularly from the movable clamping bar 184 between the legs 194 of the U-shaped flange 186, and a locking element, and in particular, a tab 202 located at the end of the resilient arm 200. The locking tab 202 is configured for engaging a complementary locking element, and in particular, the recessed stop 182 on the disk 164 to lock the movable clamping bar 184 relative to the disk 164 when the stimulation lead is secured. In particular, as best shown in FIGS. 34-38, the locking tab 202 includes a bearing surface 204 configured for sliding along a bearing surface 206 of the recessed stop 182 when the clamping mechanism 162 is in the unlocked position, and an abutment surface 208 that abuts an abutment surface 210 of the recessed stop 182 when the clamping mechanism 162 in the locked position. The resiliency of the arm 200 on which the locking tab 202 is disposed will naturally cause the locking tab 202 to transition from the bearing surface 204 of the recessed stop 182 to the abutment surface 208 of the recessed stop 182 when the locking tab 202 reaches the end of the recessed stop 182.

Figure 39A:
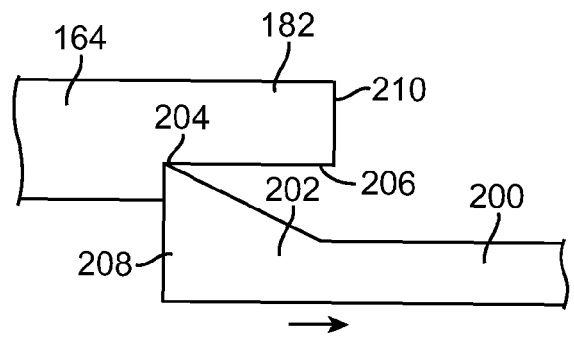
FIGS. 39A-39E are plan views showing the technique in which the clamping mechanism and retainer support of the retainer of FIG. 28 interact to lock and unlock the clamping mechanism from the retainer support.
Figure 39B:
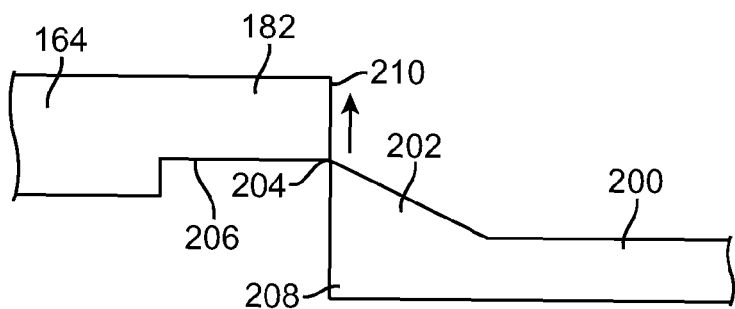
Figure 39C:
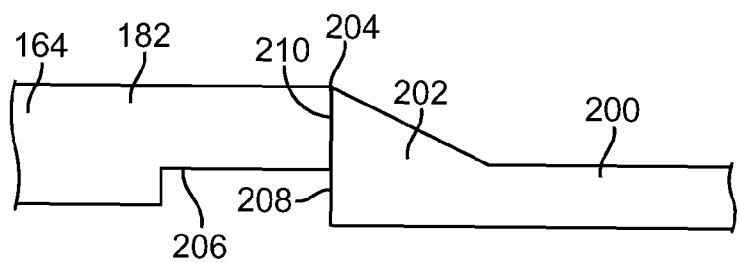

Thus, the clamping mechanism 162 can be placed from the unlocked position (or open position) (FIG. 39A) to the locked position (FIG. 39C) by sliding the U-shaped flange 186, and thus, the movable clamping bar 184, relative to the disk 164 towards the fixed clamping bar 176 as the bearing surface 204 of the locking tab 202 slides along the bearing surface 206 of the recessed stop 182 until the locking tab 202 reaches the end of the recessed stop 182 (FIG. 39B), after which the resiliency of the arm 200 will cause the abutment surface 208 of the locking tab 202 to abut the abutment surface 210 of the recessed stop 182 (FIG. 39C).

Figure 39D:
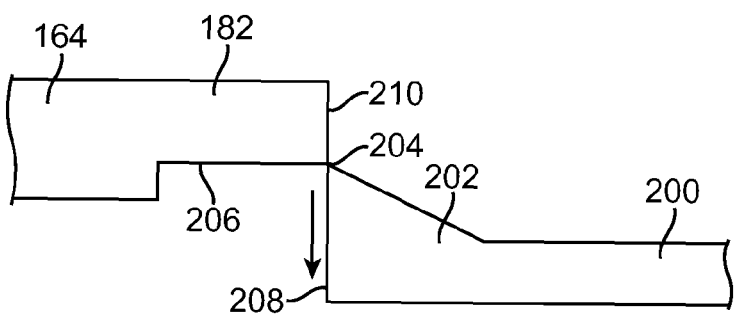
Figure 39E:
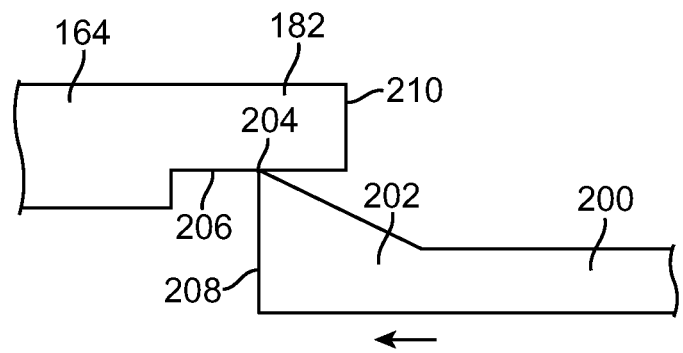

The clamping mechanism 162 can be placed from the locked position (FIG. 39C) to the unlocked position by applying a downward force on the resilient arm 200 to disengage the abutment surfaces 208, 210 of the respective locking tab 202 and recessed stop 182 from each other (FIG. 39D), and sliding the U-shaped flange 186, and thus, the movable clamping bar 184, relative to the disk 164 away from the fixed clamping bar 176 until the bearing surface 204 of the locking tab 202 slides along the bearing surface 206 of the recessed stop 182 (FIG. 39E).

Significantly, the relative dimensions between the resilient arm 200, locking tab 202, and recess stop 182 are selected, such that the abutment surface 208 of the locking tab 202 becomes coincident with the abutment surface 210 of the recessed stop 182 as the stimulation lead becomes secured between the clamping surface 188 of the movable clamping bar 184 and the clamping surface 190 of the fixed clamping bar 176. In the manner, firm clamping of the stimulation lead is ensured without damaging the stimulation lead.

To facilitate manipulation of the clamping mechanism 162 relative to the disk 164, the clamping mechanism 162 comprises a recess 212 formed on the bearing surface 204 of the locking tab 202 for receiving a tool that can be used to flex the resilient arm 200 in order to transition the clamping mechanism 162 from the locked position into the unlocked position. The tool can also be received within the recess 212 to slide the movable clamping bar 184 towards or away from the fixed clamping bar 176 to secure or release the stimulation lead. It should be noted that the recess 212 is closer to the center of the disk 164 than the circumference of the disk 164. Thus, when a downward force applied to the recess 212, any force applied to the circumference of the disk 164, which may otherwise disengage, or weaken the engagement between, the sun-dial ticks 174 on the top surface 171 of the disk 164 from the ramps 48 on the inner surface 46 of the ring-shaped plug body 24, will be minimized or decreased.

Figure 35:
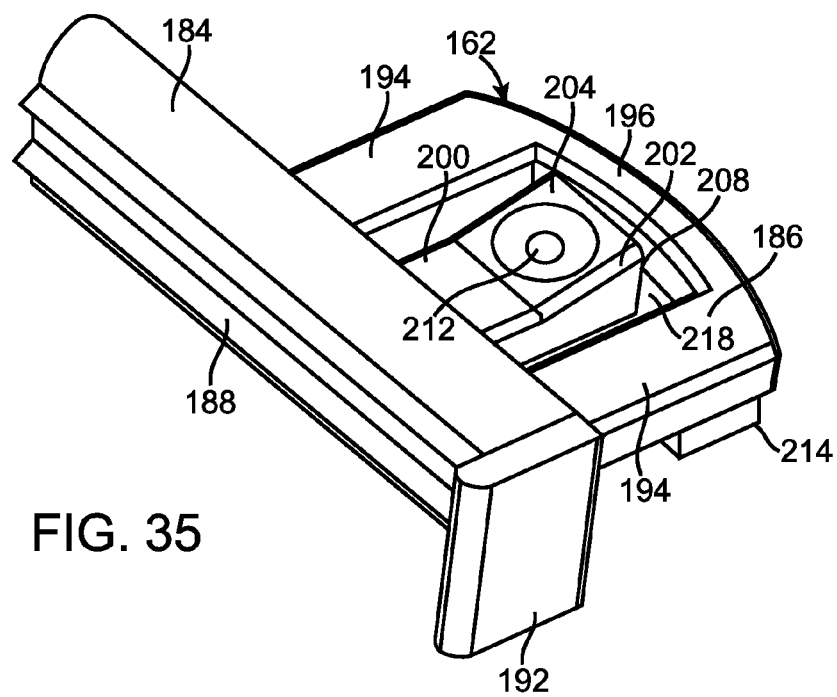
FIG. 35 is a top perspective view of a clamping mechanism used in the retainer of FIG. 28.
Figure 40:
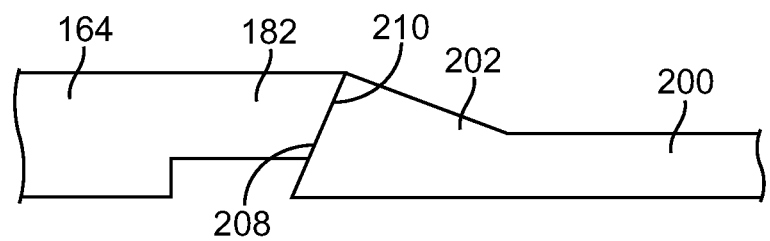
FIG. 40 is a plan view showing an alternative technique in which the clamping mechanism and retainer support of the retainer of FIG. 28 interact to lock and unlock the clamping mechanism from the retainer support.

To further facilitate placing the clamping mechanism 162 from the locked position into the unlocked position, the bearing surface 204 of the locking tab 202, and thus, the recess 212, may be angled (as best shown in FIG. 35) relative to the plane of the disk 164, such that a portion of the downward force applied to the recess 212 by the tool is transferred in a direction away from the slot 166 along the plane of the disk 164. In this manner, as the flexible arm 200 is flexed, the bearing surface 204 of the locking tab 202 will naturally slide along the bearing surface 206 of the recessed stop 182 once the abutment surfaces 208, 210 of the respective locking tab 202 and recessed stop 182 are disengaged from each other. In the embodiment illustrated in FIGS. 39A-39E, the abutment surfaces 208, 210 of the locking tab 202 and recessed stop 182 are perpendicular relative to the plane of the disk 164, thereby maximizing locking engagement of the clamping mechanism 162. However, in an alternative embodiment illustrated in FIG. 40, the abutment surfaces 208, 210 of the locking tab 202 and recessed stop 182 are tapered (i.e., obliquely angled) relative to the plane of the disk 164, thereby facilitating the placement of the clamping mechanism 162 from the locked position into the unlocked position.

Figure 36:
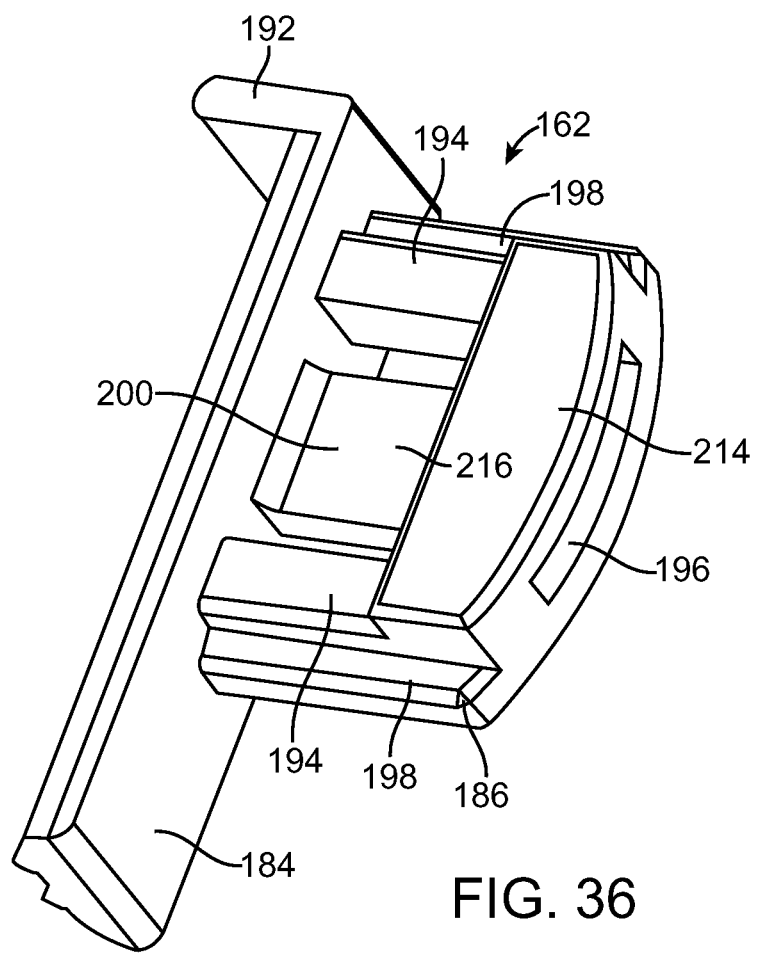
FIG. 36 is a bottom perspective view of the clamping mechanism of FIG. 35.
Figure 37:
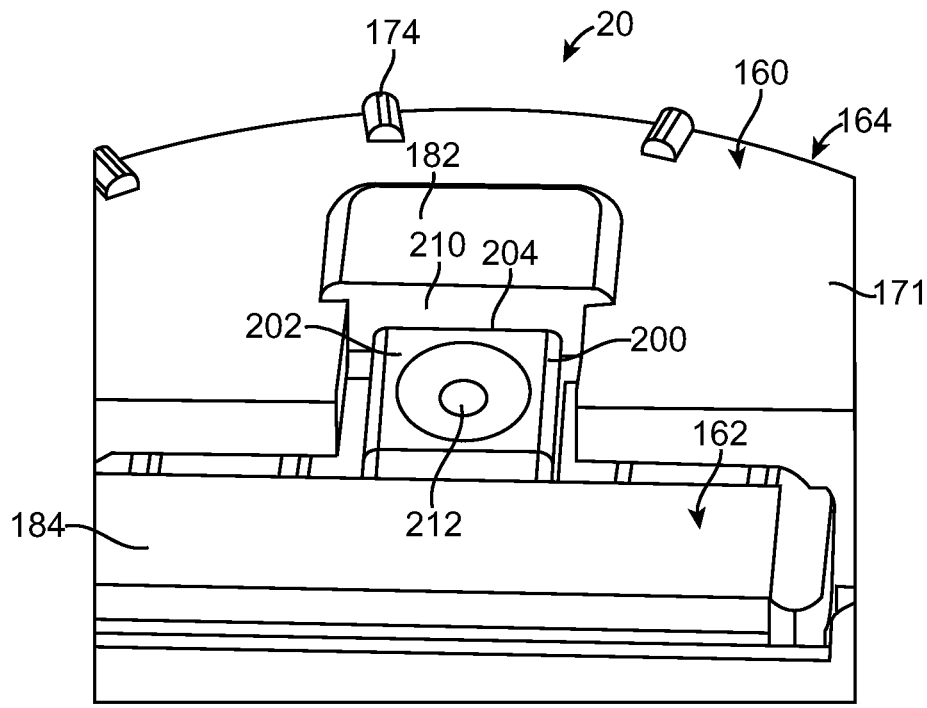
FIG. 37 is a close-up top perspective view of the retainer of FIG. 28, particularly showing the clamping mechanism in a closed position.
Figure 38:
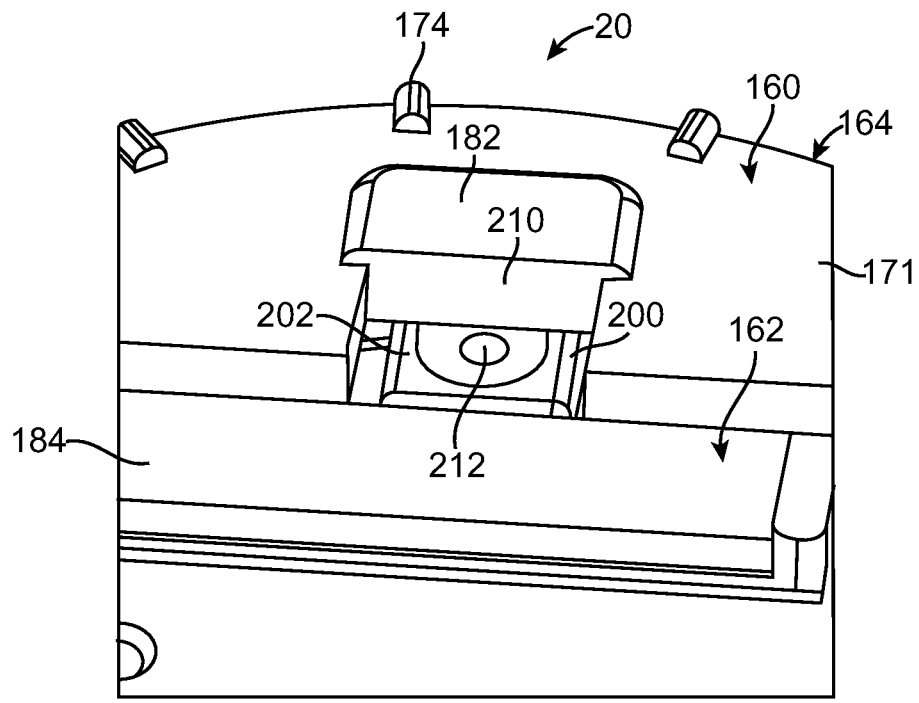
FIG. 38 is a close-up top perspective view of the retainer of FIG. 28, particularly showing the clamping mechanism in an open position.

To prevent the resilient arm 200 from fatiguing or breaking, the clamping mechanism 162 further comprises a stop 214 that is affixed to the U-shaped flange 186 to prevent the resilient arm 200 from bending past a certain point, as best shown in FIGS. 35 and 36. In the illustrated embodiment, the stop 214 is located at the center of the U-shaped flange 186 between the legs 194, so that the bottom surface 216 of the resilient arm 200 bears against an upper surface 218 of the stop 214 when the downward force is applied to the locking tab 202.

Figure 41:
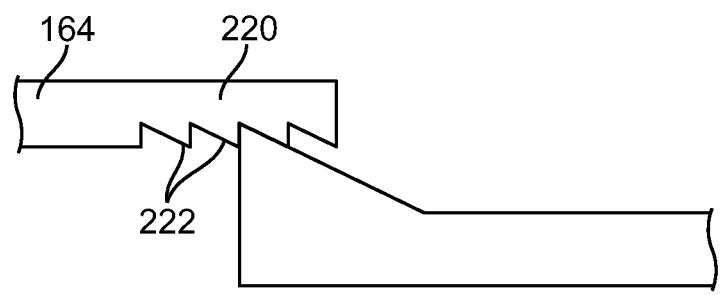
FIG. 41 is a plan view showing another alternative technique in which the clamping mechanism and retainer support of the retainer of FIG. 28 interact to lock and unlock the clamping mechanism from the retainer support.

In an alternative embodiment, the retainer support 160 has a plurality of complementary locking mechanisms with which a locking element of the clamping mechanism 162 is configured for selectively engaging, such that the movable clamping bar 184 is configured for being located relative to the disk 164 at different positions. For example, as illustrated in FIG. 41, the retainer support 160 may be provided with a ratchet 220 having teeth 222, any of which the locking tab 202 of the resilient arm 200 may engage. Thus, the U-shaped flange 186 may be slid towards the lead slot 166, such that the abutment surface 208 of the locking tab 202 slides along the ratchet 214. When movement of the U-shaped flange 186 ceases, the end of the resilient arm 200 will engage one of the teeth 222 on the ratchet 220. In this manner, different sized leads may be used with the burr hole plug 16.

Notably, the retainer support 160 and the clamping mechanism 162 may have additional features that maximize the clamping force applied to the stimulation lead. For example, the retainer 20, including the retainer support 160 and the clamping mechanism 162, can be composed of PEEK, thereby substantially increasing the durability of the retainer 20, even in view of the open architecture of the retainer support 160. Since deformation of the movable clamping bar 184 will be substantially decreased by the PEEK composition, the clamping force will be more uniformly distributed along the movable clamping bar 184, thereby securing the stimulation lead in a more reliable manner. The reduced deformation of the U-shaped flange 186 and disk 164 will also allow the clamping mechanism 162 to slide relative to the retainer support 160 in a more reliable and robust manner.

Figure 42A:
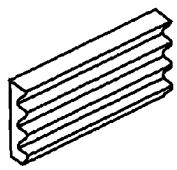
FIGS. 42A-42N are perspective views showing different relief surfaces that can be used for the clamping mechanism of FIG. 35.
Figure 42E:
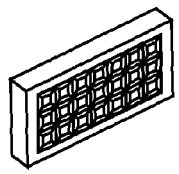
Figure 42J:
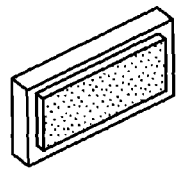
Figure 42B:
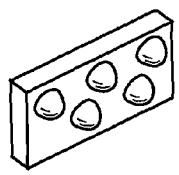
Figure 42F:
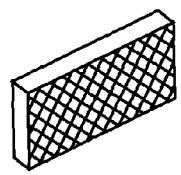
Figure 42K:
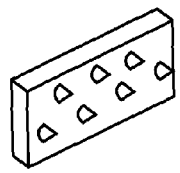
Figure 42C:
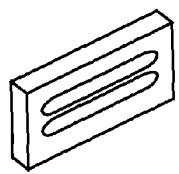
Figure 42G:
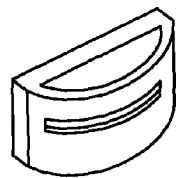
Figure 42L:
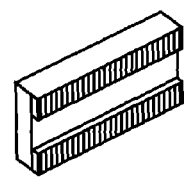
Figure 42D:
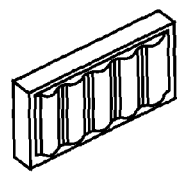
Figure 42H:
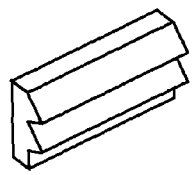
Figure 42M:
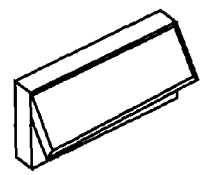
Figure 42I:
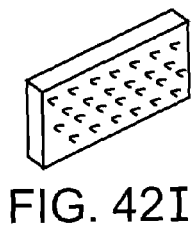
Figure 42N:
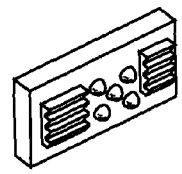

In addition, the clamping surfaces 188, 190 of the movable clamping bar 184 and/or fixed clamping bar 176 may be provided with any one of a variety of relief features. For example, the relief features may include horizontal ridges or bars (FIG. 42A), dimples or bumps (FIG. 42B), horizontal serrations (FIG. 42C), vertical corrugations (FIG. 42D), tread plates (FIG. 42E), knurl pattern (FIG. 42F), spring (FIG. 42G), barbs (FIG. 42H), grit finish (blasted, plated, mold finish) (FIG. 42I), non-skid surface (FIG. 42J), spikes or tines (FIG. 42K), horizontal channel (FIG. 42L), flex barb (FIG. 42M), any combination of the above, e.g., horizontal ridges and dimples or bumps (FIG. 42N).

Figure 43:
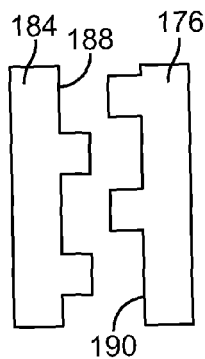
FIG. 43 is a plan view of an interlocking relief structure that can be used for the clamping mechanism of FIG. 35.

The above relief features will increase the retention force of the movable clamping bar 184 and/or fixed clamping bar 176 by altering the coefficient of friction, increasing compression, "biting" into the lead, creating edges to catch the lead, increasing surface area, locally increasing clamping force, deformation of the lead into surface recesses, etc. Combinations of relief features in multiple directions on the movable clamping bar 184 and/or fixed clamping bar 176 can prevent the lead from moving in multiple directions (e.g., along the lead axis and along the face of the movable clamping bar 184 and/or fixed clamping bar 176 perpendicular to the lead axis). Relief structures can be provided on the clamping surfaces 188, 190 of both the movable clamping bar 184 and the fixed clamping bar 176 to operate in combination with each other to neck or otherwise provide a tortuous path for the lead. For example, the relief structures on the clamping surfaces 188, 190 may be staggered or interlocking (FIG. 43) to neck or create a tortuous path for the stimulation lead.

While the burr hole plug 16 illustrated in FIGS. 2-7 provide lead exit grooves 36 on the plug base 18, lead exit grooves can be advantageously provided on the retainer instead. For example, referring to FIG. 44, another retainer 230 that can be mounted within the aperture 26 of the plug base 18 will now be described. The retainer 230 is similar to the retainer 20 illustrated in FIGS. 28-33, with the exception that it comprises a plurality of lead exit grooves 232 (in this case, two) configured for seating the stimulation lead when it is bent at a ninety degree angle relative to the axis of the burr hole, such that the stimulation lead is radially directed towards the plug base 18. In this case, the plug base 18 need not include lead exit grooves. In the illustrated embodiment, the exit grooves 232 are located on opposite sides of each other and are circumferentially oriented perpendicular to the lead slot 166, and thus, the movable clamping bar 184. That is, an imaginary line drawn from each exit groove 232 to the center of the disk 164 will be perpendicular to the movable clamping bar 184. In this manner, it is assured that when the stimulation lead is bent down and received into one of the exit grooves 232, any tensile force applied to the stimulation lead will be directed at an angle perpendicular to the orientation of the lead slot 166, and thus, counteracted by the retention force between the top edges of the movable clamping bar 184 and fixed clamping bar 176 and the stimulation lead.

Because there are two exit grooves 232, the direction in which the stimulation lead exits the retainer 230 may be selected. In an alternative embodiment, a plurality of fastening exit grooves (not shown) can be provided on each side of the clamping slot 166, such that the stimulation lead may be placed and perpendicularly bent downward at multiple locations along the clamping slot 166. In another alternative embodiment, each fastening exit groove 232 may be slid back and forth in a direction parallel to the clamping slot 166, such that the stimulation lead may be placed and perpendicularly bent downward at multiple locations along the clamping slot 166.

Figure 45:
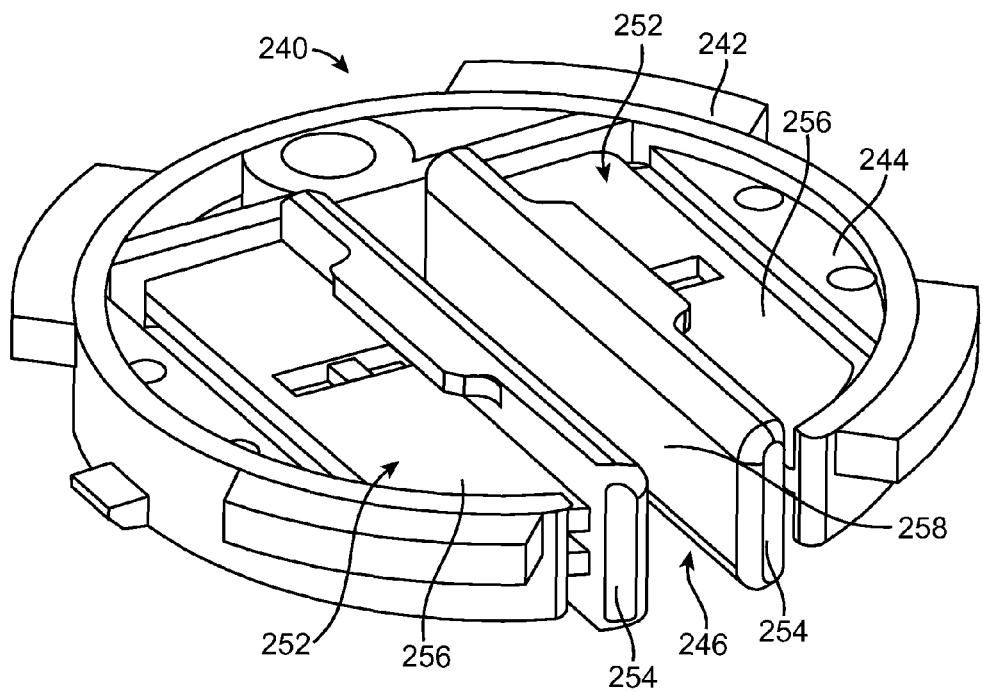
FIG. 45 is a top perspective view of another alternative embodiment of a retainer that can be used in the burr hole plug of FIG. 2.

While the previous retainers 20, 230 include single slidable clamping mechanisms, retainers constructed in accordance with the present inventions may include more than one slidable clamping mechanism. For example, referring to FIG. 45, another retainer 240 that can be mounted within the aperture 26 of the plug base 18 will now be described. Like the previous retainer 20, the retainer 240 comprises a retaining support 242 that includes a disk 244 and an open slot 246 formed in the disk 244 for laterally receiving the stimulation lead, thereby allowing the retainer 240 to be mounted within the plug base aperture 26 after the stimulation lead has been introduced through the burr hole. The retainer 240 may include other features, such as a pop-out notch, sun-dial ticks, and lead exit grooves (not shown) located on the disk 244.

The retainer 240 differs from the retainer 20 in that it comprises two slidable clamping mechanisms 252, each including a movable clamping bar 254 and a flange 256 slidably engaged with the disk 244 to laterally slide the movable clamping bar 254 relative to the disk 244 and selectively secure the stimulation lead received within the lead slot 246 or release the stimulation lead received within the lead slot 246. The movable clamping bars 254 extend parallel to the lead slot 246 opposite each other, such that clamping surfaces 258 (only one shown) of the respective clamping bars 254 are configured for clamping the stimulation lead against each other. Like the clamping surfaces 188, 190 of the respective clamping bar 184 and clamping bar 176 discussed above with respect to the retainer 20, the clamping surfaces 258 of the clamping bars 254 may be ribbed or comprise other relief features (not shown), thereby increasing the lead retention force. In addition, each clamping mechanism 252 may alternatively include a U-shaped flange, resilient arm, locking tab, and an arm stop (all not shown) similar to the U-shaped flange 186, resilient arm 200, locking tab 202, and arm stop 220 described above with respect to the retainer 20.

The retainer 240 may include features formed into the disk 244 for accommodating the slidable clamping mechanisms 252. For example, the retainer support 242 may include recesses with opposing C-channels (not shown) similar to the recess 178 and opposing C-channels 180 described above with respect to the retainer 20. The retainer support 242 may also include recessed stops (not shown) similar to the recessed stop 182 described above with respect to the retainer 20 for respectively accommodating locking elements of the clamping mechanism 252. Preferably, the clamping bars 254 of the clamping mechanisms 252 can be variably locked in different positions, e.g., by utilizing ratchets 220, as illustrated in FIG. 41.

Figure 46:
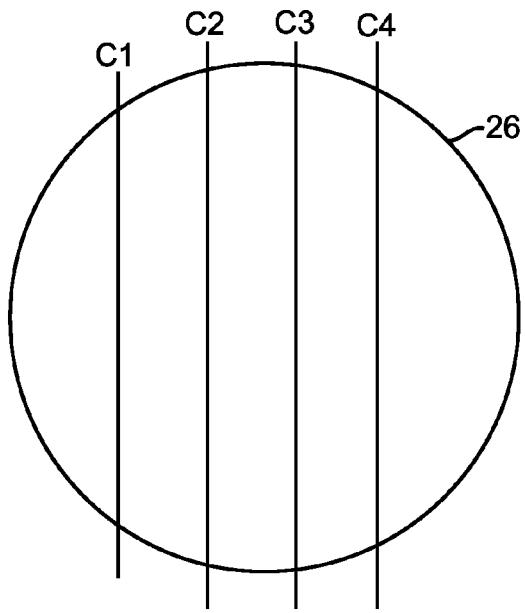
FIG. 46 is a diagram illustrating different chords along which stimulation leads may be clamped by the retainer of FIG. 45.
Figure 47:
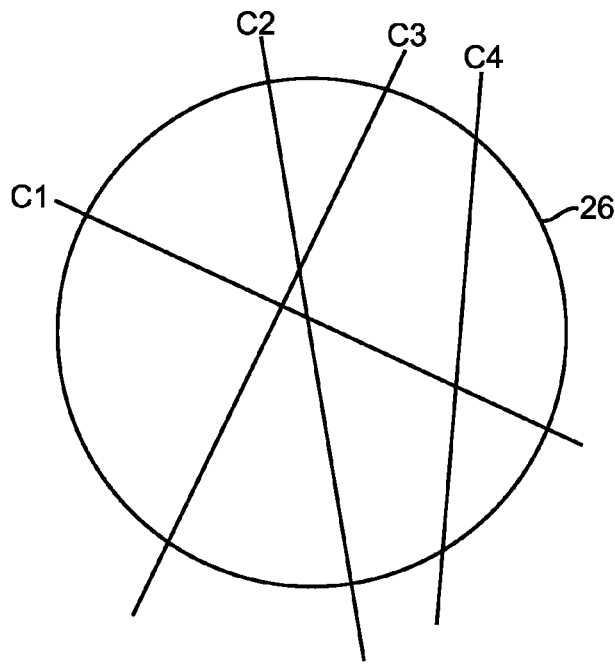
FIG. 47 is a diagram illustrating further chords along which stimulation leads may be clamped by the retainer of FIG. 45.

Thus, it can be appreciated that instead of securing the stimulation lead between a slidable clamping bar and a fixed clamping bar, the slidable clamping mechanisms 252 may both be slid relative to the disk 244 in order to secure a stimulation lead between the movable clamping bars 254. Significantly, because both clamping mechanisms 252 are slidable relative to the disk 244, a plurality of stimulation leads can be secured along any one of a plurality of different chords C1-C4 of the plug base aperture 26, as illustrated in FIG. 46. Notably, because the retainer 240 may be mounted within the plug base aperture 26 in any rotational orientation, the chords C1-C4 along which the stimulation leads are secured by the clamping mechanisms 252 may also be in different rotational orientations, as illustrated in FIG. 47. Thus, given any number of stimulation leads arranged along a single chord (for example, any pair of leads), the retainer 240 is capable of simultaneously securing the stimulation leads, thereby obviating the need to have separate burr holes, decreasing patient risk, decreasing procedure time, decreasing cost to the patient, etc.

Although the retainer 240 includes two slidable clamping mechanisms, retainers constructed in accordance with the present inventions may include more than two slidable clamping mechanisms. For example, referring to FIGS. 45a and 45b, another retainer 241 that can be mounted within the aperture 26 of the plug base 18 will now be described. Like the previous retainer 240, the retainer 241 comprises a retaining support 243 that includes a disk 245 and an open slot 247 formed in the disk 245 for laterally receiving the stimulation lead, thereby allowing the retainer 241 to be mounted within the plug base aperture 26 after the stimulation lead has been introduced through the burr hole. The retainer 240 may include other features, such as a pop-out notch, sun-dial ticks, and lead exit grooves (not shown) located on the disk 245. The retainer 241 differs from the retainer 240 in that it comprises three slidable clamping mechanisms 249, each including a flange 251 with a concave tip 253. In another embodiment illustrated in FIGS. 45c and 45d, the retainer 241 may include four slidable clamping mechanisms 249.

Figure 45A:
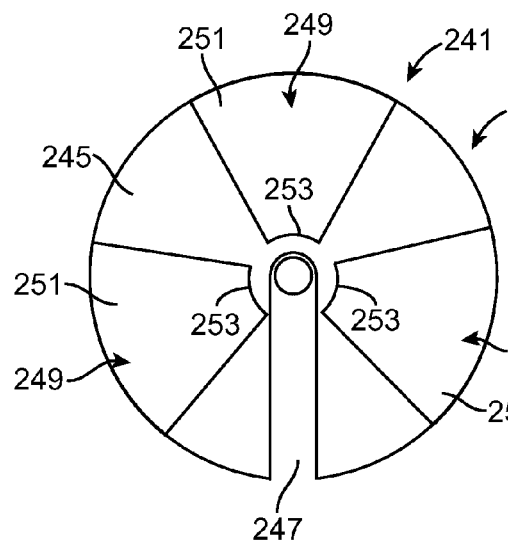
FIGS. 45a-45f are top views of still other alternative embodiments of a retainer that can be used in the burr hole plug of FIG. 2.
Figure 45B:
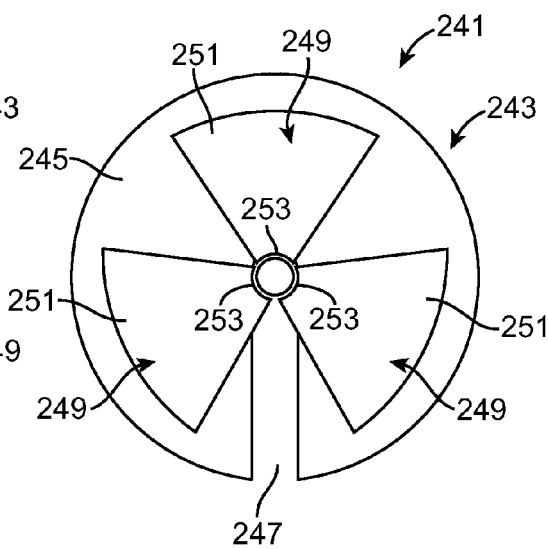
Figure 45C:
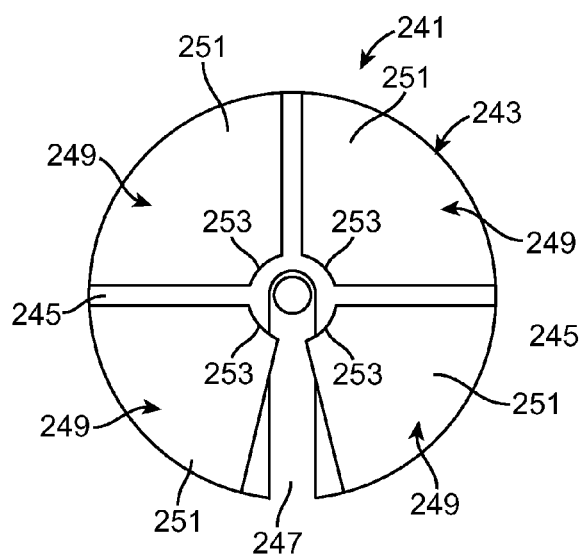
Figure 45D:
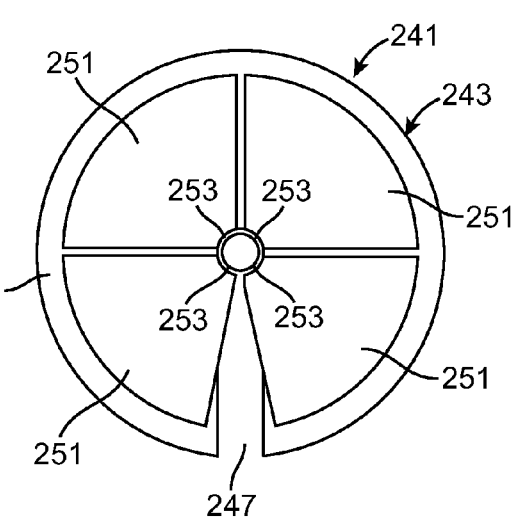

In either embodiment, each flange 251 is slidably engaged with the disk 245 to laterally slide the concave tip 253 radially inward relative to the disk 245 and selectively secure the stimulation lead received within the lead slot 247 (FIGS. 45b and 45d) or laterally slide the concave tip 253 radially outward relative to the disk 245 and release the stimulation lead received within the lead slot 247 (FIGS. 45a and 45c). The concave tips 253 are opposite to each other to clamp the stimulation lead therebetween. Each clamping mechanism 253 may alternatively include a U-shaped flange, resilient arm, locking tab, and an arm stop (all not shown) similar to the U-shaped flange 186, resilient arm 200, locking tab 202, and arm stop 220 described above with respect to the retainer 20.

Figure 45F:
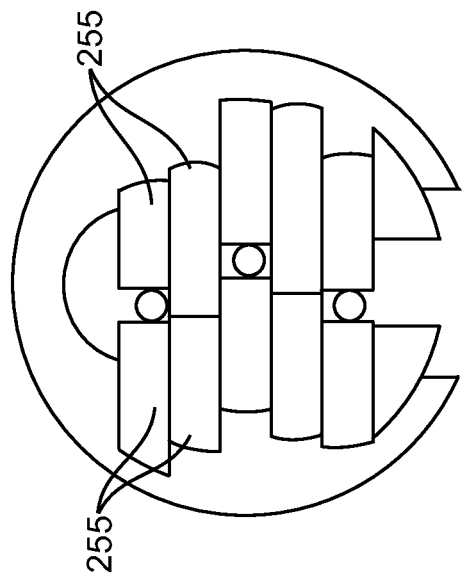
Figure 45E:
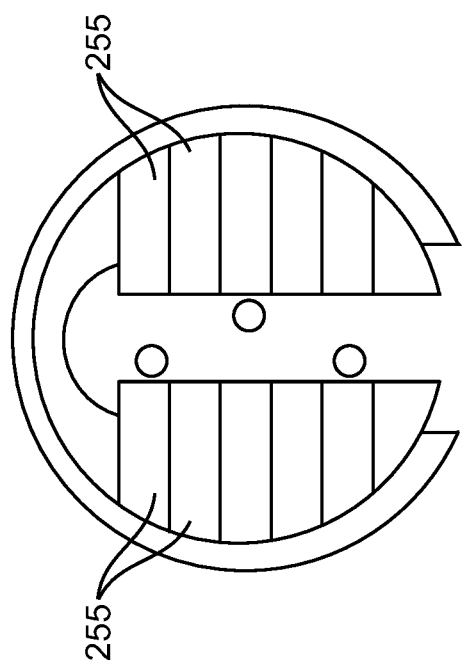
Figure 50:
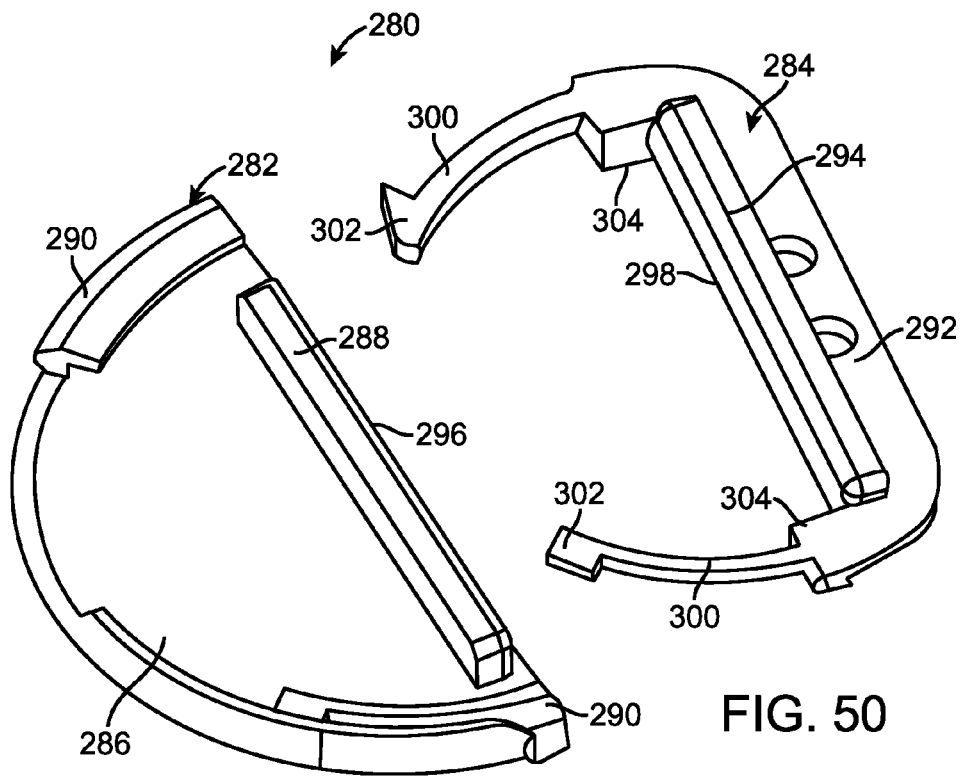
FIG. 50 is a top perspective view of yet another alternative embodiment of a retainer that can be used in the burr hole plug of FIG. 2, particularly shown in an unclamped position.
Figure 51:
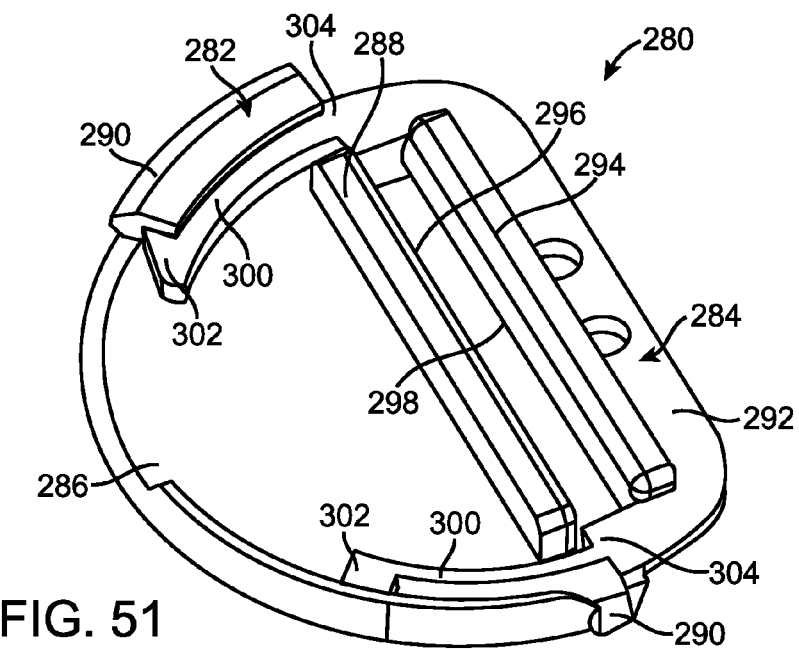
FIG. 51 is a top perspective view of the retainer of FIG. 50, particularly shown in a clamped position.

In an alternative embodiment illustrated in FIGS. 50 and 51, multiple opposing sets of slidable clamping mechanisms 255 can be independently slid relative to each other to selectively secure multiple stimulation leads received within the lead slot (FIG. 45f) or release the stimulation leads received within the lead slot (FIG. 45e).

Figure 48:
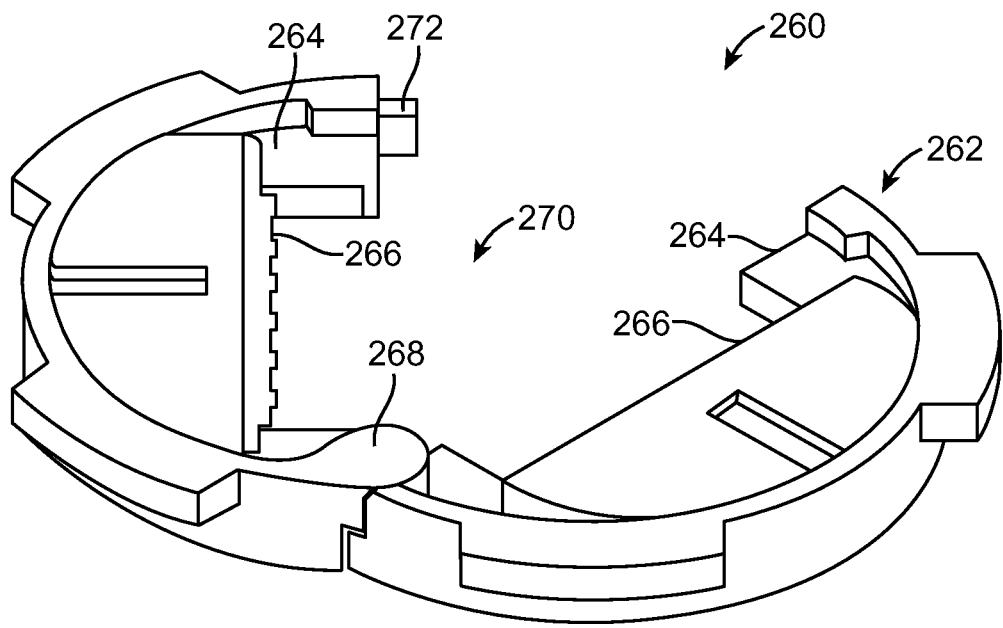
FIG. 48 is a top perspective view of still another alternative embodiment of a retainer that can be used in the burr hole plug of FIG. 2, particularly shown in an unclamped position.
Figure 49:
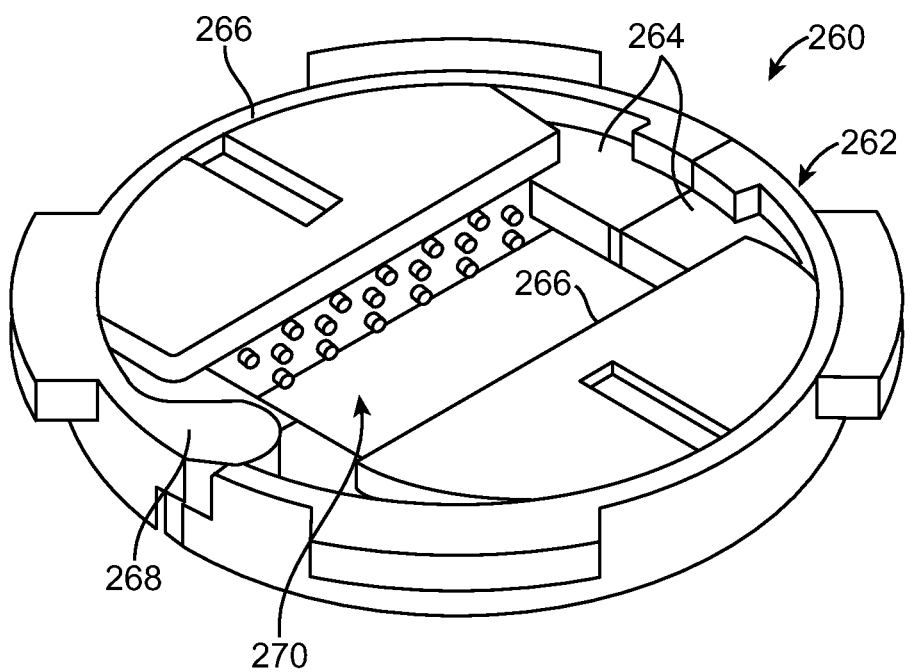
FIG. 49 is a top perspective view of the retainer of FIG. 48, particularly shown in a clamped position.

While the previous retainers 20, 230, 240 include fixed open lead slots for receiving stimulation leads, retainers may have leads slots that alternately open and close. For example, as illustrated in FIGS. 48 and 49, a hinged retainer 260 will now be described. The retainer 260 is similar to the retainer 240 illustrated in FIG. 45, with the exception that it comprises a retaining support 262 that includes a pair of semi-spherical disk portions 264, a pair of slidable clamping mechanisms 266, and a hinge 268 coupled to the disk portions 264, such that the disk portions 264 can be alternately hinged open (FIG. 48) to open a lead slot 270 for laterally receiving the stimulation lead and hinged close (FIG. 49) to close the lead slot 270 around the stimulation lead. In this manner, the retainer 260 may still be mounted within the plug base aperture 26 after the stimulation lead has been introduced through the burr hole without sacrificing the structural integrity typically associated with a disk that is completely closed around its circumference. The retainer 240 further comprises a locking mechanism 272 (best shown in FIG. 48) in the form of a protuberance the end of one of the disk portions 264 and a corresponding recess (not shown) on the end of the other disk portion 264, such that the lead slot 270 remains closed when manipulating the clamping mechanisms 266. The clamping mechanisms 266 function in the same manner as the clamping mechanisms 252 described above to selectively secure the stimulation lead received within the lead slot 268 or release the stimulation lead received within the lead slot 268.

Other types of lead retainers are also contemplated by the present inventions. For example, referring to FIGS. 50 and 51, another lead retainer 280 comprises a retaining support 282 configured for being mounted within the aperture of the plug base 18, and a clip 284 configured for mating with the retaining support 282. In the illustrated embodiment, the retaining support 282 comprises a semi-circular flange 286, a fixed clamping bar 288 located on the diameter of the semi-circular flange 286, and a pair of opposing annular C-channels 290 extending along the circumference of the semi-circular flange 286. The retainer 280 may include other features, such as a pop-out notch, sun-dial ticks, and lead exit grooves (not shown) located on the semi-circular flange 286.

The clip 284 comprises a transverse member 292 and a clamping bar 294 disposed on the transverse member 292. Thus, when the clip 294 is mated with the retaining support 292, the stimulation lead will be secured between a clamping surface 296 of the retaining support 282 (and in particular the fixed clamping bar 288) and a clamping surface 298 of the clip 284 (and in particular the movable clamping bar 294). The clip 284 is configured for mating with the retaining support 282 in an interference arrangement. To this end, the clip 284 has a pair of opposing resilient arms 300 extending from the transverse member 292. The arms 300 are configured for slidably engaging the respective C-channels 290 located on the semi-circular flange 286. Thus, the clip 284 can be mated with the retaining support 282 by inserting the respective arms 300 of the clip 284 into the C-channels 290. Notably, the resiliency of the arms 300 allows them to flex outward as they are inserted into the C-channels 290, and once fully inserted, they flex back to the normal shape to grasp the C-channels 290.

The clip 284 further comprises a pair of locking elements, and in particular, a pair of tabs 302 respectively disposed on the ends of the arms 300, such that when the arms 300 are fully inserted into the C-channels 290, the tabs 302 engage the ends of the opposing C-channels 290 to lock the clip 284 relative to the retaining support 282. The arms 300 may be displaced toward each other away from the C-channels 290 to disengage the locking tabs 302 from the opposing C-channels 290, thereby allowing the clip 284 to be removed from the retaining support 282. The clip 284 further comprises a pair of stops 304 located between the transverse member 292 and the respective resilient arms 300 that abut the fixed clamping bar 288 and the front of the C-channels 290 when the clip 284 is mated with the retaining support 282. In this manner, the clamping bar 294 of the clip 284 is prevented from moving past a certain point, thereby preventing damage to the stimulation lead.

Figure 52:
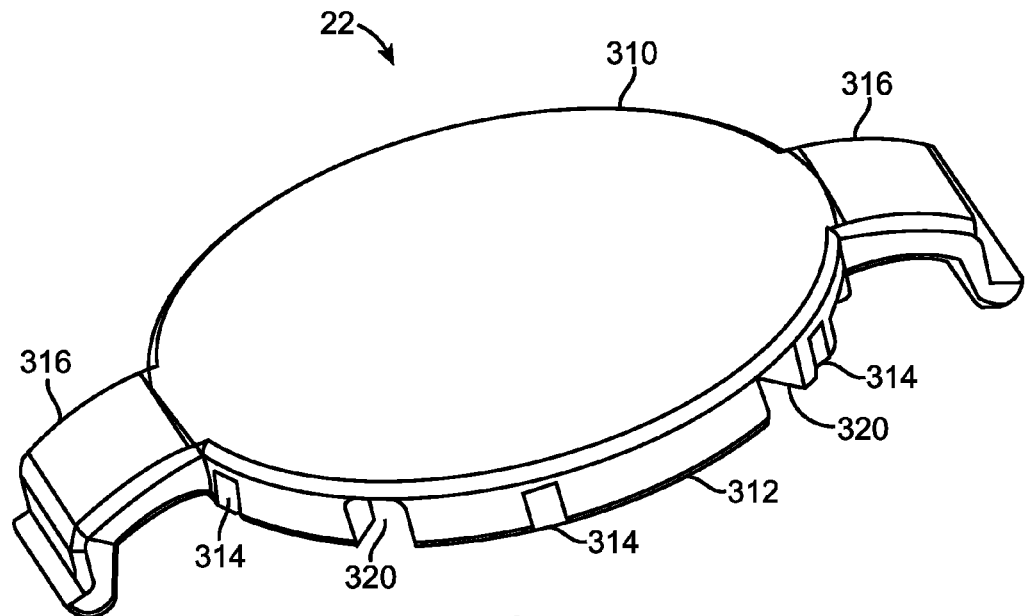
FIG. 52 is a top perspective view of a cap used in the burr hole plug of FIG. 2.
Figure 53:
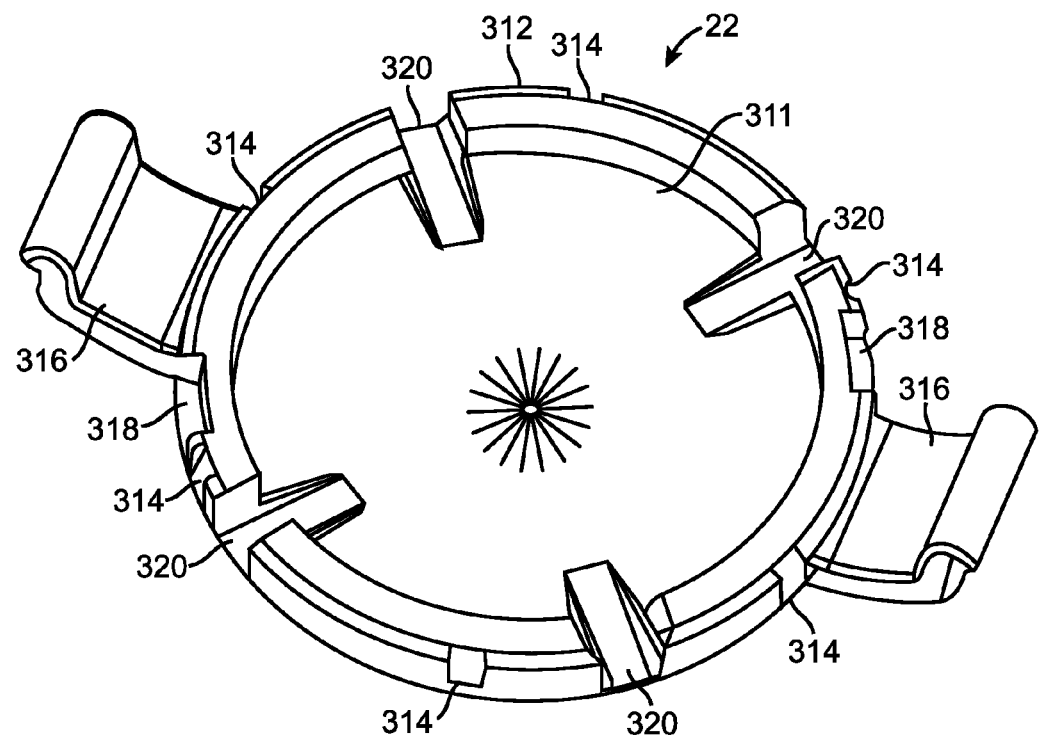
FIG. 53 is a bottom perspective view of the cap of FIG. 52.

Referring to FIGS. 52 and 53, the details of the cap 22 will now be described. The cap 22 is configured for mounting to the plug base 18 over the retainer 20, thereby securing the stimulation lead, as well as closing the burr hole. The cap 22 may be composed of a suitable hard or soft biocompatible material, such as titanium, a hard polymer, a soft polymer, silastic, elastomer, or any other combination thereof. The cap 22 may be composed of PEEK, although the durability of the cap 22 may not be as important as the other components of the burr hole plug 16.

The cap 22 comprises a circular lid-type body 310 having a rim 312 sized and shaped to be disposed within the plug base aperture 26 and resting on the retaining disk 164. To accommodate the locking ramps 48 located on the inner surface 46 of the plug base body 24, the cap 22 includes a plurality of recesses 314 located on the exterior surface of the rim 312. The number of circumferential spacing of the recesses 314 matches the number and spacing of the locking ramps 48, such that each ramp 48 is received into a corresponding recess 314 when the cap 22 is mounted to the plug base 18.

The cap 22 further comprises a plurality of winged tabs 316 (in this case, two) configured for being received into the corresponding locking recesses 42 located on the plug base body 24 (shown in FIG. 8) in an interference arrangement, and in particular, a snap-fit arrangement, thereby preventing rotation of the cap 22, as well as also ensuring that the cap 22 is securely mounted to the plug base 18. Alternatively, other locking mechanisms, such as snaps, hooks, grips, ledges, etc, or any other mechanical structure can be used to lock the cap 22 in place. The cap 22 also comprises a plurality of pop-out notches 318 (in this case, two) formed in the rim 312 of the cap body 310, such that when the cap 22 is mounted and secured to the plug base 18, one of the pop-out notches 318 corresponds with the pop-out recess 38 located at the inner edge 40 of the ring-shaped plug body 24 (shown in FIG. 8). Thus, the cap 22 can be conveniently removed from the plug base 18 by inserting a tool within the pop-out recess 38 and into the corresponding pop-out notch 318 in the cap 22.

The cap 22 further comprises a plurality of lead clamp grooves 320 (in this case, four) located on the bottom surface of the cap 22 and extending through the rim 312. The number and circumferential spacing of the lead clamp grooves 320 matches the number of spacing of the lead exit grooves 36 located on the plug base 18 (shown in FIG. 8), such that lead clamp grooves 320 will circumferentially align with, and be immediately radially adjacent to, the lead exit grooves 36. In this manner, when the cap 22 is mounted to the plug base 18, the stimulation lead will be firmly seated within the selected lead clamp groove 320. Thus, the selected lead clamp groove 320 will apply downward pressure to the stimulation lead causing the corresponding lead exit groove 36 to counter with an upward pressure to the stimulation lead, thereby providing a secure frictional fit between the stimulation lead and the lead exit and lead clamp grooves 36, 320.

Figure 54:
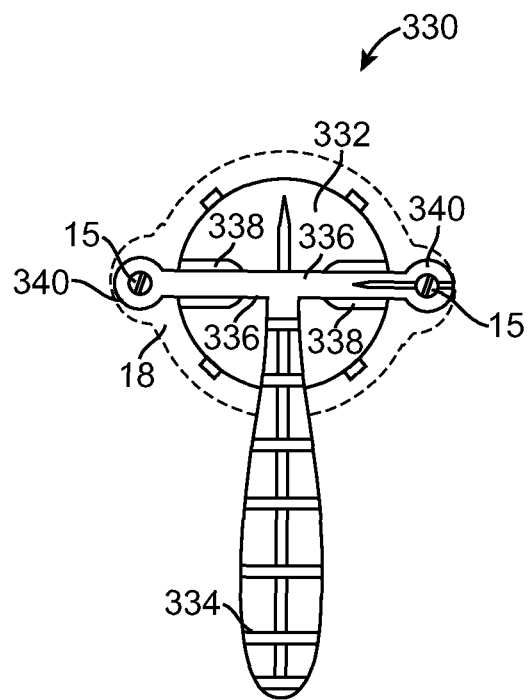
FIG. 54 is a top view of a plug base holding tool that can be used to mount the plug base of FIG. 8 within a burr hole.
Figure 55:
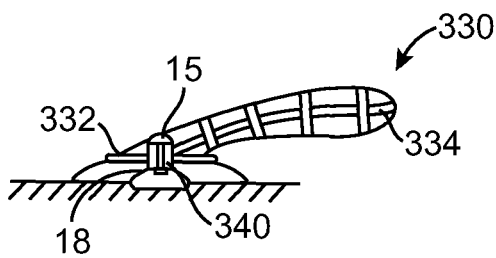
FIG. 55 is a side view of the plug base holding tool of FIG. 54, particularly shown engaged with the plug base of FIG. 8.
Figure 56:
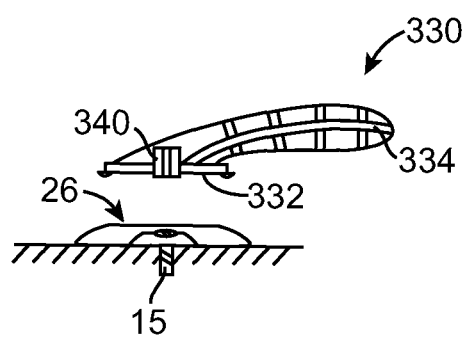
FIG. 56 is a side view of the plug base holding tool of FIG. 54, particularly shown disengaged from the plug base of FIG. 8.

Having described the burr hole plug 16, various tools that can be used to install a burr hole plug into a burr hole will now be described. Referring to FIGS. 54-56, one embodiment of a plug base holding tool 330 configured for holding the plug base 18 to aid in its mounting to the cranium of the patient will be described. The plug base holding tool 330 generally comprises a burr hole cover 332, a handle 334 mounted to the burr hole cover 332, and a pair of screw holder arms 336 extending in opposite directions from the handle 334. The tool 330 may be composed of a suitable rigid and robust material, such as stainless steel or a durable plastic, such as polypropylene, polycarbonate, or even if PEEK if very little deformation is desired. The tool 330, or at least the structural portion of the tool, may be a unibody design, thereby increasing the strength and robustness of the tool 330.

The burr hole cover 332 has a lid-shape having an aperture geometrically similar to the aperture 26 of the plug base 16 (in this case, circular) and is sized to fit into and completely cover the plug base aperture 26. The lip of the burr hole cover 332 may rest on annular ledges of the plug base 16 in the same manner as the retainer rests on the annular ledges described above. In this manner, any potential for debris, such as screws, falling through the plug base aperture 26 and into the burr hole, or accidental slippage of tools, such as a screwdriver, into the burr hole, is minimized. In an optional embodiment, the burr hole cover 332 includes features, such as snaps, keyways, set screws, adhesive, suction ports, threads, etc., that engage the plug base 16 in a manner that secures the burr hole cover 332 within the aperture 26 and also allows the burr hole cover 332 to be removed from the plug base 16 after the plug base 16 is anchored to the cranium of the patient. Alternatively, the tool 330 can be shaped in a manner that positions its center of gravity, such that the tool 330 remains on a flat surface without fastening it to the plug base 16 (i.e., it does not fall over). In the case where the plug base 16 does not include self-centering tabs, the tool 330 may include centering tabs (not shown) that extend downward from the cover 332, through the aperture 26 in the plug base 16, and into the burr hole, in order to center both the plug base 16 relative to the burr hole.

Figure 57:
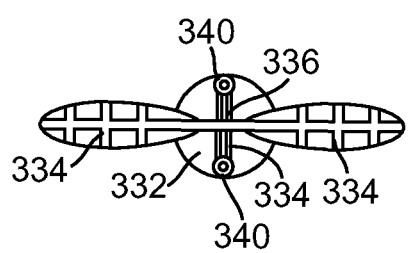
FIG. 57 is a top view of another plug base holding tool that can be used to mount the plug base of FIG. 8 within a burr hole.
Figure 58:
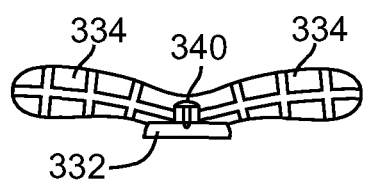
FIG. 58 is a side view of the plug base holding tool of FIG. 57, particularly shown engaged with the plug base of FIG. 8.

The handle 334 laterally extends away from the burr hole cover 332, and thus the burr hole, as to not interfere with the placement, visualization, alignment, and anchoring of the plug base 16 to the burr hole. The handle 334 is shaped to more ergonomically allow the physician to grasp the handle. For example, the profile of the handle 334 flares out as the handle 334 laterally extends from the burr hole cover 332 to allow the handle 334 to be more easily gripped. In addition, the handle 334 includes relief features (in this case, grooves in a criss-cross pattern) to facilitate gripping of the handle 334, which may be important in a slippery environment (such as a physician wearing wet gloves). In an alternative embodiment illustrated in FIGS. 57 and 58, two opposing handles 334 laterally extend from the burr hole cover 332 in opposite directions, thereby allowing the physician the option of holding the tool 330 from two different sides (e.g., in case the physician does not have access to one side of the burr hole). Additional handles (not shown) can be provided (e.g., two opposing handles clocked ninety degrees from the handles 334) to provide additional gripping options for the physician.

In the illustrated embodiment, the burr hole cover 304 includes a pair of recesses 338 formed in its upper surface to accommodate the laterally extending screw holder arms 336. The screw holder arms 336 include collars 340 that are spaced from each other, such that they respectively align with the screw holes 34 located on the plug base 18 when the burr hole cover 332 is mounted within the plug base aperture 26. Thus, the screws 15 may be accurately inserted through the collars 340 and aligned with the screw holes 34 (shown in FIG. 8) in the plug base 18, such that the screws 15 can be conveniently screwed into the cranium of the patient. Preferably, the apertures within the collars 340 are slightly larger than the diameter of the screw heads, such that the screw heads can be recessed into the collars 340, thereby allowing the screws 15 to be fully screwed into the cranium without removing the tool. In addition to aligning the screws 15 with the screw holes 34 of the plug base 18, the collars 340 also limit slippage of the screw driver should it occur.

Figure 59:
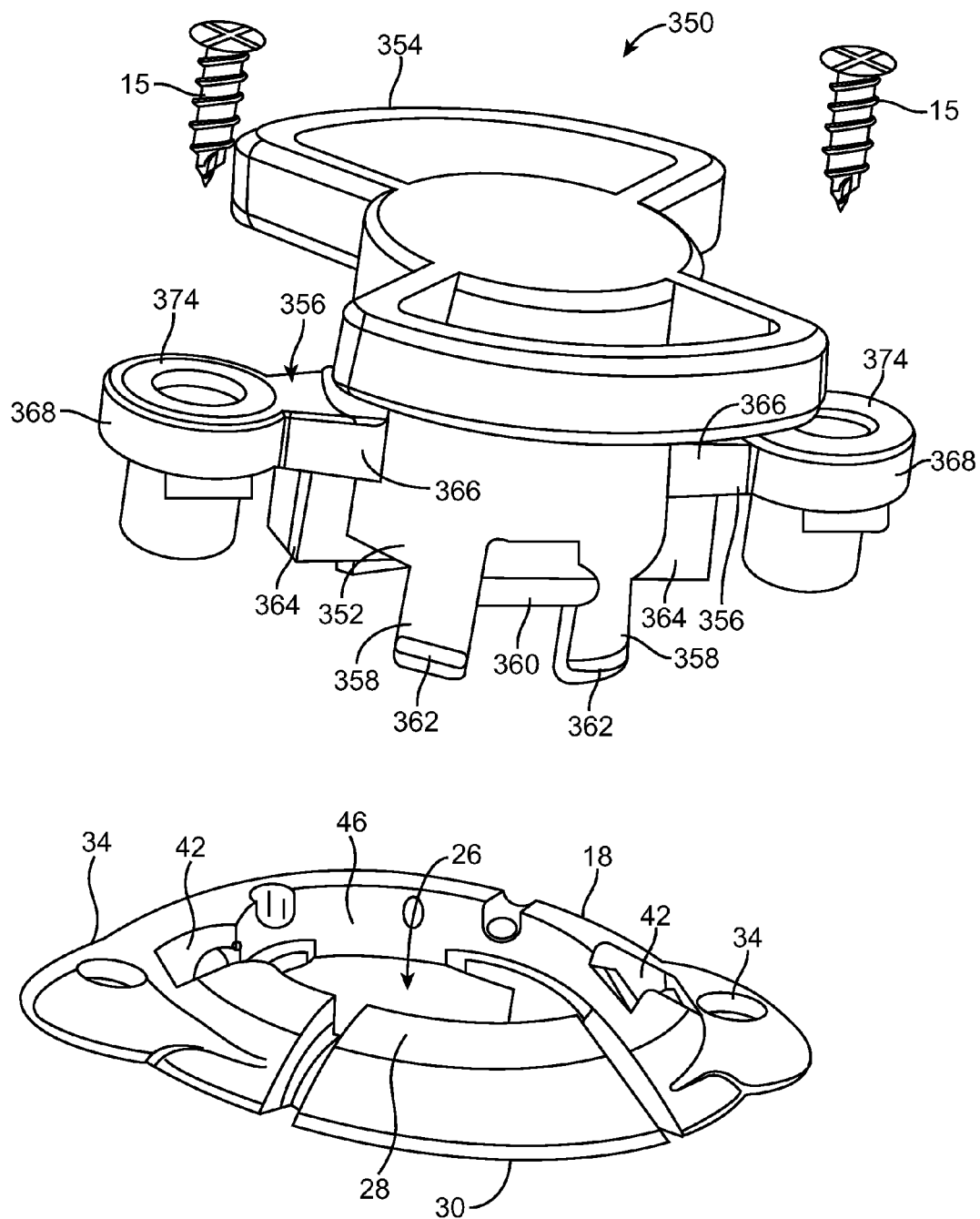
FIG. 59 is a top perspective view of still another plug base holding tool that can be used to mount the plug base of FIG. 8 within a burr hole, particularly showing the tool disengaged from the plug base.
Figure 60:
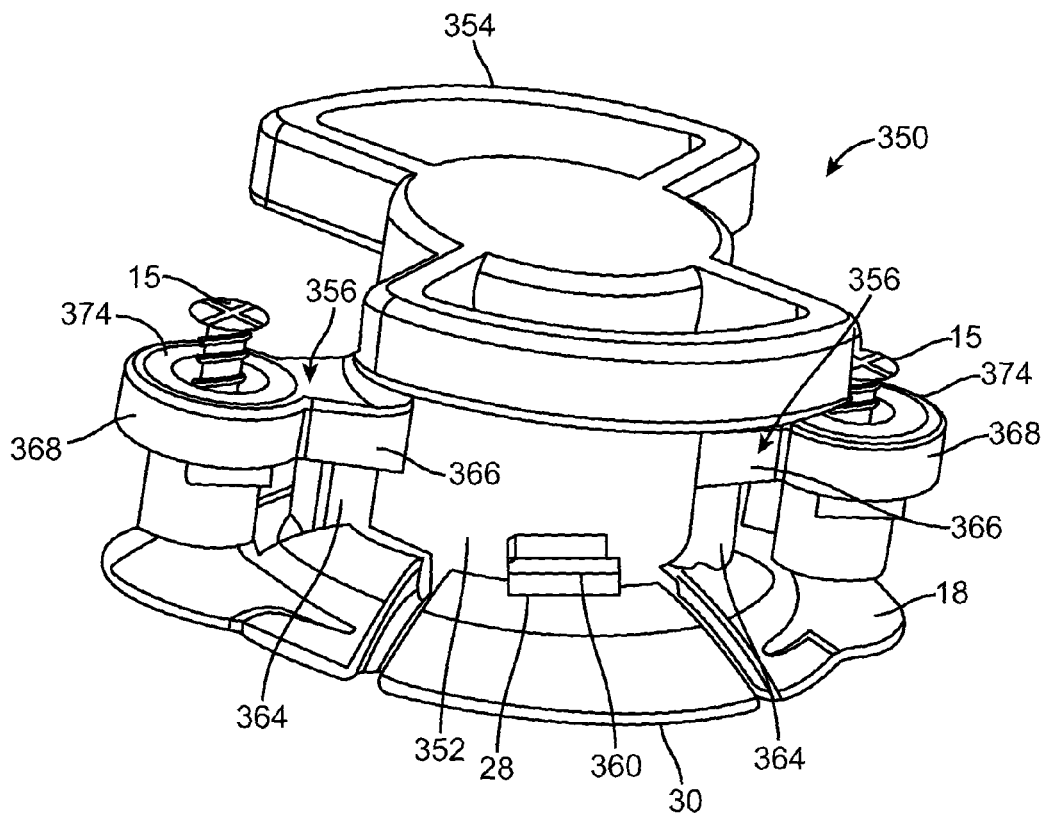
FIG. 60 is a top perspective view of the plug base holding tool of FIG. 59, particularly showing the tool engaged with the plug base.
Figure 61:
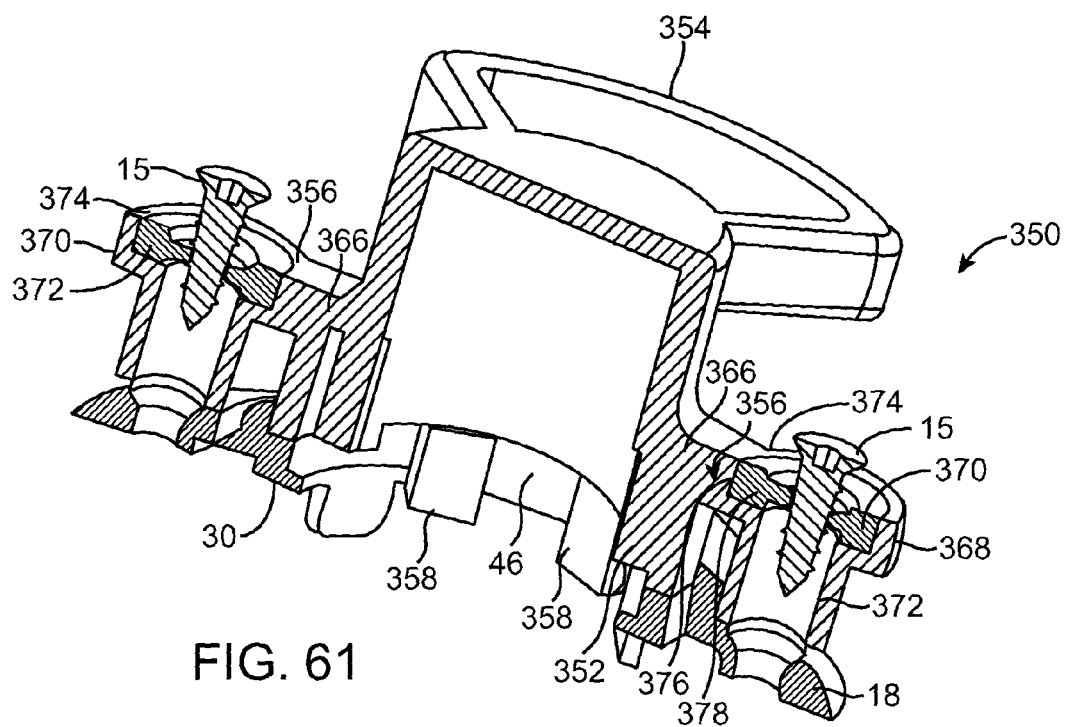
FIG. 61 is a cross-sectional view of the plug base holding tool and plug base of FIG. 60.

Referring to FIGS. 59-61, another embodiment of a plug base holding tool 350 configured for being attached to the plug base 18 to aid in its mounting to the cranium of the patient will be described. The plug base holding tool 350 generally comprises a burr hole cover 352, a handle 354 mounted to the burr hole cover 352, and a pair of screw holder mechanisms 356 extending in opposite directions from the burr hole cover 352. The tool 350 may be composed of a suitable rigid and robust material, such as stainless steel or a durable plastic, such as polypropylene, polycarbonate, or even if PEEK if very little deformation is desired. The tool 350, or at least the structural portion of the tool, may be a unibody design, thereby increasing the strength and robustness of the tool 350.

The burr hole cover 352 has a cylindrical shape having a diameter substantially the same as the diameter of the aperture 26 of the plug base 18 (in this case, circular) and is sized to cover the plug base aperture 26. In this manner, any potential for debris, such as screws, falling through the plug base aperture 26 and into the burr hole, or accidental slippage of tools, such as a screwdriver, into the burr hole, is minimized. The tool 350 includes a plurality of centering tabs 358 extending downward from the burr hole cover 352, such that the centering tabs 358 rest against the inner surface 46 of the plug base 18 when the burr hole cover 352 is mounted within the plug base aperture 26. In the illustrated embodiment, two pairs of centering tabs 358 (only one pair shown) are circumferentially disposed opposite each other.

The tool 350 further includes various features that engage the plug base 18 in a manner that secures the burr hole cover 352 within the aperture 26 and also allows the burr hole cover 352 to be removed from the plug base 18 after the plug base 18 is anchored to the cranium of the patient. In particular, the tool 350 comprises upper grasping tabs 360 and lower grasping tabs 362 arranged in manner, such that when the tool 350 is disposed within the aperture 26 of the plug base 18, the thickness of the plug base 18 is disposed between the grasping tabs 360, 362, so that the plug base 18 is grasped from above and below; that is the upper grasping tabs 360 have lower surfaces that frictionally grasp the top surface 28 the plug base 18, and the lower grasping tabs 362 have upper surfaces that frictionally grasp the bottom surface 30 of the plug base 18. The upper surfaces of the lower grasping tabs 362 may be slightly convex, so that they mate perfectly with the slightly concave bottom surface 30 of the plug base 18.

In the illustrated embodiment, there are two upper grasping tabs 360 (only one shown) radially extending from, and circumferentially disposed on opposite sides of, the outer surface of the burr hole cover 352, and two pairs of lower grasping tabs 362 (only one pair shown) extending radially extending from, and circumferentially disposed on opposite sides of, the respective pairs of centering tabs 358. Each pair of lower grasping tabs 362 circumferentially straddles the respective upper grasping tab 360 to firmly engage a circumferential portion of the plug base 18 therebetween. Thus, it can be appreciated that the grasping tabs 360, 362 allow the tool 350 to grasp and pick up the plug base 18, as well as to prevent the tool 350 from being separating from the plug base 18 when anchoring the plug base 18 to the cranium of the patient.

The tool 350 also comprises a plurality of rotational alignment tabs 364 radially extending from the outer surface of the burr hole cover 352 in order to rotationally align the screw holder mechanisms 356 with the fastening holes 34 in the plug base 18, as well as to prevent the tool 350 from rotating or spinning in the aperture 26 of the plug base 18. In the illustrated embodiment, two rotational alignment tabs 364 are circumferentially disposed opposite each other, and are sized and shaped for being firmly disposed within the cap locking recesses 42 in the plug base 18. Alternatively, the tool 350 may include rotational alignment tabs (not shown) that are sized and shaped for being firmly disposed within the lead exit grooves 36 of the plug base 18.

The handle 354 is shaped such that the physician may ergonomically grasp it to prevent the tool 350 and the plug base 18 from moving when the plug base 18 is being anchored to the cranium of the patient. The handle 354 may have any one of a variety of shapes. In the embodiment illustrated in FIGS. 59-61, the handle 354 has a butterfly shape, thereby providing a broader base for the physician to apply a downward force on the plug base 18. The symmetry of the handle 354 allows the downward force to be applied equally to each side of the plug base 18, thereby preventing the tool 350 and the plug base 18 from rocking back and forth. The butterfly shape of the handle 354 also prevents the physician's hand from creating an obstruction for the fastening holes 34 of the plug base 18, the screw alignment mechanisms 356, or the screwdriver.

Figure 62:
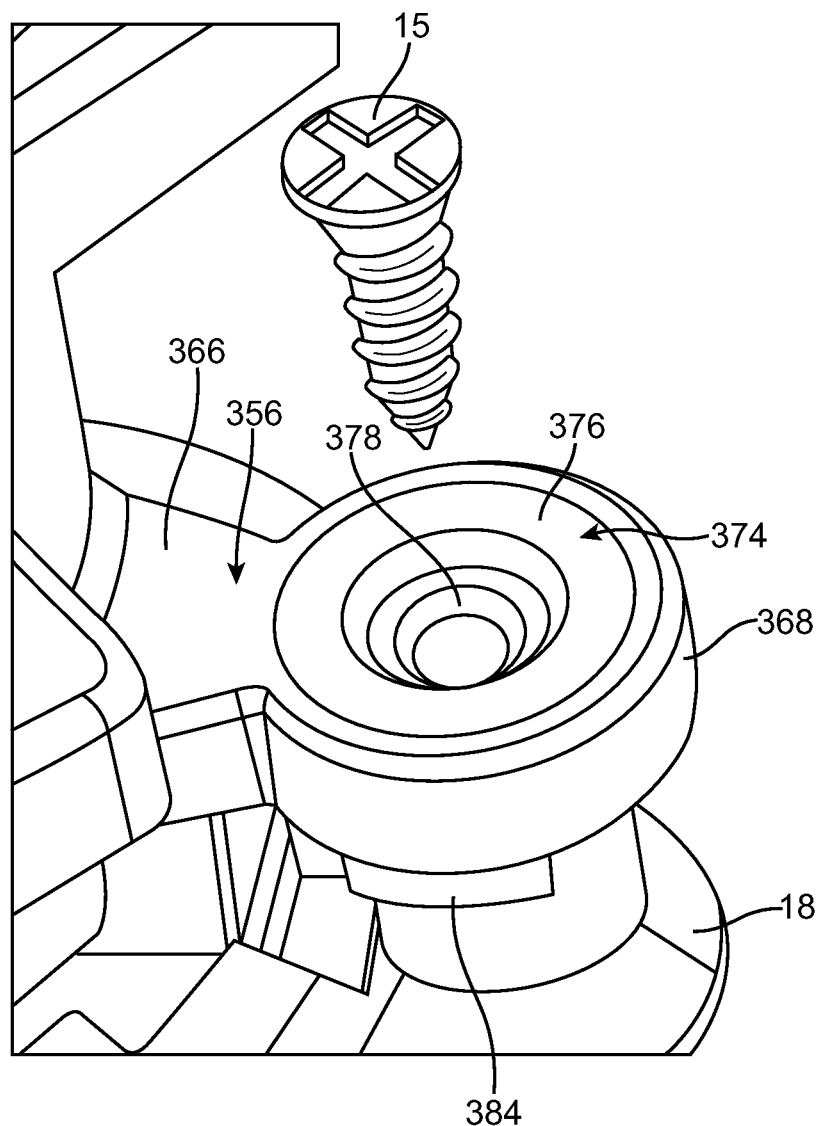
FIG. 62 is a top perspective view of a screw alignment mechanism of the plug base holding tool of FIG. 59.
Figure 63:
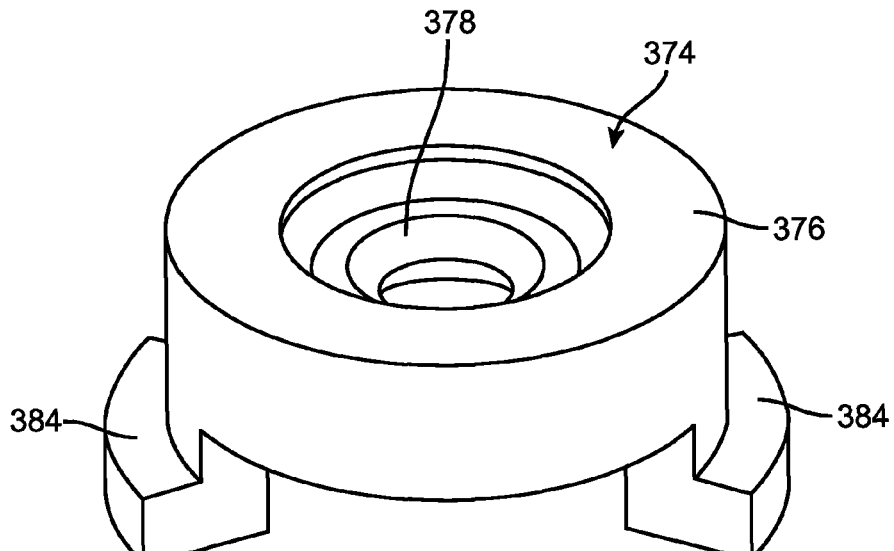
FIG. 63 is a top perspective view of an insert used in the screw alignment mechanism of FIG. 62.
Figure 64:
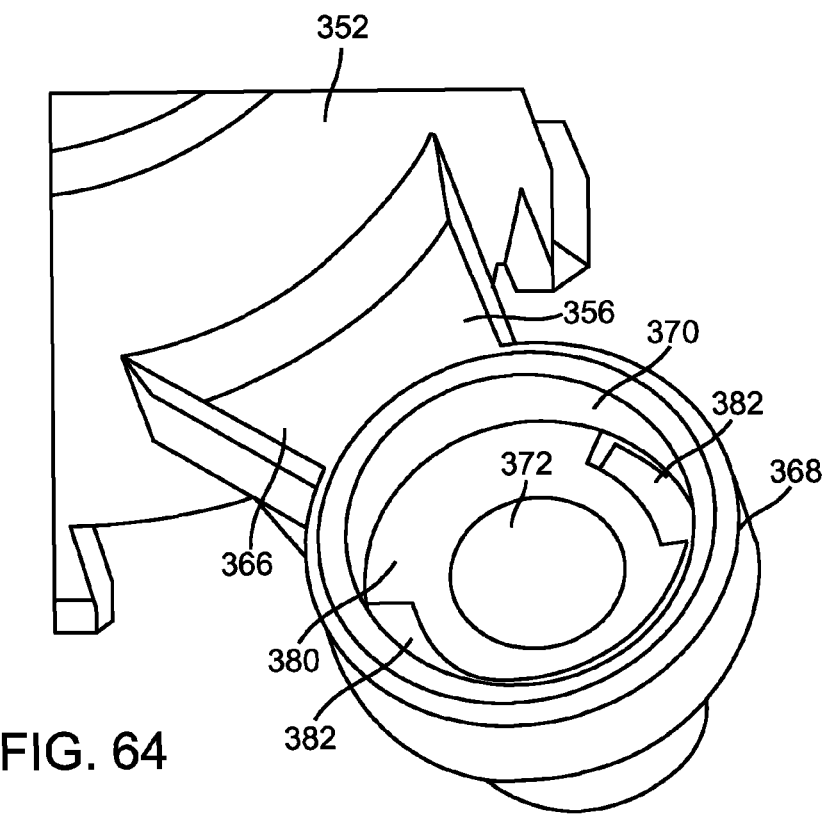
FIG. 64 is a top perspective view of a collar used in the screw alignment mechanism of FIG. 62.

Referring further to FIGS. 62-64, the screw alignment mechanisms 356 respectively include two arms 366 and collars 368 disposed at the ends of the arms 368. The collars 368 are spaced from each other, such that they respectively align with the fastening holes 34 located on the plug base 18 when the burr hole cover 352 is mounted within the plug base aperture 26. Thus, the screws 15 may be accurately inserted through the collars 368 and aligned with the fastening holes 34 in the plug base 18, such that the screws 15 can be conveniently screwed into the cranium of the patient. Each collar 368 has an upper large diameter bore 370 and a lower small diameter bore 372 in communication with the upper bore 370. The diameter of the lower bore 372 is equal to the outer diameter of the head of the screw 15, such that the screw 15 remains constantly centered with the respective fastening hole 34 in the plug base 18 as the head of the screw 15 passes through the bore 372.

Each screw alignment mechanism 356 includes an insert 374 disposed within the upper bore 370 of the collar 368. The insert 374 is composed of a flexible and pliable material, e.g., silicone. The insert 374 takes the form of a ring- or gasket-like structure that firmly holds and centers the respective screw 15 within the collar 368. In particular, as best shown in FIGS. 61 and 63, the insert 374 includes an outer ring 376 and an inner ring 378 concentrically disposed within the outer ring 376. Thus, the insert 374 effectively reduces the diameter of the upper bore 370, thereby facilitating the centering of the respective screw 15 before the head of the screw 15 passed into the lower bore 372. The pliability of insert 374 allows the head of the screw 15, which has a larger diameter than the inner diameter of the inner ring 378, to pass through the inner ring 378. The insert 374 also centers the screwdriver (not shown), both when it is introduced into the lower bore 372, and when it is removed and reentered into the lower bore 372. In the latter case, this makes it easier to align the screwdriver with the head of the screw 15. Optionally, there may be a metal insert (not shown) within the collar 368 to prevent plastic from being scraped off.

As best shown in FIGS. 63 and 64, each collar 368 has a ledge 380 between the upper and lower bores 370, 372, and a pair of circumferentially opposing slots 382 formed through the ledge 380, and the respective insert 374 includes a pair of circumferentially opposing retaining tabs 384 extending from the bottom of the outer ring 376. Each tab 384 extends downward from the bottom of the outer ring 376 and then radially outward. Thus, when the insert 374 is mounted within the upper bore 370, the tabs 384 of the insert 374 are respectively disposed through the slots 382 in the ledge 380 of the collar 368, thereby firmly retaining the insert 374 with the upper bore 370.

Figure 65:
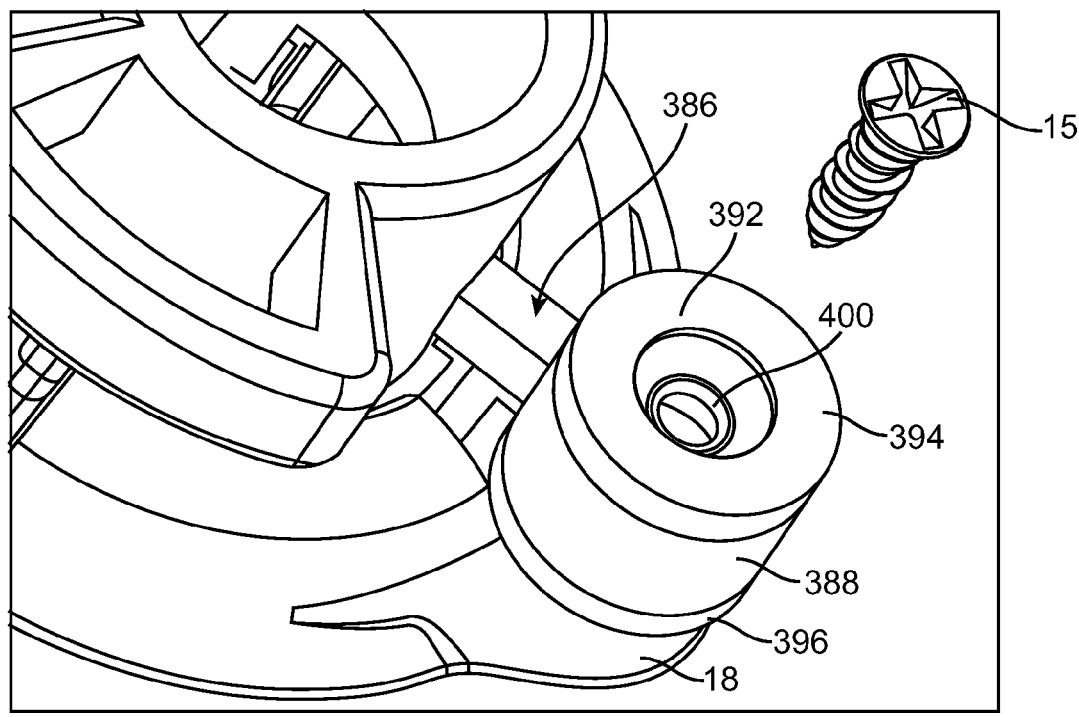
FIG. 65 is top close-up perspective view of an alternative screw alignment mechanism that can be used with the plug base holding tool of FIG. 59.
Figure 66:
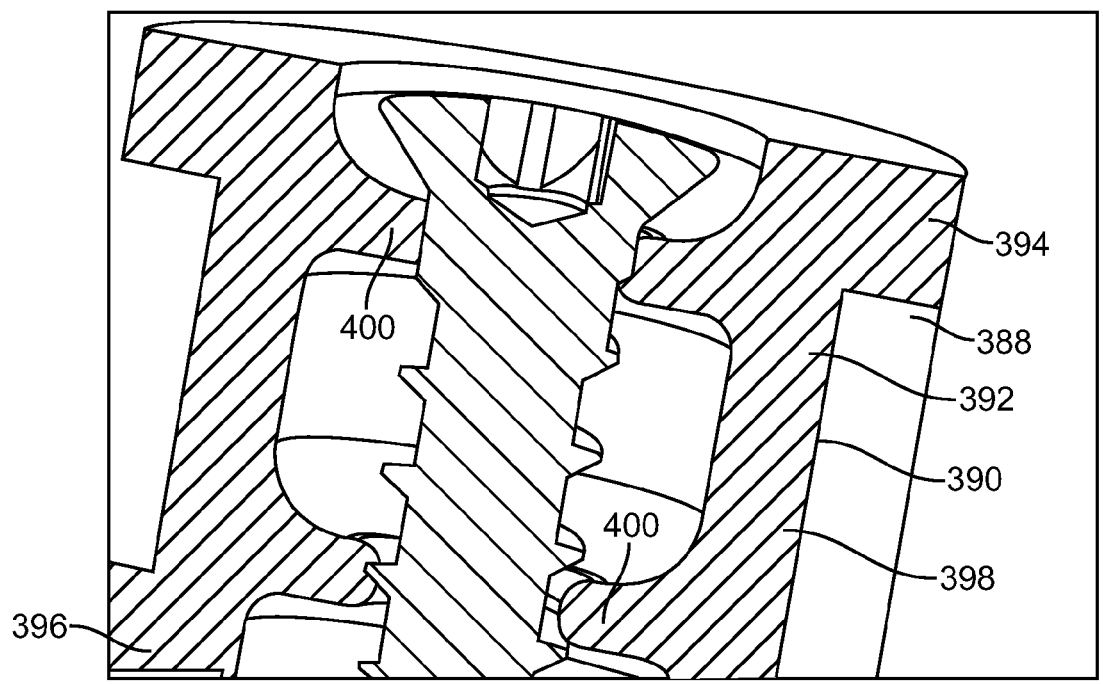
FIG. 66 is a cross-sectional close-up view of the screw alignment mechanism of FIG. 65.

In an alternative embodiment illustrated in FIGS. 65 and 66, the tool 350 comprises a screw alignment mechanism 386 that includes a collar 388 having a bore 390 with a uniform diameter extending therethrough. The screw alignment mechanism 386 also comprises an insert 392 that, like the previously described insert 374, is composed of a flexible and pliable material, e.g., silicone. The insert 392 has an upper annular flange 394, a lower annular flange 396, and a smaller diameter cylindrical portion 398 extending between the upper and lower annular flanges 394, 396. The insert 392 is configured for being mounted within the collar 388, such that the cylindrical portion 398 is disposed within the bore 390 of the collar 368, and the upper and lower annular flanges 394, 396 are respectively disposed on the upper and lower surfaces of the collar 368 to firmly retain the cylindrical portion 398 within the bore 390.

As best shown in FIG. 66, the insert 392 includes a plurality of inner rings 400 (in this case, two) concentrically disposed along the length of the cylindrical portion 398. Thus, the inner diameters of the inner rings 400 are equal to the outer diameter of the screw 15, thereby facilitating the centering of the respective screw 15 within the bore 390 of the collar 388. The pliability of the insert 392 allows the head of the screw 15, which has a larger diameter than the inner diameter of the inner rings 400, to pass through the inner rings 400. The insert 392 also centers the screwdriver (not shown), both when it is introduced into the bore 390, and when it is removed and reentered into the bore 390. In the latter case, this makes it easier to align the screwdriver with the head of the screw 15.

Figure 67:
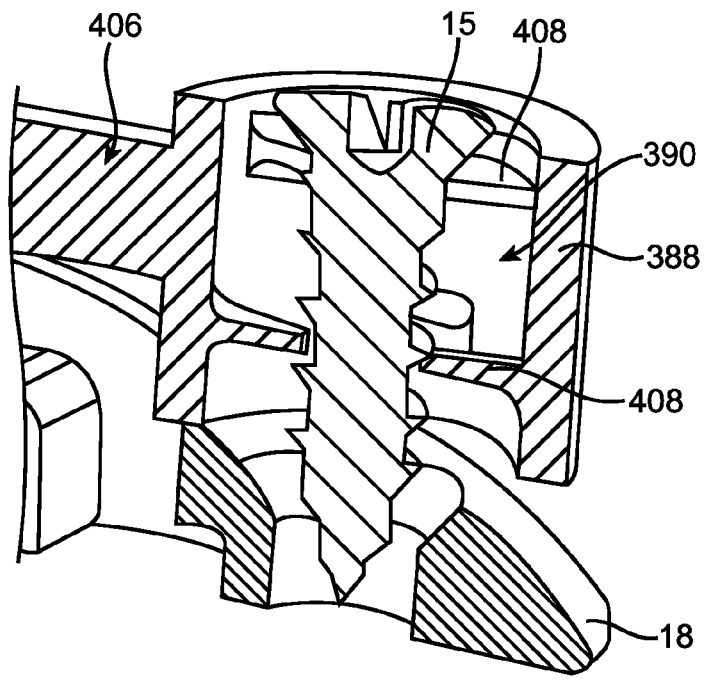
FIG. 67 is a cross-sectional view of another alternative screw alignment mechanism that can be used with the plug base holding tool of FIG. 59.
Figure 68:
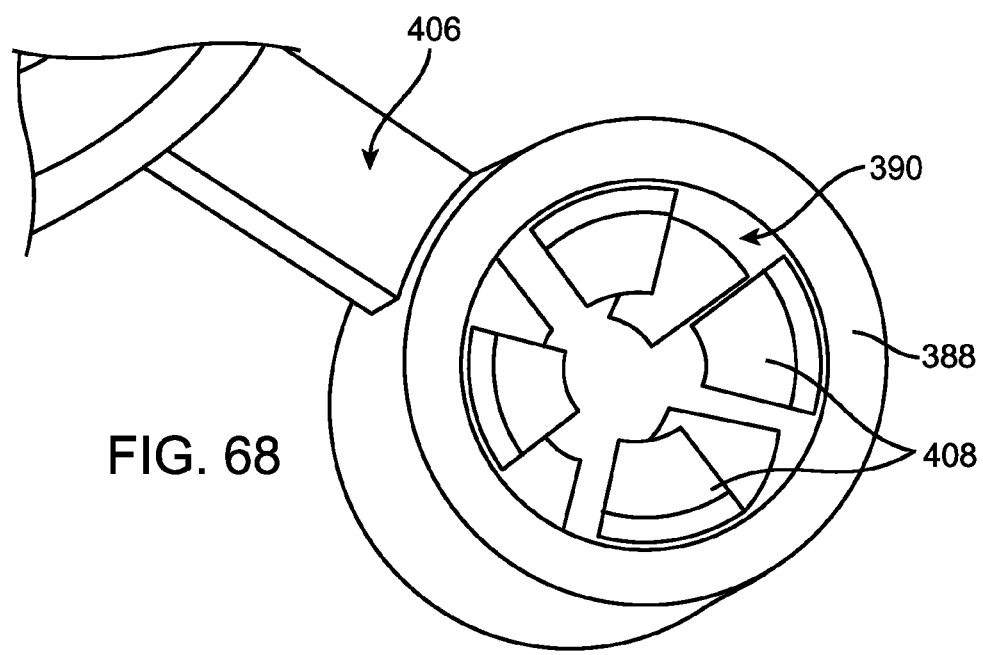
FIG. 68 is a top perspective view of the screw alignment mechanism of FIG. 67.

In another alternative embodiment illustrated in FIGS. 67 and 68, the tool 350 comprises a screw alignment mechanism 406 includes the previously described collar 388 and a plurality of tabs or flanges 408 radially extending inward around the inner circumference of the collar 388 into the bore 390. The radial tabs 408 may be formed as a unibody structure with the collar 388, and are thin enough, such that they will bend without breaking as the screw 15 passes through the bore 390 of the collar 388. Alternatively, the radial tabs 408 may be composed of a material that is more flexible or pliable than the material from which the collar 368 is composed. As can be appreciated, the radial tabs 408 effectively reduce the diameter of the bore 390 of the collar 368, thereby facilitating the centering of the respective screw 15 within the bore 390. The pliability of radial tabs 408 allows the head of the screw 15 to pass through the bore 390. The radial tabs 408 may also center the screwdriver (not shown) in the same manner as the inner rings 400 of the insert 392 described above. In the illustrated embodiment, the radial tabs 408 are arranged in several layers (in this case two layers of four tabs each) extending inward along the length of collar 368 within the bore 390.

Figure 70:
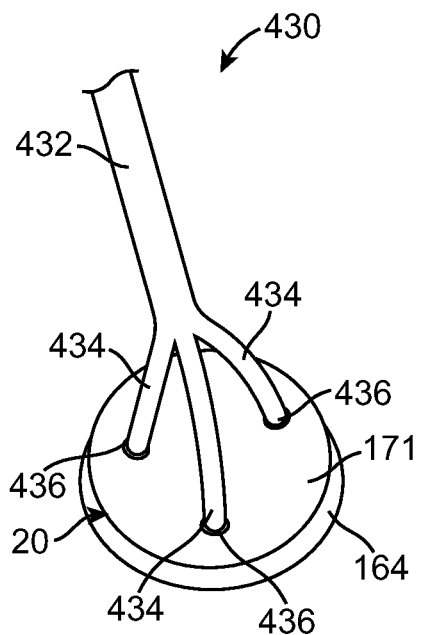
FIG. 70 is a top perspective view of one embodiment of a retainer holding tool engaged with a retainer.
Figure 71:
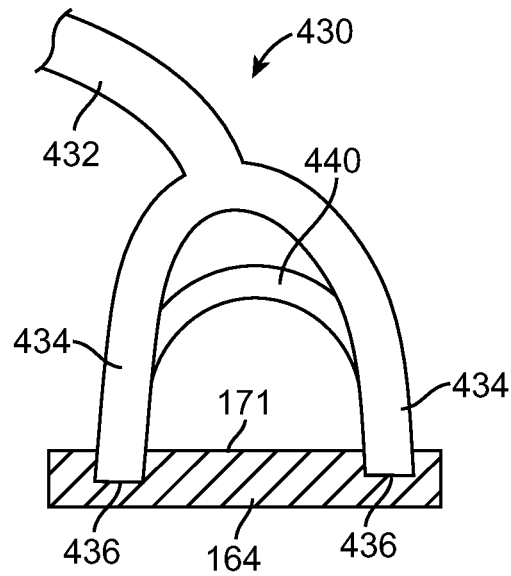
FIG. 71 is a side view of the retainer holding tool of FIG. 70.

Referring next to FIGS. 70 and 71, one embodiment of a retainer holding tool 430 configured for mounting the retainer 20 within the aperture 26 of the plug base 18 (shown in FIG. 8) will now be described. The retainer holding tool 430 generally comprises a handle 432 and a plurality of fingers 434 extending from the handle 432 and configured for engaging connection points 436 on the top surface 171 of the retaining disk 164. The tool 430 may be composed of a suitable rigid and robust material, such as stainless steel or a durable plastic, such as polypropylene, polycarbonate, or even if PEEK if very little deformation is desired. The handle 432 is angled relative to the fingers 434 in order to facilitate the manipulation, navigation, and placement of the retainer 20 in tight spaces; for example, due to its angle relative to the plane of the retainer 20 that it supports, the movement of the handle 432 may not be obstructed by equipment immediately above the burr hole.

The distal ends of the fingers 434, and thus the contact points 436 on the top surface 171 of the retaining disk 164, are spaced from each other in a manner that substantially distributes any downward force applied by the tool 430 across the plane of the retaining disk 164 when mounted within the plug base aperture 26. In the embodiment illustrated in FIGS. 70 and 71, the distal ends of three fingers 434 are engaged with contact points 436, and in particular, small recesses or possibly holes, formed in the top surface 171 of the retaining disk 164. The fingers 434 of the tool 430 are configured to engage the recesses 436 in an interference arrangement, e.g., a snap-fit arrangement. As will be described in further detail below, the retention force between the fingers 434 of the tool 430 and the retainer 20 should be less than the retention force between the retainer 20 and the plug base 18, so that the tool 430 can be easily removed from the retainer 20 when mounted within the plug base 18.

Figure 72:
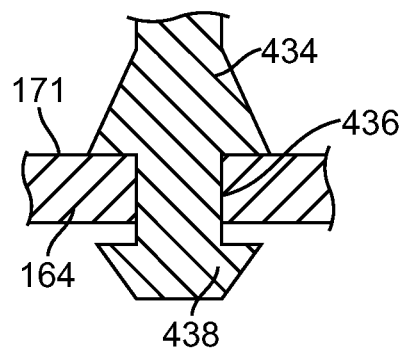
FIG. 72 is a cross-sectional view of one leg of the retainer holding tool engaged with the retainer.

Preferably, this interference arrangement is sufficient enough to provide a firm engagement between the tool 430 and the retainer 20, but should be capable of being overcome after the retainer 20 is mounted within the plug base 18, so that the tool 430 can be easily removed from the retainer 20, while leaving the retainer 20 firmly mounted within the plug base 18. For example, as illustrated in FIG. 72, the recesses 436 may be formed entirely through the thickness of the retaining disk 164, and the distal ends of the fingers 434 may have barbs 438 that extend through the recesses 436 and engage the bottom surface of the retaining disk 164. The size of the barbs 438 should be designed, such that they remain within the recesses 436 during normal manipulation, navigation, and placement of the retainer 20, but should be capable of being displaced through the recesses 436 when the tool 430 is removed from retainer 20; that is, the upward force required to pull the barbs 438 through the recesses 436 should be less than the upward force required to remove the firmly mounted retainer 20 from the plug base 18. The portions of fingers 434 above the recesses 436 may be flared or increased to provide a more stable base that more uniformly distributed the downward force across the top surface 171 of the retaining disk 164.

In one preferred embodiment, the fingers 434 are resiliently flexible, so that they store a spring force when engaged with the recesses 436 on the retaining disk 164. In this case, the spacing between the distal ends of the fingers 434, in the absence of any lateral force, is slightly less than the spacing between the recesses 436 on the retaining disk 164. In this manner, the fingers 434 will act as biased springs when engaged with the recesses 436, thereby providing an additional grasping force that strengthens the engagement with the retainer 20. That is, the fingers 434 will slightly spread out when located within the recesses 436, thereby creating a spring force that laterally urges or biases the fingers 434 inward within the recesses 436 to create a frictional force that facilitates engagement between the fingers 434 and the recesses 436. The fingers 434, as well as the handle 432, may be composed of a suitable resilient material, such as, polypropylene, polycarbonate, etc. Alternatively, the tool 430 may be provided with a separate spring-like mechanism 440 engaged between the fingers 434, as illustrated in FIG. 71. In alternative embodiments, the proximal end of the tool 430 may be designed to perform another function, such as moving the clamping mechanism 162 or popping out the retainer 20 from the plug base 18.

Figure 73:
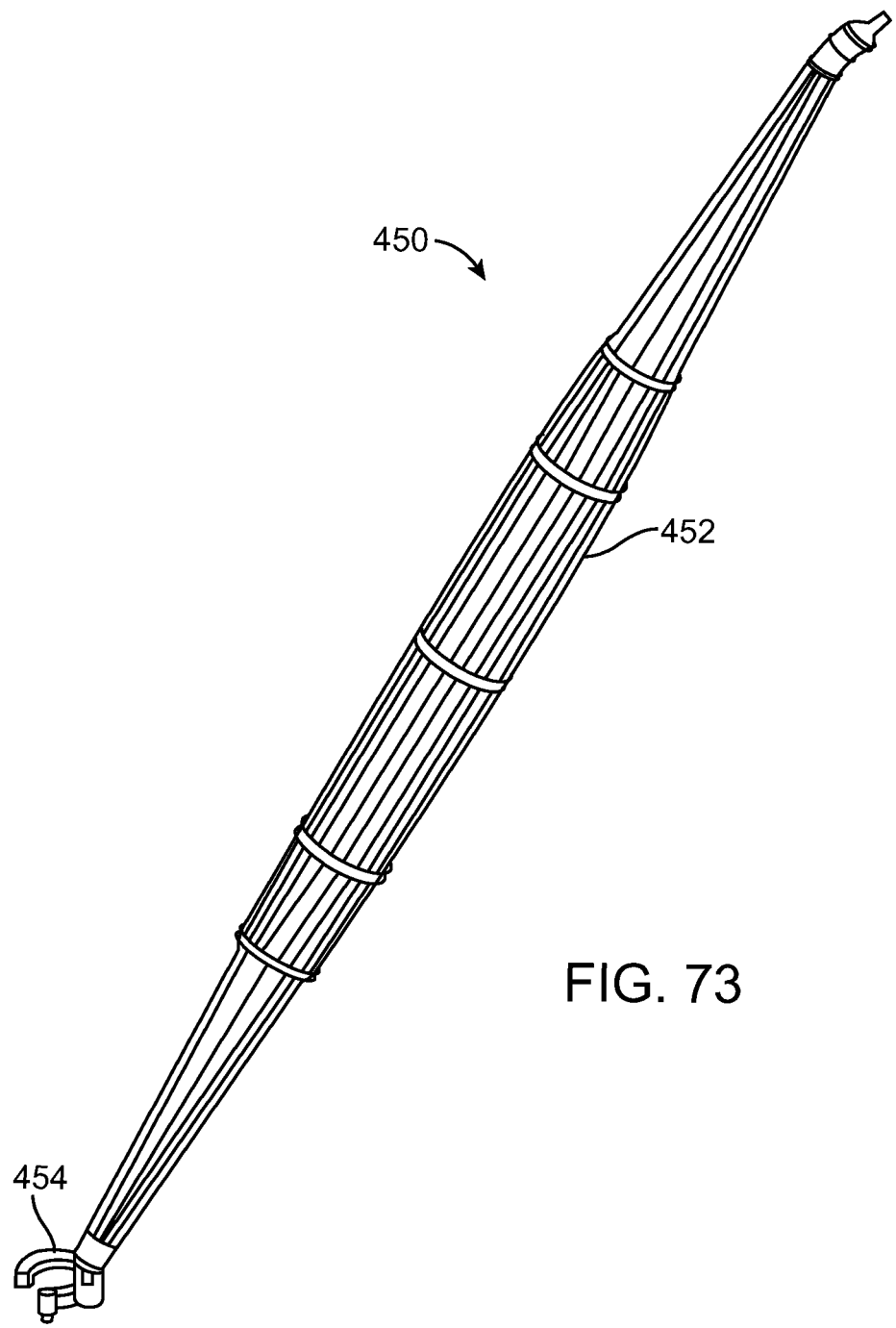
FIG. 73 is a perspective view of another embodiment of a retainer holding tool.
Figure 74:
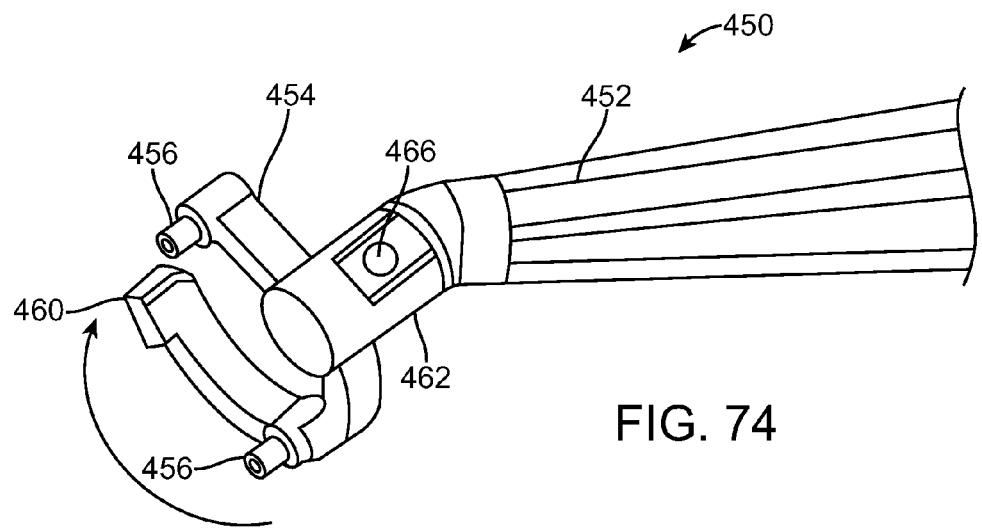
FIG. 74 is a perspective view of the retainer holding mechanism of the retainer holding tool of FIG. 73.
Figure 75:
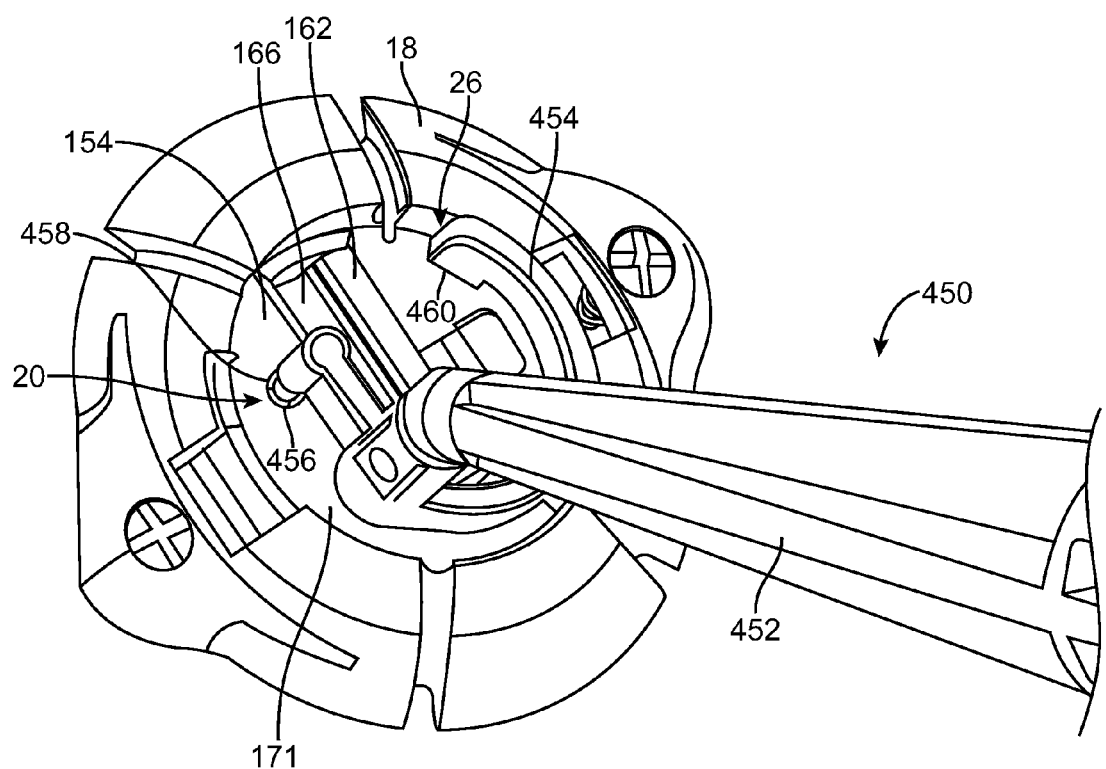
FIG. 75 is a close-up perspective view of the retainer holding tool of FIG. 73, particularly shown mounting the retainer of FIG. 28 with the plug base of FIG. 8.

Referring to FIGS. 73-75, another retainer holding tool 450 configured for mounting the retainer 20 within the aperture 26 of a plug base 18 will now be described. The holding tool 450 is specifically designed as to not interfere with the stimulation lead when the retainer 20 is mounted within the plug base aperture 26. In particular, the holding tool 450 generally comprises a handle 452, a C-shaped flange 454, and pegs 456 extending downward from the C-shaped flange 454. The tool 450 may be composed of a suitable rigid and robust material, such as stainless steel or a durable plastic, such as polypropylene, polycarbonate, or even if PEEK if very little deformation is desired.

In the illustrated embodiment, two pegs 456 are provided on the C-shaped flange 454, one located on one end of the C-shaped flange 454 and the other one located near the center of the C-shaped flange 454. Optionally, a third peg (not shown) can be provided on the other end of the C-shaped flange 454. The pegs 456 are spaced from each other, such that they engage with contact points, and in particular, corresponding recesses or holes 458 (only one show in FIG. 75) formed in the top surface 171 of the retaining disk 164. The pegs 456 of the tool 430 are configured to engage the recesses 458 in an interference arrangement, e.g., a frictional fit. The retention force between the pegs 456 of the tool 430 and the retainer 20 should be less than the retention force between the retainer 20 and the plug base 18, so that the tool 450 can be easily removed from the retainer 20 when mounted within the plug base 18. As with the previously described fingers 434, the spacing between the pegs 456 may be slightly less than the spacing between the recesses 458 to increase the frictional force between the pegs 456 and the recesses 458; that is, a spring force is stored in the pegs 456 to urge them inward when engaged with the recesses 458. Optionally, to strengthen the interference fit, the pegs 456 may have barbs (not shown) and the recesses 458 may be formed all the way through the thickness of the disk 164 in the same manner described above with respect to the tool 430.

As can be appreciated from FIG. 75, the C-shaped flange 454 accommodates the stimulation lead exiting the burr hole. That is, the C-shaped flange 454 is sized and shaped, such that it extends around or near the outer periphery of the disk 164 without obstructing the clamping slot 166, and the corresponding recesses 458 are similarly disposed on or near the outer periphery of the disk 164. The tool 450 further comprises a support tab 460 located on the end of the C-shaped flange 454 opposite the peg 456, thereby facilitating the application of uniform pressure on the disk 164 when mounted within the plug base aperture 26 by the tool 450. In an optional embodiment, the U-shaped flange 454 is configured for rotating about the axis of the handle 452 (shown by the arrow in FIG. 74).

Figure 76:
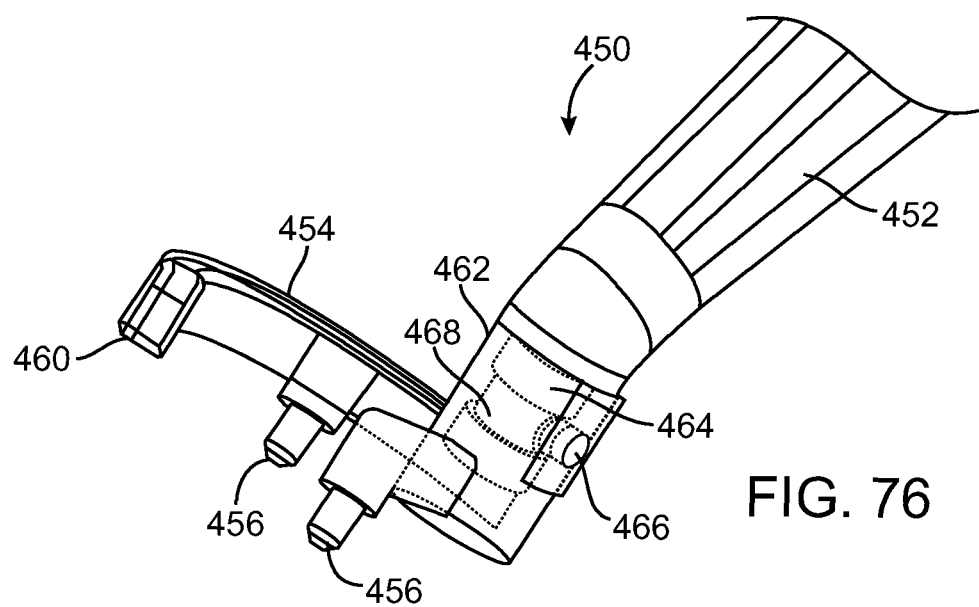
FIG. 76 is a perspective view of the retainer holding mechanism of FIG. 74, particularly showing the retainer holding mechanism in phantom.

To this end, and as best shown in FIG. 76, the tool 450 further comprises a collar 462 mounted perpendicularly to the C-shaped flange 454 (both shown in phantom), and the handle 452 includes a reduced diameter boss 464 received within the collar 462, so that the collar 462, and thus, the C-shaped flange 454, may rotate about the handle 452. The reduced diameter boss 464 of the handle 452 is configured for being interference fit within the collar 462, such that the collar 462 and the C-shaped flange 454 does not separate when detaching the pegs 456 from the corresponding recesses 458 in the disk 164. To this end, the tool 450 further comprises a movable pin 466 disposed within the side wall of the collar, and the reduced diameter boss 464 has an annular recess 468 that receives the pin 466. The pin 466 may be composed of a suitable material, e.g., stainless steel. It can be appreciated that the pin 466 can slide with the annular recess 468, thereby allowing the collar 462, and thus, the C-shaped flange 454, to rotate about the axis of the handle 452. Because the pin 466 is firmly seated within the annular recess 468, however, the C-shaped flange 454 cannot be removed from the handle 452 without using a significant amount of axial force. Notably, the pin 466 frictionally engages the annular recess 468, such that the C-shaped flange 454 does not freely spin; that is, the C-shaped flange 454 will not rotate relative to the handle 452 without applying a deliberate force to the C-shaped flange, e.g., by being rotated by hand.

Figure 77:
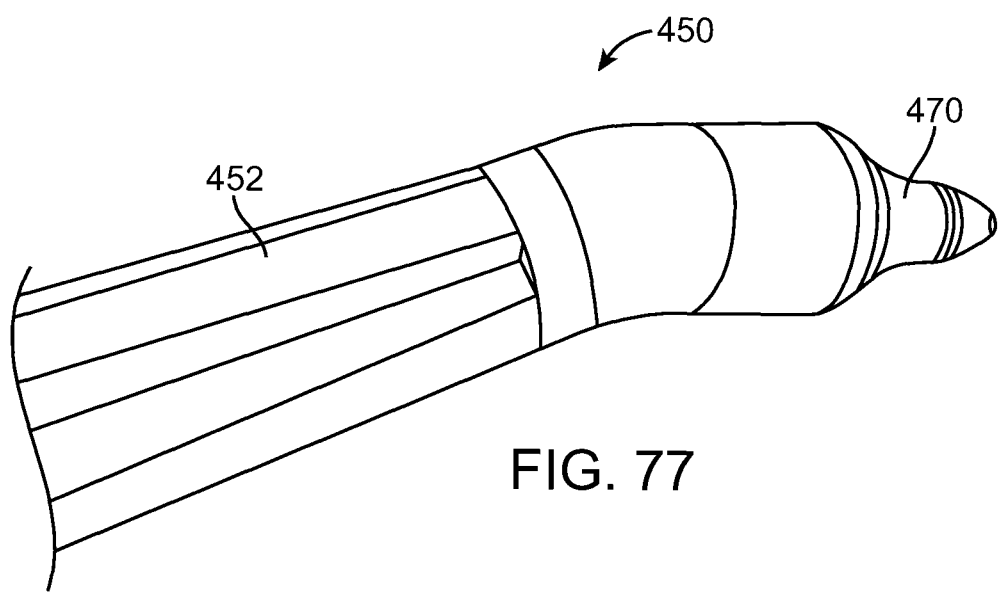
FIG. 77 is a close-up view of a blunt tip of the retainer holding tool of FIG. 73.

Notably, the handle 452 is angled relative to the C-flange 454 in order to facilitate the manipulation, navigation, and placement of the retainer 20 in tight spaces. That is, due to its angle relative to the plane of the retainer 20 that it supports, the movement of the handle 452 may not be obstructed by equipment immediately above the burr hole. To this end, the distal end of the handle 452 to which the collar 462 is mounted has a bend (e.g., a 45 degree or a 60 degree angle between the collar 462 and the handle 452) to effect the angling of the handle 452 relative to the C-flange 454. The distal end of the handle 452 may optionally be made malleable to allow the physician to create the optimum angle for insertion of the retainer 20 into the plug base aperture 26. The proximal end of the tool 450 may be designed to perform another function, such as locking or unlocking the clamping mechanism 162 or popping the retainer 20 out from the plug base 18. For example, as illustrated in FIG. 77, a tapered blunt tip 470 can be formed on the proximal end of the handle 452.

Referring to FIGS. 78-80, still another retainer holding tool 480 configured for mounting the retainer 20 within the aperture 26 of a plug base 18 (shown in FIG. 75) will now be described. Like the tool 450 previously described above, the tool 480 may be composed of a suitable rigid and robust material, such as stainless steel or a durable plastic, such as polypropylene, polycarbonate, or even if PEEK if very little deformation is desired. The tool 480 comprises a handle 482 that is of a similar construction as the handle 452, and a radially compressible/resilient tip 484 that can be inserted into any one of the recesses 458 formed on the top surface 171 of the retaining disk 164 illustrated in FIG. 75. The outer radius of the tip 484 is slightly larger than the radius of each recess 458, such that, when the tip 484 is inserted into the recess 458, the tip 484 radially compresses. The resiliency of the tip 484 applies a radially outward force against the inner wall of the recess 458, thereby creating a frictional interference fit that holds the retainer 20 on the tool 480.

In the illustrated embodiment, the tip 484 takes the form of a spring mechanism, and in particular a spring clip, that includes a pair of parallel arms 486 that move toward each other from a relaxed position to a compressed position in response to a compressive force, and move away from each other from the compressed position to the relaxed position in the absence of the compressive force. The tool 480 comprises a collar 488 formed at the distal end of the handle 482 for retaining the tip 484. In particular, the collar 488 includes a receptacle 490 that receives the arms 486 of the tip 484 in an interference arrangement. Specifically, the collar 488 is split or forked to form a pair of opposing annular flanges 492 that respectively receive the arms 486 of the tip 484 therein. The tip 484 can be arranged as an insert that can be passed through a distal aperture 494 of the receptacle 490. Once inserted within the receptacle 494, the resiliency of the tip 484 will cause the arms 486 to be urged radially outward away from each other into firm contact with the respective annular flanges 492, thereby mounting the tip 484 to the handle 482. In this state, the tip 484 will be partially radially compressed. When the tip 484 is inserted into the recess 486 of the retaining disk 164, the tip 484 will be further radially compressed within the recess 486 to create the aforementioned frictional fit. To prevent the tip 484 from axially moving out of the receptacle 490 during such compression, the tip 484 further comprises a pair of radially outward tabs 496 respectively formed on the ends of the arms 484. The distal end of the handle 482 further includes corresponding recesses 498 for receiving and holding the tabs 496 therein.

Figure 69:
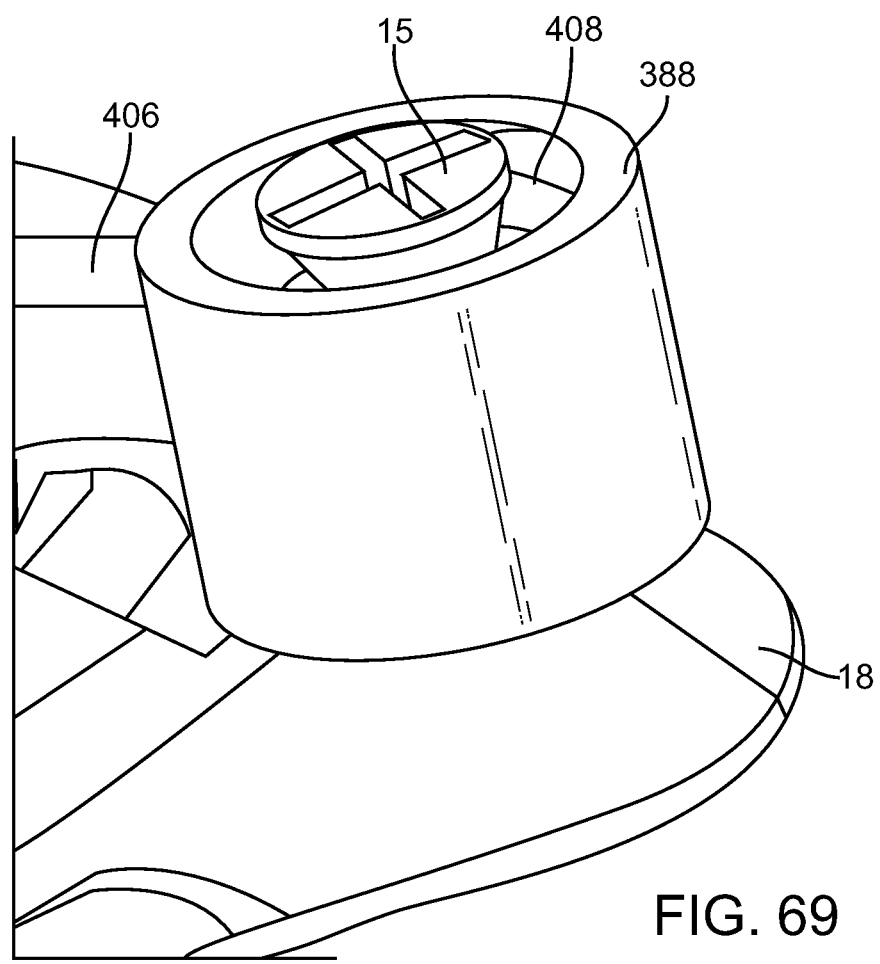
FIG. 69 is a top perspective view of the screw alignment mechanism of FIG. 67, particularly showing the screw mounted disposed within the collar.

Having described the structure and function of the burr hole plug 16 and tools used with burr hole plugs into a burr hole, a method of mounting the burr hole plug 16 into a burr hole will now be described. Referring first to FIG. 81, the plug base 18 is placed on top of the cranium 6 of the patient. Notably, the centering tabs 32 located on the plug base 18 can be disposed within the burr hole 5, thereby centering the plug base 18 about the burr hole 5. If the recessed plug base 57 illustrated in FIGS. 10-13 is used, the annular flange 45 will also be recessed into the burr hole 5, as illustrated in FIG. 82, to allow the retainer 20 to be recessed further down into the burr hole. Referring back to FIG. 81, the plug base 18 is then anchored to the cranium 6 using the screws 15 introduced through the screw holes 34 in the plug base 18. Any of the plug base anchoring tools 300 (FIGS. 54-58), 350 (FIG. 59-68), or 410 (FIG. 69) can be used to align the screws 15 with the screw holes 34 while covering the aperture 26 in the plug base 18, and if self-centering tabs are not provided on the plug base 18, can aid in centering the plug base 18 relative to the burr hole 5.

Figure 83:
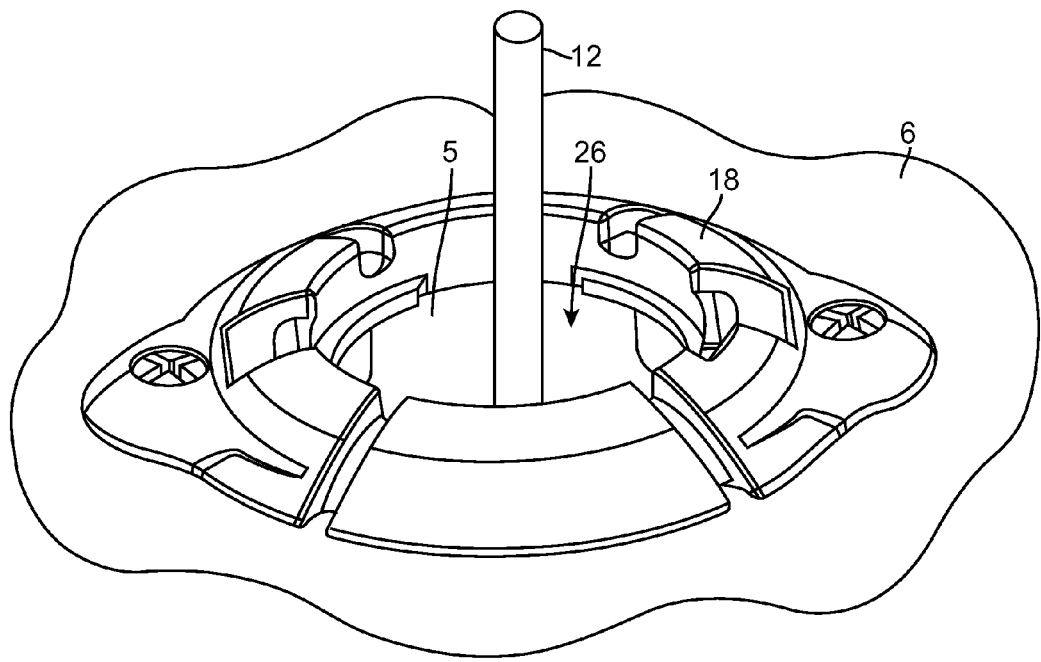
FIG. 83 is a perspective view of the mounted plug base of FIG. 81, particularly showing a stimulation lead disposed through the aperture of the plug base.
Figure 84:
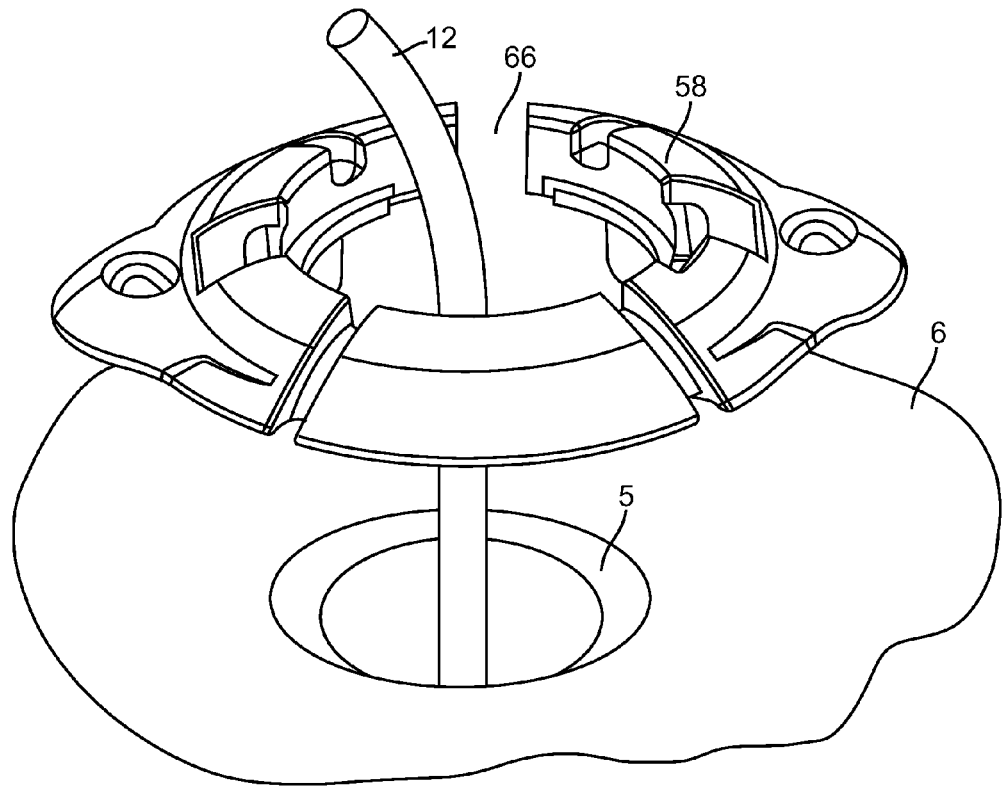
FIG. 84 is a perspective view of the plug base of FIG. 16 prior to mounting within a burr hole, particularly showing a stimulation lead disposed through the aperture of the plug base.
Figure 85:
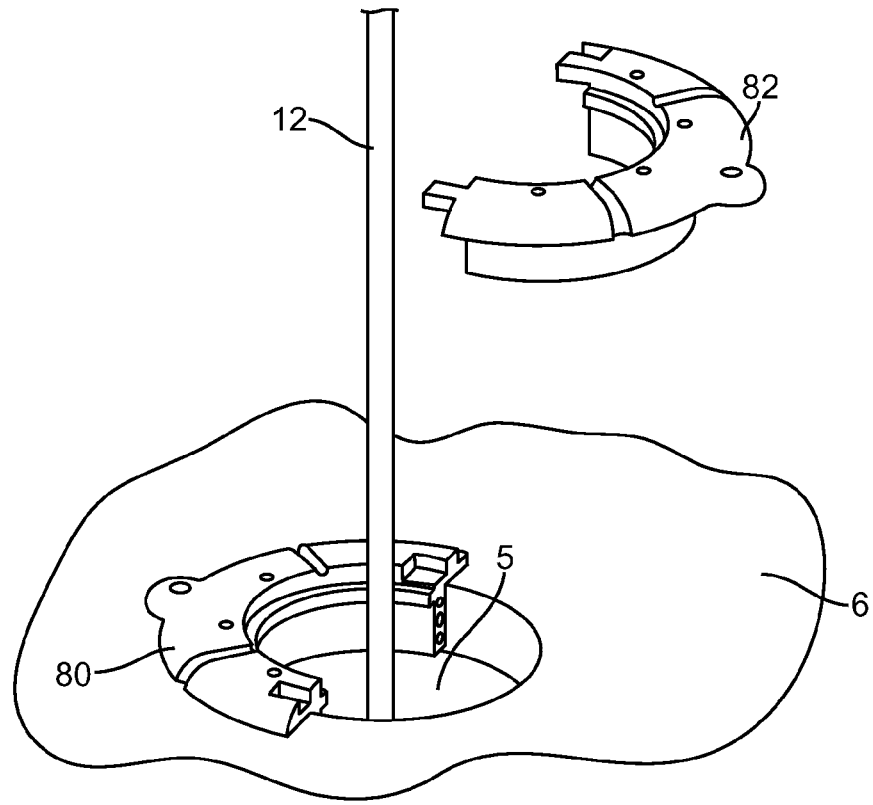
FIG. 85 is a perspective view of one portion of the plug base of FIG. 17 mounted within a burr hole.
Figure 86:
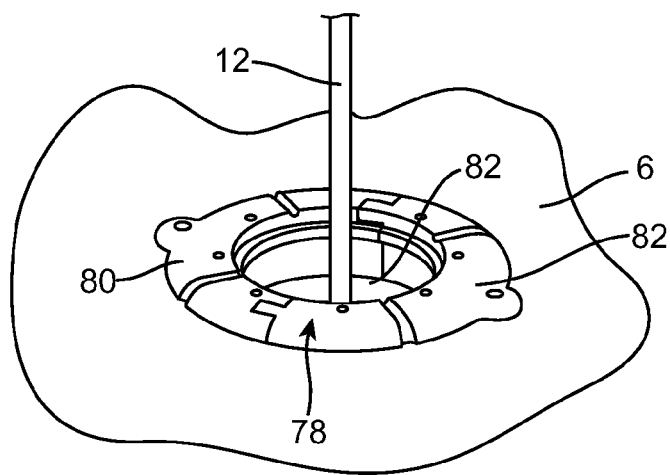
FIG. 86 is a perspective view of the remaining portion of the plug base of FIG. 17 mounted within the burr hole.

Next, as illustrated in FIG. 83, the stimulation lead 12 is introduced through the plug base aperture 26, through the burr hole 5, and into the brain tissue, such that the electrodes (not shown) of the stimulation lead 12 are adjacent the target site. In the case where the slotted plug base 58 illustrated in FIG. 16 is used, the stimulation lead 12 may first be introduced through the burr hole 5, the stimulation lead 12 can be laterally introduced within the slot 66 of the plug base 58, as illustrated in FIG. 84, and then the plug base 58 can be disposed over and anchored to the cranium 6 in the same manner described above with respect to FIG. 81. In the case where the split plug base 78 illustrated in FIGS. 17 and 18 is used, the stimulation lead 12 may first be introduced through the burr hole 5 and the first plug base portion 80 can be located adjacent to one side of the stimulation lead 12, the second plug base portion 82 can be located adjacent to the other side of the stimulation lead 12, and then the first and second plug base portions 80, 82 can be mated together to integrate the plug base 78. This can be accomplished by locating the first plug base portion 80 onto the cranium 6 adjacent the one side of the stimulation lead 12, as illustrated in FIG. 85, and then placing the second plug base portion 82 onto the first plug base portion 80 adjacent the other side of the stimulation lead 12, as illustrated in FIG. 86. If the first and second plug base portions 80, 82 are initially coupled together using the complementary pins 100 and recesses 102, the pins 100 can be sheared off prior to mating the base portions 80, 82 together. After mating the base portions 80, 82 together, the integrated plug base 78 can then be anchored to the cranium 6 in the same manner described above with respect to FIG. 81. Of course, the slotted plug base 58 or the split plug base 78 can be anchored to the cranium 6 before the stimulation lead 12 is introduced through the burr hole 5 in the same manner described above with respect to the plug base 18.

Figure 87:
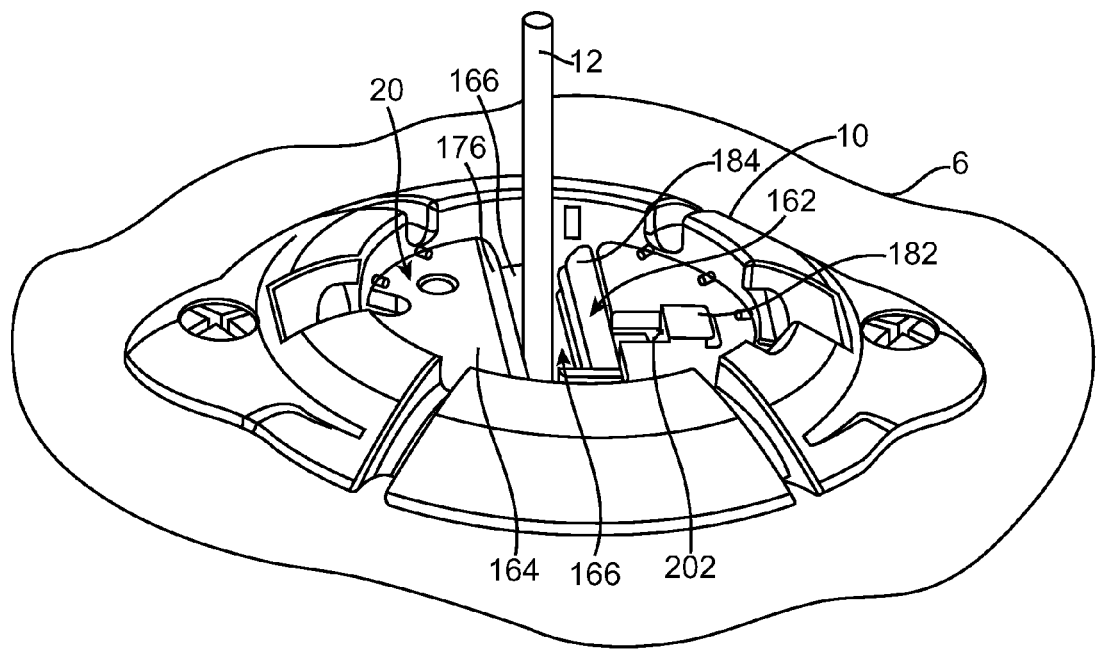
FIG. 87 is a perspective view of the retainer of FIG. 28 mounted within the plug base shown in FIG. 83, particularly showing the clamping mechanism in an open position.
Figure 88:
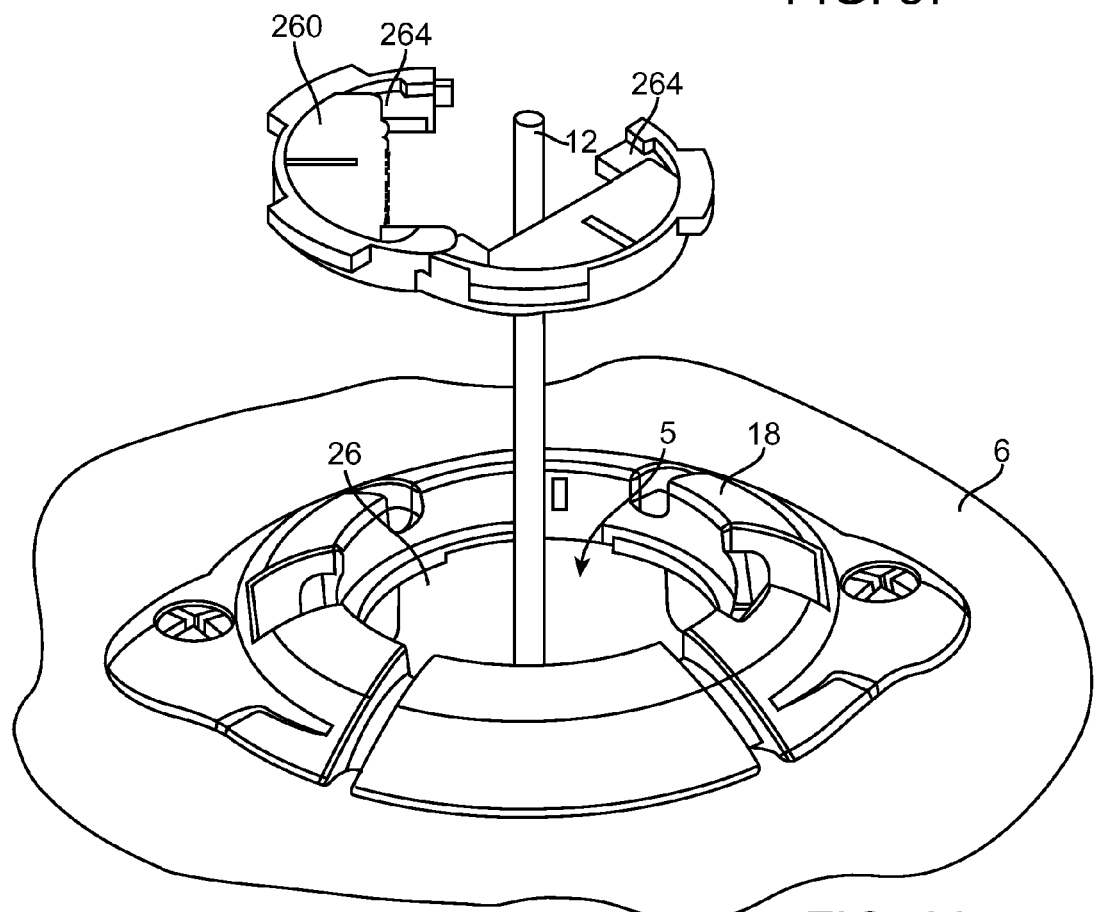
FIG. 88 is a perspective view of the clamping mechanism of FIG. 48 prior to mounting within the plug base shown in FIG. 83, particularly showing the clamping mechanism in an unclamped position.
Figure 89:
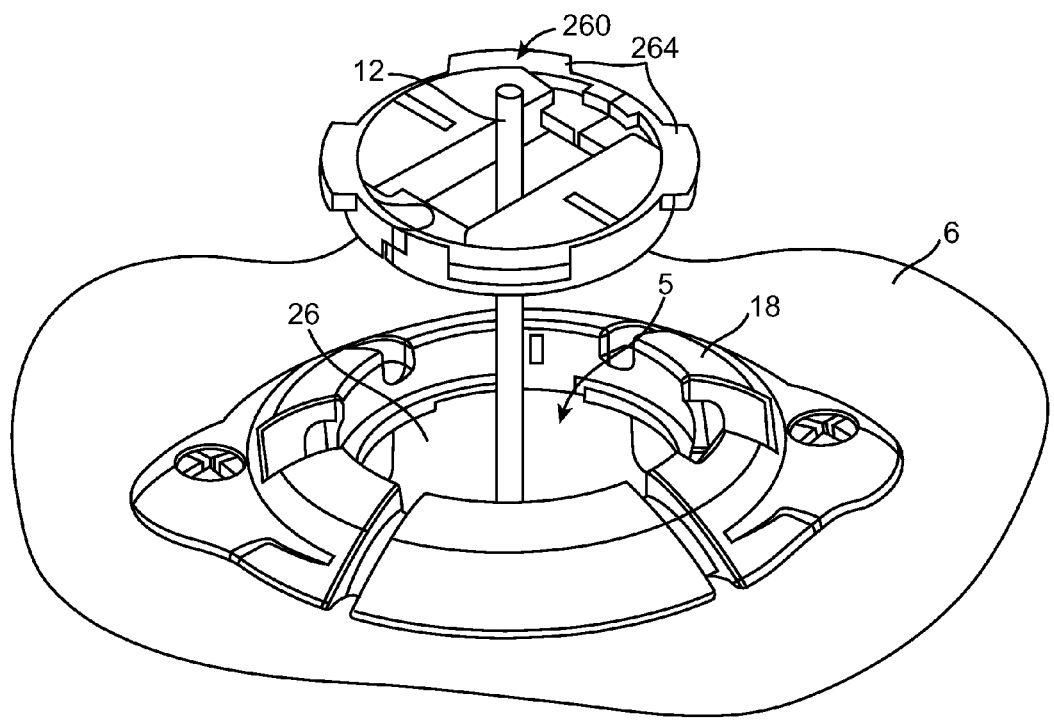
FIG. 89 is a perspective view of the clamping mechanism of FIG. 48 prior to mounting within the plug base shown in FIG. 83, particularly showing the clamping mechanism in a clamped position.

After the plug base 18 has been anchored to the cranium 6 and the stimulation lead 12 introduced through the burr hole 5 and properly located adjacent the target site, the retainer 20 is mounted within the plug base aperture 26, as illustrated in FIG. 87. The stimulation lead 12 can be laterally introduced within the slot 166 formed in the retaining disk 164 as the retainer 20 is mounted to the plug base 18. In the case, where the hinged retainer 260 illustrated in FIGS. 48 and 49 is used, the first and second disk portions 264 can be hinged open to laterally receive the stimulation lead 12, as illustrated in FIG. 88, and then hinged closed to encompass the stimulation lead 12, as illustrated in FIG. 89. Any of the retainer placement tools 430 (FIGS. 70-72), 450 (FIGS. 73-77), or 480 (FIGS. 78-80) can be used to place and mount the retainer 20 (or retainer 260) within the plug base aperture 26.

Figure 90:
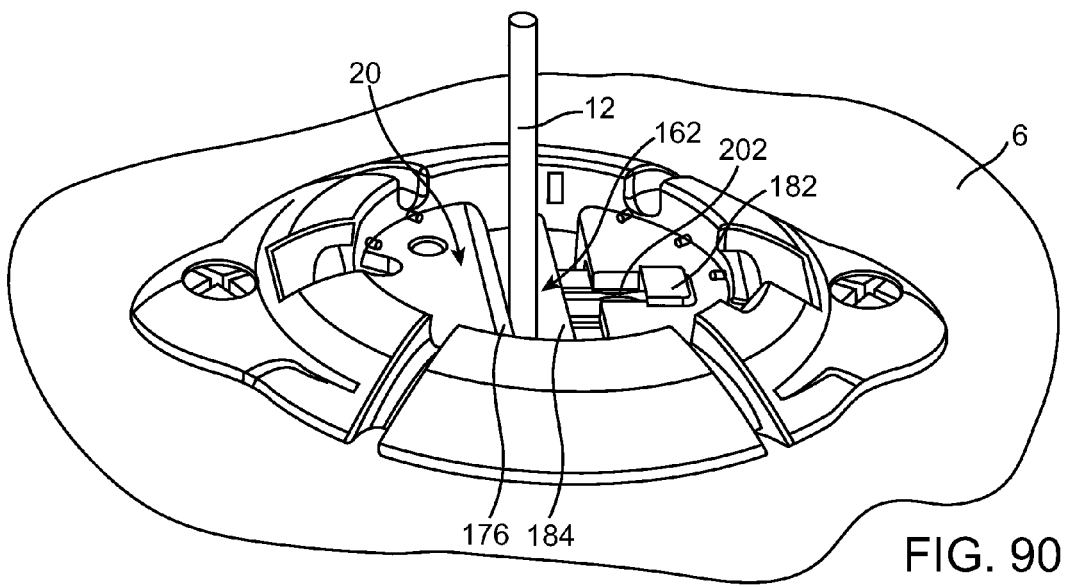
FIG. 90 is a perspective view of the retainer of FIG. 28 mounted within the plug base shown in FIG. 83, particularly showing the clamping mechanism in a closed position.

Once the retainer 20 (or retainer 230) is firmly mounted within the plug base aperture 26, the retainer 20 is actuated to secure the stimulation lead 12 within the plug base aperture 26, as illustrated in FIG. 90. In particular, the clamping mechanism 162 is slid relative to the disk 164 to laterally slide the movable clamping bar 184 towards the fixed clamping bar 176 of the disk 164, thereby securing the stimulation lead 12 received within the slot 166, and specifically, clamping the stimulation lead 12 between the movable clamping bar 184 and the fixed clamping bar 176 of the disk 164. Once the stimulation lead 12 is secured, the locking element of the clamping mechanism 162 can be actuated to lock the movable clamping bar 184 relative to the disk 164. In particular, the movable clamping bar 184 can be slid towards the fixed clamping bar 176 until the locking tab 202 abuts the recessed stop 182. The clamping mechanism 162 can be actuated to unlock the movable clamping bar 184 relative to the disk 164, e.g., by flexing the resilient arm 200 by applying a downward force on the recess 212 of the locking tab 202 via a tool.

Figure 91:
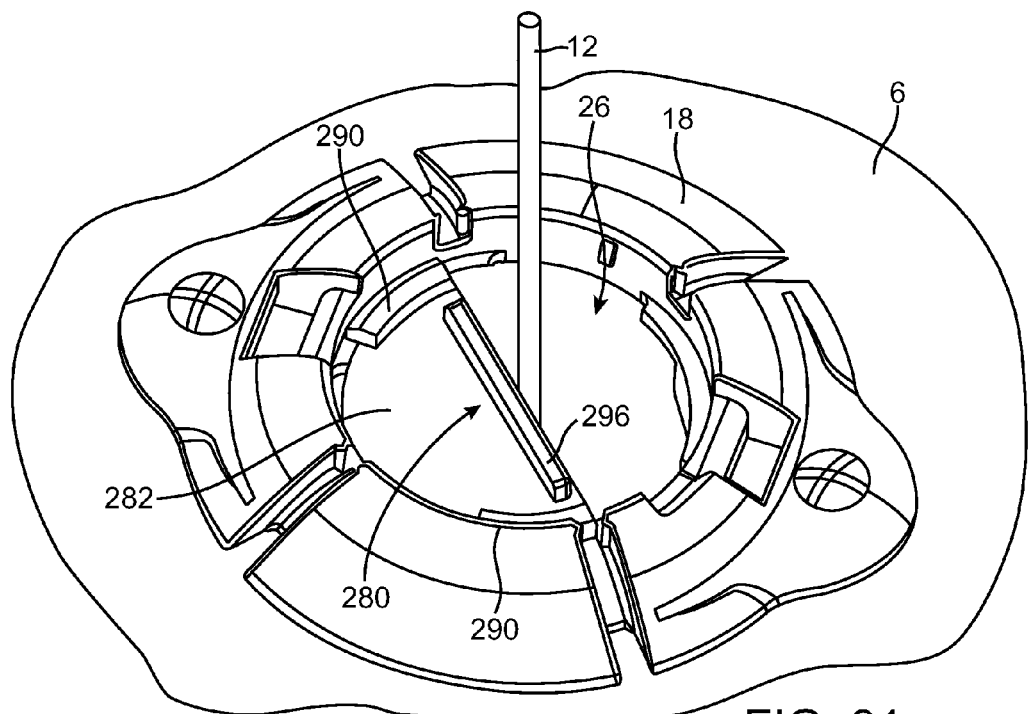
FIG. 91 is a perspective view of the retaining disk of the retainer of FIG. 58 mounted within the plug base shown in FIG. 83.
Figure 92:
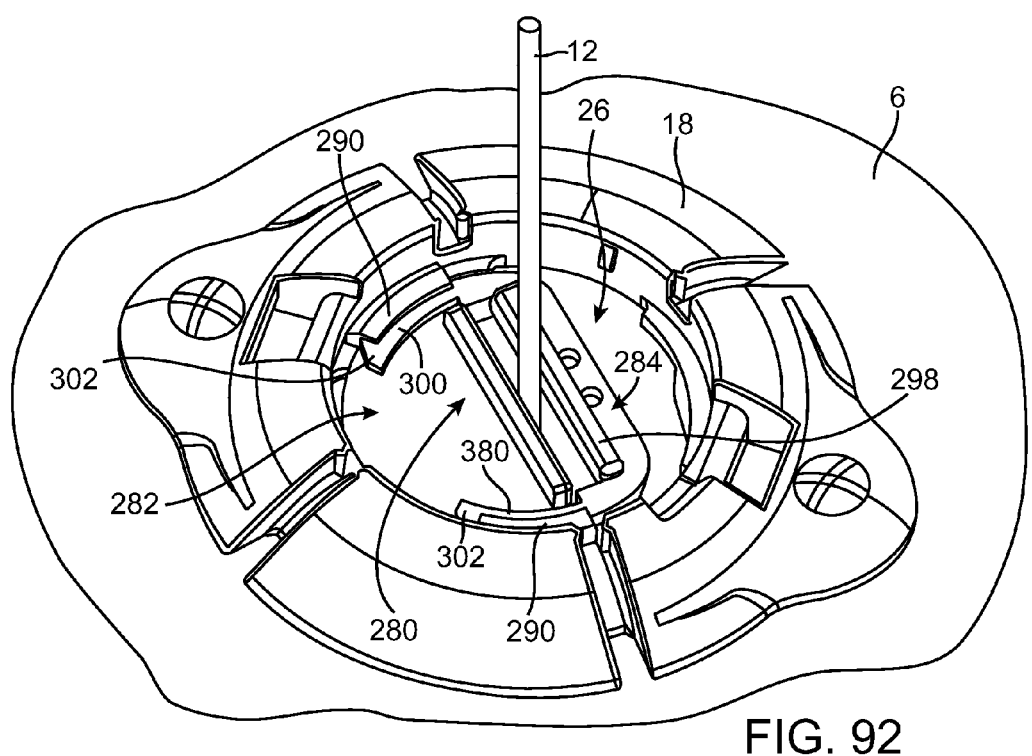
FIG. 92 is a perspective view of the clip of the retainer of FIG. 58 mounted to the retaining disk shown in FIG. 91.
Figure 93:
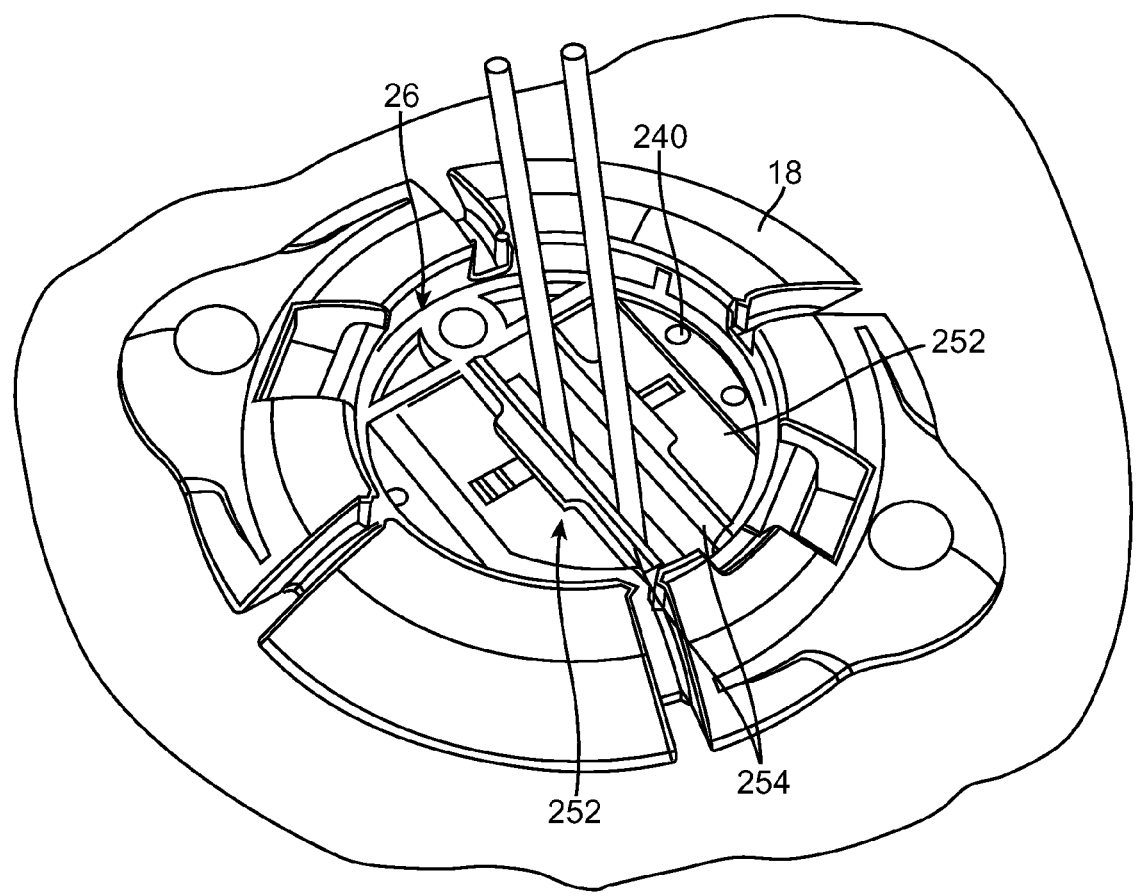
FIG. 93 is a perspective view of the retainer of FIG. 45 mounted within the plug base shown FIG. 83.

Notably, if the retainer 280 illustrated in FIGS. 50 and 51 is used, the retaining support 282 can be mounted within the aperture 26 of the plug base 18, as illustrated in FIG. 91, and then the arms 300 of the clip 284 can be slid into the C-channels 290 located on the semi-circular flange 286 until the locking tabs 302 engage the ends of the C-channels 290 to secure the stimulation lead 12 between the clamping bars 296, 298, as illustrated in FIG. 92. If a plurality of stimulation leads 12 are to be secured, the retainer 240 illustrated in FIG. 45 can be mounted within the plug base aperture 26 in a similar manner as the retainer 20 described above. The clamping mechanisms 252 can then be slid to secure the stimulation leads 12 between the clamping bars 254, as illustrated in FIG. 93. As shown, the stimulation leads 12 are secured along an off-center chord of the plug base aperture 26.

Figure 44:
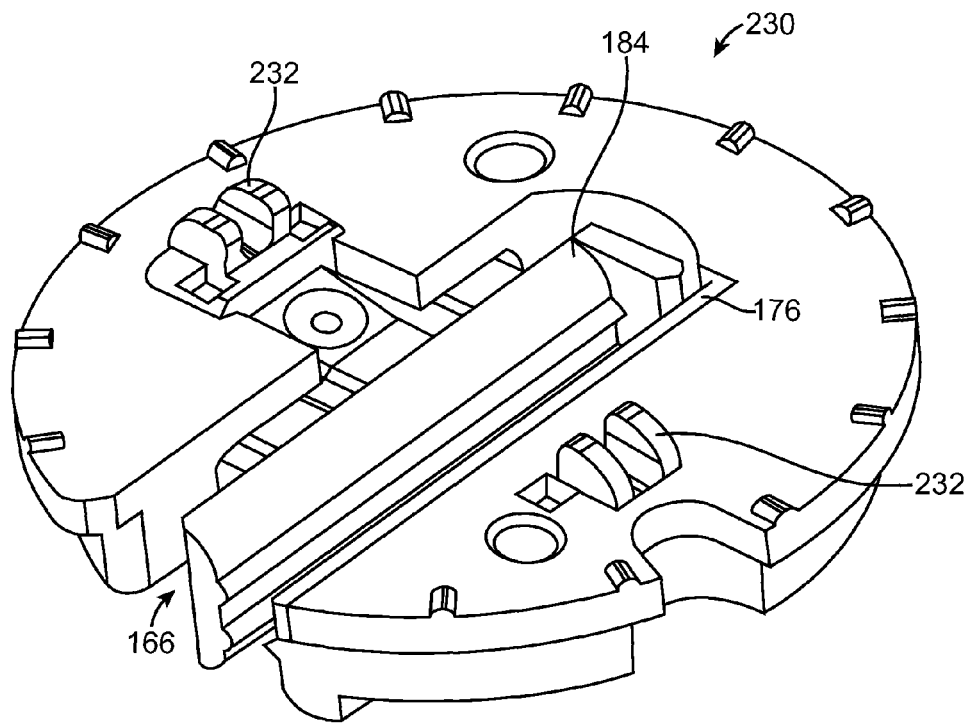
FIG. 44 is a top perspective view of an alternative embodiment of a retainer that can be used in the burr hole plug of FIG. 2.
Figure 94:
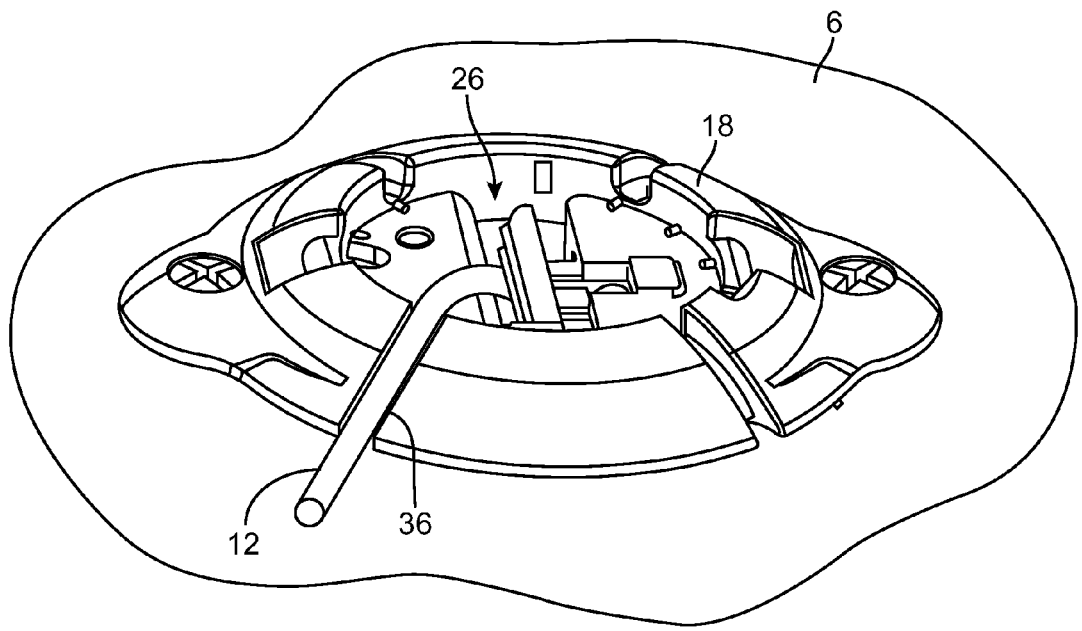
FIG. 94 is a perspective view of the retainer of FIG. 28 mounted within the plug base shown in FIG. 83, particularly showing the clamping mechanism in a closed position.
Figure 95:
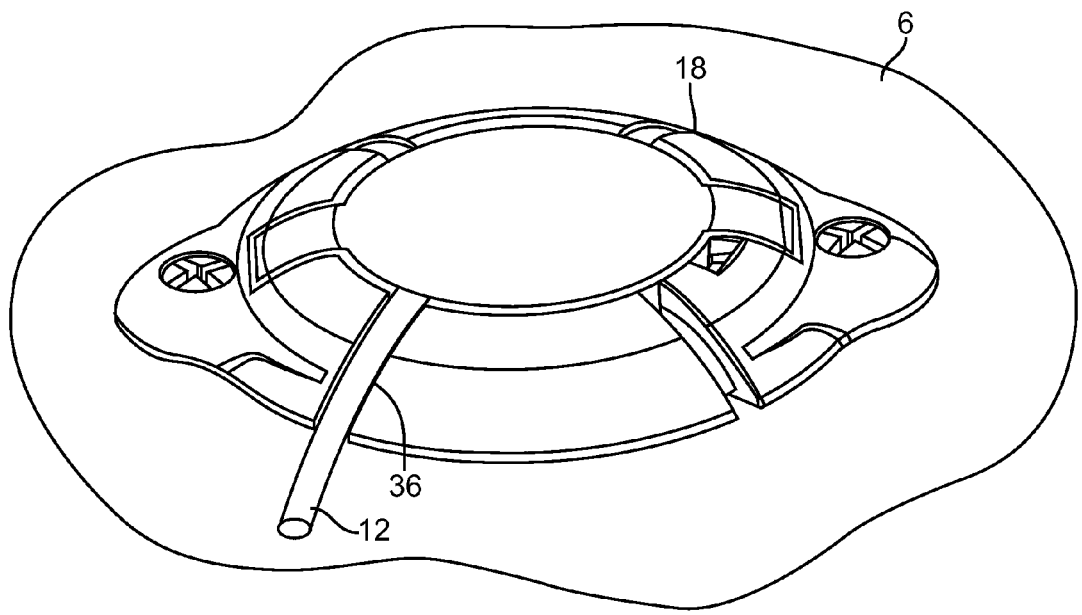
FIG. 95 is a perspective view of the cap of FIG. 52 mounted to the plug base shown in FIG. 83.

After the stimulation lead 12 (or leads) is secured within the plug base aperture 26, the stimulation lead 12 is radially directed towards the plug base 18 by bending the stimulation lead 12 at an angle (e.g. perpendicular) relative to an axis of the burr hole 5 and seating the stimulation lead 12 within one of the lead exit grooves 36 located on the plug base 18, as illustrated in FIG. 94. If the retainer 230 illustrated in FIG. 44 is used, the stimulation lead 12 may be seated within one of the lead exit grooves 232. Next, the cap 22 is mounted to the plug base 18 over the retainer 20, such that the stimulation lead 12 is secured between the plug base 18 and the cap 22, as illustrated in FIG. 95. Notably, the lead clamp groove 320 of the cap 22 will capture and apply downward pressure to the stimulation lead 12 to frictionally secure the stimulation lead 12 within the exit groove 36 of the plug base 18.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A cranial burr hole plug, comprising:
    a plug base configured for being mounted around a cranial burr hole, the plug base including an aperture through which a plurality of elongated medical devices exiting the burr hole may pass; and
    a retainer configured for being mounted within the aperture of the plug base, the retainer including a retainer support, a slot formed in the retainer support for receiving the medical devices, and first and second slidable clamping mechanisms slidably engaged with the retainer support for securing the medical devices received within the slot, said first and second slidable clamping mechanisms securing the medical devices therebetween within the aperture of the plug base.

2. The burr hole plug of claim 1, wherein the aperture of the plug base is circular.

3. The burr hole plug of claim 1, wherein the greatest dimension of the aperture is equal to or less than 25mm.

4. The burr hole plug of claim 1, wherein the retainer is configured for being removably mounted within the aperture of the plug base.

5. The burr hole plug of claim 1, wherein the plug base includes at least one inner annular ledge configured for supporting the retainer when mounted within the aperture of the plug base.

6. The burr hole plug of claim 1, wherein the first and second slidable clamping mechanisms are configured for securing the medical devices along any one of a plurality of chords of the aperture of the plug base.

7. The burr hole plug of claim 1, wherein the retainer support is a disk.

8. The burr hole plug of claim 1, wherein each of the first and second clamping mechanisms has a clamping bar and a slidable flange slidably engaged with the retainer support to laterally slide the clamping bar to secure the medical devices received within the slot.

9. The burr hole plug of claim 8, wherein at least one of the first and second clamping bars has a clamping surface with relief features.

10. The burr hole plug of claim 8, wherein each of the first and second clamping mechanisms has a locking element configured for locking the respective clamping bar relative to the retainer support when the medical devices are secured.

11. The burr hole plug of claim 8, wherein the retainer includes first and second recesses formed in the retainer support on opposite sides of the slot, wherein the slidable flanges of the first and second clamping mechanisms are slidably engaged within the respective recesses.

12. The burr hole plug of claim 11, wherein the retainer includes first and second pairs of C-channels, each pair disposed on opposite sides of the respective recess, wherein a pair of opposing edges of each slidable flange are respectively received within the respective C-channels.

13. The burr hole plug of claim 8, wherein the retainer support includes first and second portions, and the retainer further includes a hinge coupled to the first and second flange portions, whereby the first and second flange portions can be alternately hinged open to laterally receive the medical leads within the slot and hinged closed to encompass the medical lead within the slot.

14. The burr hole plug of claim 1, wherein the slot is configured for laterally receiving the medical devices.

15. The burr hole plug of claim 1, further comprising fasteners configured for anchoring the plug base to a cranium of a patient.

16. The burr hole plug of claim 15, wherein the plug base has a plurality of exit grooves configured for respectively seating the medical devices, and wherein the cap is configured for firmly securing the medical devices within the exit grooves when the cap is mounted to the plug base.

17. The burr hole plug of claim 1, further comprising a cap configured for being mounted to the plug base over the retainer.

18. A method of performing a medical procedure on a patient, comprising:
   introducing at least one elongated medical device through a cranial burr hole of the patient and into the brain tissue of the patient;
   mounting a plug base around the cranial burr hole, such that the at least one medical device extends through an aperture of the plug base;
   mounting a retainer within the aperture of the plug base, the retainer including a retainer support, a slot formed in the retainer support, and first and second clamping mechanisms receiving the at least one medical device into the slot; and
   sliding the first and second clamping mechanisms relative to the retainer support to secure the at least one medical device received within the slot and between said first and second clamping mechanisms.

19. The method of claim 18, wherein each of the at least one medical device is an electrical lead.

20. The method of claim 18, wherein the at least one medical device comprises a plurality of medical devices.

21. The method of claim 20, wherein the first and second clamping mechanisms secure the medical devices along an off-center chord of the aperture of the plug base.

22. The method of claim 18, further comprising mounting a cap to the plug base over the retainer.

* * * * *